United States Patent
Ma et al.

(10) Patent No.: US 11,479,529 B2
(45) Date of Patent: Oct. 25, 2022

(54) COMPOUNDS WITH ANTIMICROBIAL ACTIVITY

(71) Applicants: The Hong Kong Polytechnic University, Hong Kong (CN); The Chinese University of Hong Kong, Hong Kong (CN)

(72) Inventors: Cong Ma, Hong Kong (CN); Xiao Yang, Hong Kong (CN)

(73) Assignees: The Hong Kong Polytechnic University, Hong Kong (CN); The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/959,142

(22) PCT Filed: Jan. 8, 2019

(86) PCT No.: PCT/IB2019/050137
§ 371 (c)(1),
(2) Date: Jun. 29, 2020

(87) PCT Pub. No.: WO2019/138323
PCT Pub. Date: Jul. 18, 2019

(65) Prior Publication Data
US 2020/0347010 A1 Nov. 5, 2020
US 2021/0317076 A9 Oct. 14, 2021

Related U.S. Application Data

(60) Provisional application No. 62/615,418, filed on Jan. 9, 2018.

(51) Int. Cl.
C07C 251/86 (2006.01)
A61P 31/04 (2006.01)
(Continued)

(52) U.S. Cl.
CPC ............ *C07C 251/86* (2013.01); *A61P 31/04* (2018.01); *C07C 215/50* (2013.01);
(Continued)

(58) Field of Classification Search
None
See application file for complete search history.

(56) References Cited

U.S. PATENT DOCUMENTS 2,784,138 A 3/1957 Wegler et al.
4,056,540 A 11/1977 Buchanan et al.

FOREIGN PATENT DOCUMENTS

CN 102276500 A 12/2011
CN 103787913 A 5/2014
(Continued)

OTHER PUBLICATIONS

Kousar et al. "Synthesis and Biological Activity of Important Phenolic Mannich Bases" Asian Journal of Chemistry, 2013, vol. 25, No. 1, pp. 59-62.*
(Continued)

*Primary Examiner* — Joseph R Kosack
(74) *Attorney, Agent, or Firm* — Spruson & Ferguson (Hong Kong) Limited

(57) ABSTRACT

This invention relates to compounds of formula 1, 2 or 3

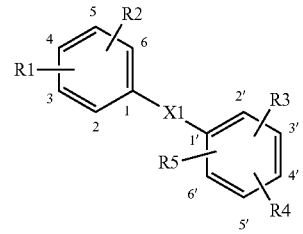

Formula 1

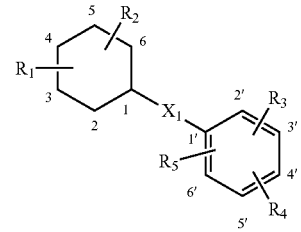

Formula 2

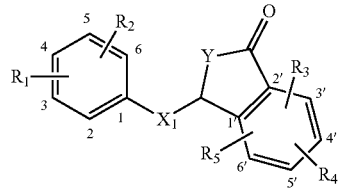

Formula 3 a pharmaceutically acceptable salt, or solvate thereof, wherein $X_1$, Y, $R_1$, $R_2$, $R_3$, $R_4$, and $R_5$ are as defined herein. The compounds are antimicrobial agents that may be used to treat various bacterial and protozoal infections and disorders related to such infections. The invention also relates to pharmaceutical compositions containing the compounds and to methods of treating bacterial and protozoal infections by administering the compounds of formula 1, 2 or 3.

16 Claims, 17 Drawing Sheets

Specification includes a Sequence Listing.

(51) Int. Cl.
    C07C 215/50    (2006.01)
    C07C 217/58    (2006.01)
    C07C 251/24    (2006.01)
    C07C 255/53    (2006.01)
    C07C 255/58    (2006.01)
    C07C 255/59    (2006.01)
    C07C 255/61    (2006.01)
    C07C 311/39    (2006.01)
    C07C 311/44    (2006.01)
    C07D 257/04    (2006.01)
    C07D 231/20    (2006.01)
    C07D 231/42    (2006.01)
    C07D 249/12    (2006.01)
    C07D 307/90    (2006.01)
    C07D 403/12    (2006.01)

(52) U.S. Cl.
    CPC .......... *C07C 217/58* (2013.01); *C07C 251/24* (2013.01); *C07C 255/53* (2013.01); *C07C 255/58* (2013.01); *C07C 255/59* (2013.01); *C07C 255/61* (2013.01); *C07C 311/39* (2013.01); *C07C 311/44* (2013.01); *C07D 231/20* (2013.01); *C07D 231/42* (2013.01); *C07D 249/12* (2013.01); *C07D 257/04* (2013.01); *C07D 307/90* (2013.01); *C07D 403/12* (2013.01)

(56) References Cited

FOREIGN PATENT DOCUMENTS

| EP | 1925643 A1 | 5/2008 |
| EP | 1930378 A1 | 6/2008 |
| EP | 2151445 A1 | 2/2010 |
| KR | 10-2012-0079616 A | 7/2012 |
| WO | 2005035121 A2 | 4/2005 |
| WO | 2010/123591 A2 | 10/2010 |
| WO | 2014/022923 A1 | 2/2014 |
| WO | 2015/191988 A1 | 12/2015 |

OTHER PUBLICATIONS

Lubbers et al. "Design, synthesis, and structure-activity relationship studies of new phenolic DNA gyrase inhibitors" Bioorganic & Medicinal Chemistry Letters, 2007, vol. 17, No. 16, pp. 4708-4714.*

Heckman et al. (2007) Gene Splicing and Mutagenesis by PCR-driven Overlap Extension. Nat. Protoc. 2: 924-932.

Neylon et al. (2000) Interaction of the *Escherichia coli* Replication Terminator Protein (Tus) With DNA: A Model Derived From DNA-binding Studies of Mutant Proteins by Surface Plasmon Resonance. Biochemistry 39: 11989-11999.

Tsang et al. (2019) Simple Method for Studying in Vitro Protein—Protein Interactions Based on Protein Complementation and Its Application in Drug Screening Targeting Bacterial Transcription. ACS Infect. Dis. 5: 521-527.

Qiu et al. (2019) Nusbiarylins, a new class of antimicrobial agents: Rational design of bacterial transcription inhibitors targeting the interaction between the NusB and NusE proteins. Bioorg. Chem. 92: 103203.

Qiu et al. (2019) Design, synthesis and biological evaluation of antimicrobial diarylimine and -amine compounds targeting the interaction between the bacterial NusB and NusE proteins. Eur. J. Med. Chem. 178: 214-231.

Qiu et al. (2020) HPLC, quantitative NMR and HRMS spectroscopic data of nusbiarylins as a new class of antimicrobial agents. Data Brief, 29: 105313.

EPO Communication pursuant to Rule 164(1) EPC of EP Application No. 19739015.6 issued from the European Patent Office dated Jul. 27, 2021.

Kaynar et al.; Molecular and crystal structure of 2-[(E)-[(4-Methylphenyl)imino]methyl]-4-nitrophenol: A redetermination; Crystallography Reports; vol. 61 No. 2; Apr. 2016; pp. 239-242.

Ahmed et al.; Solid phase-promoted greener synthesis and antibacterial activity of novel Schiff bases under catalytically free condition; Elixir Org. Chem; vol. 43; Feb. 2012; pp. 6960-6963.

Gürbüz et al.; Spectral Characterization and Antimicrobial Activity of Some Schiff Bases Derived from 4-Methyl-2-aminophenol; Chinese Journal of Chemistry; vol. 30, No. 4; Apr. 2012; pp. 970-978.

Popov et al.; Synthesis, structure, and properties of new phosphorus Schiff bases; Russian Journal of General Chemistry; vol. 78, No. 4; Apr. 2008; pp. 567-574.

Ogawa et al.; Tautomerism of a Nitro Derivative of N-Salicylideneaniline in Crystals; Chemistry Letters; vol. 28, No. 7; Jul. 1999; pp. 657-658.

May 14, 2019 PCT International Search Report, Int'l App'l No. PCT/IB2019/050137.

May 15, 2019 PCT Written Opinion, Int'l App'l No. PCT/IB2019/050137.

Yang et al. (2017) First-In-Class Inhibitor of Ribosomal RNA Synthesis with Antimicrobial Activity against *Staphylococcus aureus*. Biochemistry, 56: 5049-5052.

Moro et al. (2009) Virtual screening to identify lead inhibitors for bacterial NAD synthetase (NADs). Bioorganic & Medicinal Chemistry Letters. 19: 2001-2005.

Lakhe et al. (2013) Synthesis, characterization and antimicrobial activity of mixed ligand complexes of Ni(II), Cu(II) and Fe(III) ions with [phenol-2-[(3-methylphenyl)imino]methyl-4-nitro-] and [phenol-2-[(3-chlorophenyl)imino]methyl-4-nitro-]. International Journal of ChemTech Research. 5: 293-298.

Makal et al. (2011) Hydrogen bonding in Schiff bases—NMR, structural and experimental charge density studies. Dalton Trans. 40: 421-430.

Jean et al. (2011) High Burden of Antimicrobial Resistance in Asia. Int. J. Microb. Agents. 37: 291-295.

Frieden (2013) Government's Role in Protecting Health and Safety. N. Engl. J. Med. 368: 1857-1859.

Chambers et al. (2009) Waves of Resistance: *Staphylococcus aureus* in the Antibiotic Era. Nat. Rev. Microbiol. 7: 629-641.

Gardete et al. (2014) Mechanisms of vancomycin resistance in *Staphylococcus aureus*. J. Clin. Invest. 124: 2836-2840.

Nannini et al. (2010) Resistance or Decreased Susceptibility to Glycopeptides, Daptomycin, and Linezolid in Methicillin-Resistant *Staphylococcus aureus*. Curr. Opin. Pharmacol. 10: 516-521.

Jin et al. (2012) Growth Rate Regulation in *Escherichia coli*. FEMS Microbiol.Rev, 36: 269-287.

Viktorovskaya et al. (2015) Functional Divergence of Eukaryotic RNA Polymerases: Unique Properties of RNA Polymerase I Suit Its Cellular Role. Gene. 556: 19-26.

Santangelo et al. (2011) Termination and Antitermination: RNA Polymerase Runs a Stop Sign. Nat. Rev. Microbiol. 9: 319-329.

Bi et al. (2015) Design, Synthesis, Nitric Oxide Release and Antibacterial Evaluation of Novel Nitrated Ocotillol-Type Derivatives. Eur. J. Med. Chem. 101: 71-80.

Greive et al. (2005) Assembly of an RNA-protein Complex. Binding of NusB and NusE (S10) Proteins to boxA RNA Nucleates the Formation of the Antitermination Complex Involved in Controlling rRNA Transcription in *Escherichia coli* J. Biol. Chem. 280: 36397-36408.

Nodwell et al. (1993) Recognition of boxA Antiterminator RNA by the *E. coli* Antitermination Factors NusB and Ribosomal Protein S10. Cell. 72: 261-268.

Burmann et al. (2010) Fine Tuning of the *E. coli* NusB:NusE Complex Affinity to BoxA RNA Is Required for Processive Antitermination. Nucleic Acids Res. 38: 314-326.

Werner et al. (2011) Evolution of Multisubunit RNA Polymerases in the Three Domains of Life. Nat. Rev. Microbiol. 9: 85-98.

Kato et al. (2007) Construction of Consecutive Deletions of the *Escherichia coli* Chromosome. Mol. Syst. Biol. 3: 132.

(56) References Cited

OTHER PUBLICATIONS

Bubunenko et al. (2007) Essentiality of Ribosomal and Transcription Antitermination Proteins Analyzed by Systematic Gene Replacement in *Escherichia coli*. J. Bacteriol. 189: 2844-2853.

Ma et al. (2013) Inhibitors of Bacterial Transcription Initiation Complex Formation. ACS Chem. Biol. 8: 1972-1980.

Ma et al. (2016) Bacterial Transcription Inhibitor of RNA Polymerase Holoenzyme Formation by Structure-Based Drug Design: From in Silico Screening to Validation. ACS Infect. Dis. 2: 39-46.

Vassylyev et al. (2007) Structural Basis for Transcription Elongation by Bacterial RNA Polymerase. Nature 448: 157-162.

Liu et al. (2017) Structural Insights Into NusG Regulating Transcription Elongation. Nucleic Acids Res. 45: 968-974.

Burmann et al. (2010) A NusE:NusG Complex Links Transcription and Translation. Science 328: 501-504.

Yang et al. (2009) The Structure of Bacterial RNA Polymerase in Complex With the Essential Transcription Elongation Factor NusA. EMBO Rep. 10: 997-1002.

Beuth et al. (2005) Structure of a *Mycobacterium tuberculosis* NusA-RNA Complex. EMBO J. 24: 3576-3587.

Prasch et al. (2009) RNA-binding Specificity of *E. coli* NusA. Nucleic Acids Res. 37: 4736-4742.

Bubunenko et al. (2013) Nus Transcription Elongation Factors and RNase III Modulate Small Ribosome Subunit Biogenesis in *Escherichia coli*. Mol. Microbiol. 87: 382-393.

Wong et al. (2005) Mechanistic Insights on the Folding of a Large Ribozyme During Transcription. Biochemistry 44: 7535-7542.

Anderson (2003) The Process of Structure-Based Drug Design. Chem. Biol. 10: 787-797.

Said et al. (2017) Structural Basis for λN-dependent Processive Transcription Antitermination. Nat. Microbiol. 2: 17062.

Das et al. (2008) Structural Biophysics of the NusB:NusE Antitermination Complex. J. Mol. Biol. 376: 705-720.

Luo et al. (2008) Structural and Functional Analysis of the *E. coli* NusB-S10 Transcription Antitermination Complex. Mol. Cell 32: 791-802.

Stagno et al. (2011) Structural Basis for RNA Recognition by NusB and NusE in the Initiation of Transcription Antitermination. Nucleic Acids Res. 39: 7803-7815.

Yang et al. (2015) Identification of Inhibitors of Bacterial RNA Polymerase. Methods 86: 45-50.

Lipinski et al. (2001) Experimental and Computational Approaches to Estimate Solubility and Permeability in Drug Discovery and Development Settings. Adv. Drug Delivery Rev. 46: 3-26.

Cangelosi et al. (1997) Depletion of pre-16S rRNA in Starved *Escherichia coli* Cells. J. Bacteriol. 179: 4457-4463.

Halford et al. (2013) Rapid Antimicrobial Susceptibility Testing by Sensitive Detection of Precursor rRNA Using a Novel Electrochemical Biosensing Platform. Antimicrob. Agents Chemother. 57: 936-943.

O'Neil (2014) Antimicrobial resistance: Tackling a crisis for the health and wealth of nations, Wellcome Trust and HM Government, London.

Chellat et al. (2016) Targeting Antibiotic Resistance. Angew. Chem. Int. Ed. Engl. 55: 6600-6626.
Goralski et al. (2016) Inhibitors of Ribosome Rescue Arrest Growth of Francisella Tularensis at All Stages of Intracellular Replication. Antimicrob. Agents Chemother. 60: 3276-3282.
Brighenti et al. (2015) Targeted Cancer Therapy With Ribosome Biogenesis Inhibitors: A Real Possibility? Oncotarget 6: 38617-38627.
Ma et al. (2016) Bacterial Transcription as a Target for Antibacterial Drug Development. Microbiol. Mol. Biol. Rev. 80: 139-160.
Studier et al. (1986) Use of Bacteriophage T7 RNA Polymerase to Direct Selective High-Level Expression of Cloned Genes. J. Mol. Biol. 189: 113-130.
Ma et al. (2015) RNA Polymerase-Induced Remodelling of NusA Produces a Pause Enhancement Complex. Nucleic Acids Res. 43: 2829-2840.
Pettersen et al. (2004) UCSF Chimera—a Visualization System for Exploratory Research and Analysis. J. Comput. Chem. 25: 1605-1612.
CLSI, Clinical and Laboratory Standards Institute. (2015) Performance Standards for Antimicrobial Susceptibility Testing, Twenty-Fifth Informational Supplement (M100S25).
Miao Zuo et al., Synthesis and biological evaluation of Naryl salicylamides with a hydroxamic acid moiety at 5-position as novel HDACEGFR dual inhibitors, Bioorganic & Medicinal Chemistry, Elsevier, Amsterdam, NL,vol. 20, No. 14, May 15, 2012 (May 15, 2012), pp. 4405-4412, XP028502303, ISSN: 0968-0896, DOI: 10.1016/J. BMC.2012.05.034.
Waltz Fanny et al., Synthesis and Structure-Activity Relationships of a Class of Sodium Iodide Symporter Function Inhibitors, CHEMMEDCHEM Communications, vol. 6, No. 10, Jul. 12, 2011, pp. 1775-1777, XP55822199, DE; ISSN: 1860-7179, DOI: 10.1002/cmdc. 201100258.
Sun Lin et al., Synthesis, characterization and structural thermally rearrangement of ortho-amide functional benzoxazine containing acetylene group, Thermochimica Acta, vol. 668, Oct. 10, 2018, pp. 1-8, XP55822233, Amsterdam, NL, ISSN: 0040-6031, DOI: 10.1016/J.tca.2018.08.003; P-document.
Kousar Fareeha et al., Synthesis and Biological Activity of Important Phenolic Mannich Bases, Asian Journal of Chemistry, vol. 25, No. 1, Jan. 1, 2013, pp. 59-62, XP55822185, IN; ISSN: 0970-7077, DOI: 10.14233/ajchem.2013.12580.
Extended European Search Report of application No. 19739015.6 issued from the European Patent Office dated Nov. 2, 2021.

* cited by examiner

A

B

MC4

MC4-1    MC4-2

MC4-3    MC4-4

MC4-5    MC4-6

MC4-7    MC4-8

| Compound ID | EFAE 19433 | SAUR 25923 | SAUR 29213 | KPNE 700603 | ABAU 19606 | PAER 27853 | ECLO 13047 | ECOL 25922 | SPNE 49619 |
|---|---|---|---|---|---|---|---|---|---|
| MC4-1 | >256 | >256 | >256 | >256 | >256 | >256 | >256 | | 256 |
| MC4-2 | >256 | 8 | 16 | >256 | >256 | >256 | >256 | | 64 |
| MC4-3 | 256 | 32 | 64 | >256 | 256 | >256 | >256 | | 128 |
| MC4-11 (MC4) | >256 | 2 | 8 | >256 | 64 | >256 | >256 | | 16 |
| MC4-12 | >256 | 2 | 8 | >256 | 128 | >256 | >256 | | 16 |
| MC4-13 | >256 | 2 | 8 | >256 | 128 | >256 | >256 | | 16 |
| MC4-14 | >256 | 2 | 8 | >256 | 128 | >256 | >256 | | 16 |
| MC4-15 | >256 | >256 | >256 | >256 | >256 | >256 | >256 | | >256 |
| MC4-16 | >256 | 64 | >256 | >256 | 64 | >256 | >256 | | >256 |
| MC4-17 | >256 | 128 | >256 | >256 | 256 | 256 | >256 | | 128 |
| MC4-18 | >256 | 256 | >256 | >256 | 128 | 256 | >256 | | 256 |
| MC4-19 | 16 | 16 | 16 | >256 | 128 | >256 | >256 | | 8 |
| MC4-20 | >256 | 2 | 16 | >256 | 128 | >256 | >256 | | 16 |
| MC4-21 | >256 | 4 | 16 | >256 | 128 | >256 | >256 | | 8 |
| MC4-22 | >256 | 4 | 16 | >256 | 128 | >256 | >256 | | 16 |
| MC4-23 | >256 | 2 | 16 | >256 | 128 | >256 | >256 | | 16 |
| MC4-24 | >256 | 64 | >256 | 256 | 64 | >256 | >256 | | >256 |
| MC4-25 | >256 | 4 | 16 | >256 | 128 | >256 | >256 | | 32 |
| MC4-26 | >256 | 4 | 16 | >256 | 128 | >256 | >256 | | 16 |
| MC4-27 | >256 | 4 | 16 | >256 | 128 | >256 | >256 | | 16 |

Figure 9

| Compound ID | EFAE 19433 | SAUR 25923 | SAUR 29213 | KPNE 700603 | ABAU 19606 | PAER 27853 | ECLO 13047 | ECOL 25922 | SPNE 49619 |
|---|---|---|---|---|---|---|---|---|---|
| MC4-28 | >256 | 4 | 16 | >256 | 128 | >256 | >256 | | 16 |
| MC4-29 | >256 | 128 | >256 | >256 | >256 | >256 | >256 | | 256 |
| MC4-30 | >256 | >256 | >256 | >256 | >256 | >256 | >256 | | >256 |
| MC4-31 | >256 | >256 | >256 | >256 | >256 | >256 | >256 | | >256 |
| MC4-32 | 64 | 32 | 32 | >256 | >256 | >256 | >256 | | 32 |
| MC4-33 | <64 | 32 | 16 | >256 | >256 | >256 | >256 | | 32 |
| MC4-34 | <64 | 32 | 32 | >256 | 128 | >256 | >256 | | 16 |
| MC4-35 | >256 | >256 | >256 | >256 | >256 | >256 | >256 | | >256 |
| MC4-36 | >256 | >256 | >256 | >256 | >256 | >256 | >256 | | >256 |
| MC4-37 | >256 | >256 | >256 | >256 | >256 | >256 | >256 | | >256 |
| MC4-38 | 256 | 32 | 128 | >256 | >256 | >256 | >256 | | 128 |
| MC4-39 | >256 | >256 | >256 | >256 | >256 | >256 | >256 | | >256 |
| MC4-40 | >256 | 4 | 16/16 | >256 | 256 | >256 | >256 | | 64 |
| MC4-41 | >256 | >256 | >256 | >256 | >256 | >256 | >256 | | >256 |
| MC4-42 | >256 | >256 | >256 | >256 | >256 | >256 | >256 | | >256 |
| MC4-43 | >256 | 256 | >256 | >256 | >256 | >256 | >256 | | >256 |
| MC4-44 | 32 | 32 | 32 | >256 | >256 | >256 | >256 | | 32 |
| MC4-45 | >256 | 32 | 64 | >256 | >256 | >256 | >256 | | >256 |
| MC4-46 | >256 | 4 | 8 | >256 | 128 | >256 | >256 | | 64 |
| MC4-47 | >256 | 4 | 16 | >256 | 256 | >256 | >256 | | 256 |
| MC4-48 | 32 | 8 | 32 | >256 | >256 | >256 | >256 | | 32 |

Figure 9 (Continued)

| Compound ID | EFAE 19433 | SAUR 25923 | SAUR 29213 | KPNE 700603 | ABAU 19606 | PAER 27853 | ECLO 13047 | ECOL 25922 | SPNE 49619 |
|---|---|---|---|---|---|---|---|---|---|
| MC4-49 | 128 | 16 | 32 | >256 | 256 | >256 | >256 | | 64 |
| MC4-50 | >256 | 2 | 16 | >256 | 256 | >256 | >256 | | 128 |
| MC4-51 | >256 | 2 | 16 | >256 | 256 | >256 | >256 | | 64 |
| MC4-52 | >256 | 2 | 8 | >256 | 128 | >256 | >256 | | 128 |
| MC4-53 | >256 | 1 | 16 | >256 | >256 | >256 | >256 | | 128 |
| MC4-54 | 32 | 8 | 16 | >256 | 256 | >256 | >256 | | 64 |
| MC4-55 | >256 | 256 | >256 | >256 | >256 | >256 | >256 | | >256 |
| MC4-56 | >256 | 2 | 16 | >256 | 256 | >256 | >256 | | 64 |
| MC4-57 | >256 | 2 | 16 | >256 | 256 | >256 | >256 | | 64 |
| MC4-58 | >256 | 2 | 16 | >256 | 128 | >256 | >256 | | 64 |
| MC4-59 | 32 | 2 | 2 | >256 | 128 | >256 | 256 | | 8 |
| MC4-60 | 128 | 32 | 64 | >256 | >256 | >256 | >256 | | 64 |
| MC4-61 | 32 | 2 | 4 | >256 | >256 | >256 | >256 | | 8 |
| MC4-62 | 128 | 16 | 64 | >256 | 128 | >256 | >256 | | 64 |
| MC4-63 | >256 | 2 | 8 | >256 | >256 | >256 | >256 | | 64 |
| MC4-64 | >256 | 4 | 16 | >256 | 128 | >256 | >256 | | 64 |
| MC4-65 | >256 | 2 | 16 | >256 | >256 | >256 | >256 | | 64 |
| MC4-66 | >256 | 2 | 8 | >256 | 128 | >256 | >256 | | 64 |
| MC4-67 | >256 | 64 | 128 | >256 | 256 | >256 | >256 | | 128 |
| MC4-68 | 32 | 8 | 16 | >256 | 256 | >256 | >256 | | 32 |
| MC4-69 | >256 | 256 | 128 | >256 | 16 | >256 | >256 | | >256 |

Figure 9 (Continued)

| Compound ID | EFAE 19433 | SAUR 25923 | SAUR 29213 | KPNE 700603 | ABAU 19606 | PAER 27853 | ECLO 13047 | ECOL 25922 | SPNE 49619 |
|---|---|---|---|---|---|---|---|---|---|
| MC4-70 | >256 | 32 | 32 | >256 | 256 | >256 | >256 | | 128 |
| MC4-71 | >256 | 64 | >256 | >256 | >256 | >256 | >256 | | 64 |
| MC4-72 | 32 | 2 | 4 | >256 | 128 | >256 | 256 | | 8 |
| MC4-73 | >256 | 4 | 16 | >256 | 256 | >256 | >256 | | 128 |
| MC4-74 | 256 | 32 | 64 | >256 | 128 | >256 | >256 | | 8 |
| MC4-75 | >256 | 64 | 256 | >256 | >256 | >256 | >256 | | 128 |
| MC4-76 | >256 | 256 | 256 | >256 | 256 | >256 | >256 | | >256 |
| MC4-77 | | 4 | >256 | >256 | >256 | >256 | >256 | | >256 |
| MC4-78 | 32 | 4 | 32 | >256 | >256 | >256 | >256 | | 64 |
| MC4-79 | 256 | 4 | 32 | 256 | 128 | 256 | 256 | | 64 |
| MC4-80 | 64 | 8 | 16 | >256 | >256 | >256 | >256 | | 64 |
| MC4-81 | 128 | 32 | 32 | >256 | >256 | >256 | >256 | | 64 |
| MC4-82 | >256 | 4 | 16 | >256 | >256 | >256 | >256 | | 64 |
| MC4-83 | >256 | 4 | 32 | >256 | >256 | >256 | >256 | | 128 |
| MC4-84 | 8 | 1 | 4 | >256 | >256 | >256 | >256 | | 8 |
| MC4-85 | >256 | 2 | 32 | >256 | 256 | >256 | >256 | | 32 |
| MC4-86 | 64 | 2 | 2 | >256 | 256 | >256 | >256 | | 32 |
| MC4-87 | >256 | 4 | 16 | >256 | 256 | >256 | >256 | | 64 |
| MC4-88 | 8 | 2 | 2 | >256 | >256 | >256 | >256 | | 4 |
| MC4-89 | >256 | 2 | 4 | >256 | >256 | >256 | >256 | | 8 |
| MC4-90 | 128 | 4 | 16 | >256 | >256 | >256 | >256 | | 64 |

Figure 9 (Continued)

| Compound ID | EFAE 19433 | SAUR 25923 | SAUR 29213 | KPNE 700603 | ABAU 19606 | PAER 27853 | ECLO 13047 | ECOL 25922 | SPNE 49619 |
|---|---|---|---|---|---|---|---|---|---|
| MC4-91 | 256 | 128 | 128 | >256 | >256 | >256 | >256 | | 128 |
| MC4-92 | 32 | 2 | 4 | >256 | >256 | >256 | >256 | | 256 |
| MC4-93 | 32 | 8 | 8 | >256 | 64 | >256 | >256 | | 16 |
| MC4-94 | >256 | >256 | >256 | >256 | >256 | >256 | >256 | | >256 |
| MC4-95 | >256 | >256 | 128 | >256 | >256 | >256 | >256 | | 256 |
| MC4-96 | >256 | 64 | 128 | 256 | 256 | 256 | >256 | | 256 |
| MC4-97 | >256 | 64 | 32 | >256 | >256 | >256 | >256 | | 128 |
| MC4-98 | 256 | 128 | 128 | >256 | 16 | 256 | 256 | | 256 |
| MC4-99 | 4 | 2 | 2 | >256 | 32 | >256 | >256 | | 8 |
| MC4-100 | 128 | 64 | 32 | >256 | 256 | >256 | >256 | | 128 |
| MC4-101 | >256 | 32 | 32 | >256 | 256 | >256 | >256 | | 64 |
| MC4-102 | 128 | 128 | 128 | >256 | >256 | >256 | >256 | | 16 |
| MC4-103 | 8 | 2 | 2 | >256 | 256 | >256 | >256 | | 16 |
| MC4-104 | 8 | 4 | 4 | >256 | >256 | >256 | >256 | | 8 |
| MC4-105 | 256 | 8 | 16 | >256 | >256 | >256 | >256 | >256 | 32 |
| MC4-106 | >256 | 16 | 64 | 256 | 256 | >256 | 256 | 256 | 32 |
| MC4-107 | 8 | 2 | 2 | 256 | 128 | >256 | 256 | 128 | 8 |
| MC4-108 | 16 | 4 | 4 | 256 | 64 | >256 | 256 | 128 | 16 |
| MC4-109 | 256 | 8 | 16 | >256 | 256 | >256 | >256 | >256 | 16 |
| MC4-110 | >256 | 8 | 8 | >256 | >256 | >256 | >256 | >256 | 16 |
| MC4-111 | >256 | 8 | 8 | >256 | 256 | >256 | >256 | 256 | 16 |

Figure 9 (Continued)

| Compound ID | EFAE 19433 | SAUR 25923 | SAUR 29213 | KPNE 700603 | ABAU 19606 | PAER 27853 | ECLO 13047 | ECOL 25922 | SPNE 49619 |
|---|---|---|---|---|---|---|---|---|---|
| MC4-112 | 64 | 32 | 16 | >256 | 128 | >256 | 256 | 128 | 32 |
| MC4-113 | 32 | 8 | 8 | >256 | 256 | >256 | 256 | 128 | 32 |
| MC4-114 | >256 | 4 | 16 | >256 | 256 | >256 | >256 | 256 | 16 |
| MC4-115 | 64 | 16 | 16 | >256 | 128 | >256 | 256 | 128 | 32 |
| MC4-116 | 32 | 8 | 8 | >256 | 32 | >256 | 256 | 128 | 16 |
| MC4-117 | >256 | 4 | 16 | >256 | 128 | >256 | >256 | >256 | 32 |
| MC4-118 | >256 | 4 | 8 | >256 | 256 | >256 | >256 | 256 | 16 |
| MC4-119 | 16 | 4 | 4 | >256 | 256 | >256 | >256 | >256 | 16 |
| MC4-120 | >256 | >256 | >256 | >256 | >256 | >256 | >256 | >256 | >256 |
| MC4-121 | 256 | 4 | 32 | >256 | >256 | >256 | >256 | >256 | 32 |
| MC4-122 | 64 | 8 | 64 | >256 | 256 | >256 | >256 | >256 | 64 |
| MC4-123 | 4 | 1 | 1 | >256 | >256 | >256 | >256 | >256 | 4 |
| MC4-124 | 8 | 1 | 2 | >256 | >256 | >256 | >256 | >256 | 8 |
| MC4-125 | 256 | 8 | 32 | >256 | >256 | >256 | >256 | >256 | 64 |
| MC4-126 | 256 | 4 | 8 | | | 256 | 128 | 128 | 64 |
| MC4-127 | 32 | 8 | 4 | | | 256 | >256 | 256 | 16 |
| MC4-128 | >256 | 4 | 16 | | | >256 | >256 | >256 | 32 |
| MC4-129 | >256 | >256 | >256 | | | >256 | >256 | >256 | >256 |
| MC4-131 | 256 | 256 | 256 | | | 256 | >256 | >256 | 256 |
| MC4-132 | >256 | >256 | >256 | | | >256 | >256 | >256 | >256 |
| MC4-133 | >256 | 256 | 16 | | | >256 | >256 | >256 | 256 |

Figure 9 (Continued)

| Compound ID | EFAE 19433 | SAUR 25923 | SAUR 29213 | KPNE 700603 | ABAU 19606 | PAER 27853 | ECLO 13047 | ECOL 25922 | SPNE 49619 |
|---|---|---|---|---|---|---|---|---|---|
| MC4-134 | 0.5 | 0.0625 | 0.25 | | | 32 | 32 | 32 | 2 |
| MC4-135 | 0.5 | 0.125 | 0.125 | | | >256 | >256 | >256 | 2 |
| MC4-136 | 256 | 32 | 64 | | | >256 | >256 | >256 | 128 |
| MC4-137 | 16 | 4 | 8 | | | >256 | >256 | >256 | 16 |
| MC4-138 | 64 | 32 | 32 | | | >256 | >256 | >256 | 16 |
| MC4-139 | 256 | 64 | 128 | | | >256 | >256 | >256 | 8 |
| MC4-140 | 8 | 2 | 2 | | | >256 | >256 | >256 | 8 |
| MC4-141 | 256 | 128 | 128 | | | >256 | >256 | >256 | 128 |
| MC4-142 | >256 | 8 | 16 | | | >256 | >256 | >256 | 16 |

Figure 9 (Continued)

COMPOUNDS WITH ANTIMICROBIAL ACTIVITY

CROSS-REFERENCE TO RELATED APPLICATIONS

This application claims the benefit of U.S. Provisional Application No. 62/615,418, filed Jan. 9, 2018. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

FIELD OF THE INVENTION

This invention relates to compounds having antimicrobial activity.

BACKGROUND OF THE INVENTION

Infections caused by the Gram-positive pathogen methicillin resistant *Staphylococcus aureus* (MRSA) have become one of the most serious public health concerns worldwide.[1] The pharmaceutical arsenal available to control MRSA is limited to vancomycin, daptomycin, and linezolid,[2] for which resistance has already evolved.[3] Therefore, there is an urgent need to validate a new antibiotic target, to develop novel antimicrobials with potent and specific activities to combat MRSA-associated infections.

In bacterial cells, rRNA comprises up to 80% of total RNA and transcription of rRNA has been shown to positively correlate with bacterial growth rate to meet the demand for protein synthesis.[4] Although rRNA synthesis is one of the most fundamental requirements for living cells, there is a noticeable discrepancy in this process. In eukaryotic cells, the ribosonmal genes are transcribed by different types of RNA polymerases, namely, RNA Pol I, Pol II and Pol III.[5] On the other hand, there is only one RNA polymerase in bacteria, which is associated with a number of elongation factors for forming so-called "rRNA antitermination complexes", which ensure efficient transcription of the rRNA genes.[6]

NusB and NusE (also known as the ribosomal protein S10 of the 30S ribosomal subunit) are highly conserved essential small transcription factors involved in the formation of rRNA antitermination complexes.[7] The protein-protein interaction between NusB and NusE represents the first regulatory step in rRNA transcription antitermination complex assembly.[8] Once a NusB-NusE heterodimer forms, it interacts with a region of the rRNA leader sequence called boxA.[9] Following binding of the NusB-NusE-boxA complex to RNA polymerase, other factors (such as NusA, NusG, and others) will be recruited, among which only NusG has a eukaryotic homologue.[10]

Because NusB and NusE are essential for bacterial cell viability,[11] this invention provides compounds for disruption of NusB-NusE heterodimer formation to result in reduced rates of rRNA synthesis and bacterial cell proliferation.

SUMMARY OF THE INVENTION

The present invention provides compounds with antimicrobial activity. In one embodiment, this invention provides a compound of formula 1 or a pharmaceutically acceptable salt, prodrug, or solvate thereof:

Formula 1

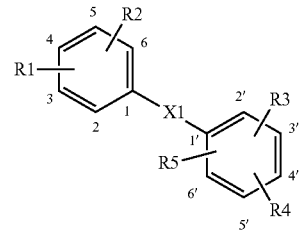

wherein:
(1) $X_1$ is selected from the group consisting of —N=CH—, —CH=N—, —CH=CH—, —NH—$CH_2$—, —$CH_2$—NH—, —$CH_2$—$CH_2$—, —$CH_2$—O—, —O—$CH_2$—, —$CH_2$—S—, —S—$CH_2$—, —S(=O)—$CH_2$—, —S(=O)—NH—, —$CH_2$—S(=O)—, —NH—S(=O)—, —S(=O)$_2$—$CH_2$—, —S(=O)$_2$—NH—, —$CH_2$—S(=O)$_2$—, —NH—S(=O)$_2$—, —C(=O)—NH—, —NH—C(=O)—, and —C(=O)—; and
(2) Each of $R_1$-$R_5$ is independently selected from the group consisting of hydrogen, hydroxy, nitro, acetyl, methyl, ethynyl, carboxy, carboxymethyl hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo.

In one embodiment, this invention provides a compound of formula 2 or a pharmaceutically acceptable salt, prodrug or solvate thereof:

Formula 2

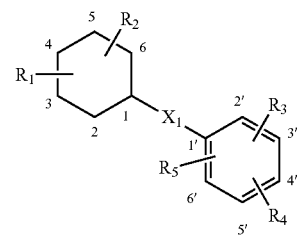

wherein:
(1) $X_1$ is selected from the group consisting of —N=CH—, —CH=N—, —CH=CH—, —NH—$CH_2$—, —$CH_2$—NH—, —$CH_2$—$CH_2$—, —$CH_2$—O—, —O—$CH_2$—, —$CH_2$—S—, —S—$CH_2$—, —S(=O)—$CH_2$—, —S(=O)—NH—, —$CH_2$—S(=O)—, —NH—S(=O)—, —S(=O)$_2$—$CH_2$—, —S(=O)$_2$—NH—, —$CH_2$—S(=O)$_2$—, —NH—S(=O)$_2$—, —C(=O)—NH—, —NH—C(=O)—, and —C(=O)— and
(2) Each of $R_1$-$R_5$ is independently selected from the group consisting of hydrogen, hydroxy, nitro, acetyl, methyl, ethynyl, carboxy, carboxymethyl hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo.

In one embodiment, this invention provides a compound of formula 3 or a pharmaceutically acceptable salt, prodrug, or solvate thereof:

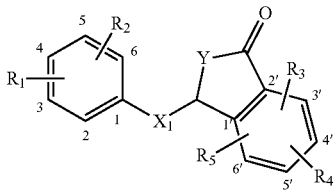

Formula 3 a pharmaceutically acceptable salt, or a solvate thereof, wherein:
(1) $X_1$ or Y is selected from the group consisting of —NH—, —$CH_2$—, —O—, and —S—; and
(2) each of $R_1$-$R_5$ is independently selected from the group consisting of hydrogen, hydroxy, nitro, acetyl, methyl, ethynyl, carboxy, carboxymethyl hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo.

In one embodiment, this invention provides a pharmaceutical composition for the treatment of a bacterial infection or a protozoal infection in mammal, fish, or bird, which comprises a therapeutically effective amount of a compound of formula 1, 2 or 3 with a pharmaceutically acceptable carrier.

In one embodiment, this invention provides a method of treating a bacterial infection or a protozoal infection in a mammal, fish, or bird that comprises administering to said mammal, fish or bird a therapeutically effective amount of a compound of formula 1, 2 or 3.

In one embodiment, this invention provides a method for preparing the compound of formula 1, 2, or 3.

DEFINITIONS & ABBREVIATIONS

The following terms shall be used to describe the present invention. In the absence of a specific definition set forth herein, the terms used to describe the present invention shall be given their common meaning as understood by those of ordinary skill in the art.

As used herein, unless otherwise indicated, the term "treating" means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus,* or *Peptostreptococcus* spp.; pharyngitis, rheumatic fever, and glomerulonephritis related to infection by *Streptococcus pyogenes,* Groups C and G streptococci, *Corynebacterium diphtheriae,* or *Actinobacillus haemolyticum*; respiratory tract infections related to infection by *Mycoplasma pneurnoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans,* including strains resistant to known antibacterials such as, but not limited to, beta-lactams, vancomycin, aminoglycosides, quinolones, chloramphenicol, tetracylines and nacrolides; uncomplicated skin and soft tissue infections and abscesses, and puerperal fever related to infection by *Staphylococcus aureus,* coagulase-negative staphylococci (i.e., *S. epidermidis, S. hemolyticus,* etc.), *Streptococcus pyogenes, Streptococcus agalactiae,* Streptococcal groups C-F (minute-colony streptococci), *viridans* streptococci, *Corynebacterium minutissimum, Clostridium* spp., or *Bartonella henselae*; uncomplicated acute urinary tract infections related to infection by *Staphylococcus aureus,* coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B, and C streptococci ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocvstitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by *Viridans streptococci*; persistent cough related to infection by *Bordetella pertussis*; gas gangrene related to infection by *Clostridium perfringens* or *Bacteroides* spp.; and atherosclerosis or cardiovascular disease related to infection by *Helicobacter* pylon or *Chlamydia pneumoniae.* Bacterial infections and protozoal infections, and disorders related to such infections, which may be treated or prevented in animals include the following: bovine respiratory disease related to infection by *P. haemolytica, P multocida, Mycoplasma bovis,* or *Bordetella* spp.; cow enteric disease related to infection by *E. coli* or protozoa (i.e., coccidia, cryptosporidia, etc.); dairy cow mastitis related to infection by *S. aureus,* Strep. *uberis, Streptococcus agalactiae, Streptococcus dysgalactiae, Klebsiella* spp., *Corynebacterium,* or *Enterococcus* spp.; swine respiratory disease related to infection by *A. pleuro, P. multocida,* or *Mycoplasma* spp.; swine enteric disease related to infection by *E. coli, Lawsonia intracellulanis, Salmonella,* or *Serpulina hyodysinteniae*; cow footrot related to infection by *Fusobacterium* spp.; cow metritis related to infection by E coil; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *S. epidermidis, S. internedius,* coagulase neg. *Staphylococcus* or *P. multocida*; and dental or mouth infections in dogs and cats related to infection by *Alcaigenes* spp., *Bacteroides* spp., *Clostridium* spp., *Enterobacter* spp., *Eubacterium, Peptostreptococcus, Porphyromonas,* or *Prevotella.* Other bacterial infections and protozoal infections, and disorders related to such infections, which may be treated or prevented in accord with the method of the present invention are referred to in J. P Sanford et al., "The Sanford Guide To Antimicrobial Therapy," 26 th Edition, (Antimicrobial Therapy, Inc., 1996).

As used herein, unless otherwise indicated, the term "halo" includes fluoro, chloro, bromo or iodo. Preferred halo groups are fluoro, chloro and bromo.

As used herein, unless otherwise indicated, the term "alkyl" includes saturated monovalent hydrocarbon radicals having cyclic, straight and/or branched moieties. It is to be understood that to include cyclic moieties, the alkyl group must include at least 3 carbon atoms.

As used herein, unless otherwise indicated, the term "alkenyl", as used herein, unless otherwise indicated, includes alkyl groups as defined above having at least one carbon-carbon double bond at some point in the alkyl chain.

As used herein, unless otherwise indicated, the term "alkynyl", as used herein, unless otherwise indicated, includes alkyl groups as defined above having at least one carbon-carbon triple bond at some point in the alkyl chain.

As used herein, unless otherwise indicated, the term "aryl" includes an organic radical derived from an aromatic hydrocarbon by removal of one hydrogen, such as phenyl or naphthyl.

As used herein, unless otherwise indicated, the term "4 to 10 membered heterocyclic" includes aromatic and non-aromatic heterocyclic groups containing one or more heteroatoms each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl purinyl, oxadiazolyl, thiadiazolyl, furazanyl, benzofurazanyl. benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

As used herein, unless otherwise indicated, the phrase "pharmaceutically acceptable salt(s)" includes salts of acidic or basic groups which may be present in the compounds of formula 1, 2 or 3. The compounds of formula 1, 2 or 3 that are basic in nature are capable of forming a wide variety of salts with various inorganic and organic acids. The acids that may be used to prepare pharmaceutically acceptable acid addition salts of such basic compounds of formula 1, 2 or 3 are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodide, and valerate salts.

BRIEF DESCRIPTION OF THE DRAWINGS

FIG. 2A. Pharmacophore model with MC4 docked in.

FIG. 9 shows the minimum inhibitory concentration of MC4 analogues on various microorganisms.

DETAILED DESCRIPTION OF THE INVENTION

Figure 1A:
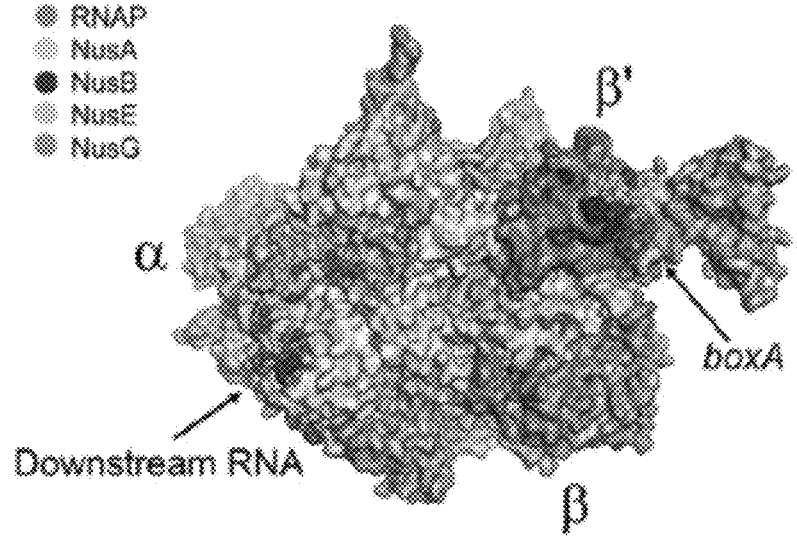
FIG. 1A. Model of the bacterial rRNA transcription complex.

The following description of certain embodiment(s) is merely exemplary in nature and is in no way intended to limit the scope of the invention, its applications, or uses.

The present invention relates to compounds of formula 1, 2 or 3 having anti-bacterial activity. In one embodiment, those compounds of the formula 1, 2 or 3 that are acidic in nature are capable of forming base salts with various pharmacologically acceptable cations. Examples of such salts include the alkali metal or alkaline earth metal salts and particularly, the sodium and potassium salts.

In one embodiment, certain compounds of formula 1, 2 or 3 may have asymmetric centers and therefore exist in different enantiomeric forms. This invention relates to the use of all optical isomers and stereoisomers of the compounds of formula 1, 2 or 3 and mixtures thereof. In particular, the invention includes both the E and Z isomers of the compound.

In one embodiment, the invention includes tautomers of the compounds of formula 1, 2 or 3.

In one embodiment, the present invention also includes isotopically-labelled compounds, and the pharmaceutically acceptable salts thereof, which are identical to those recited in formula 1, 2 or 3, but for the fact that one or more atoms are replaced by an atom having anatomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as 2H, 3H, 13C, 14C, 15N, 18O, 17O, 35S, 18F, and 36C, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as 3H and 14C are incorporated, are useful in drug and/or substrate tissue distribution assays. Tritiated, i.e. 3H, and carbon-14, i.e., 14C, isotopes are particularly preferred for their ease of preparation and detectability. Further, substitution with heavier isotopes such as deuterium, i.e., 21-1, can afford certain therapeutic advantages resulting from greater metabolic stability, for example increased in vivo half-life or reduced dosage requirements and, hence may be preferred in some circumstances. Isotopically labelled compounds of formula 1, 2 or 3 of this invention and prodrugs thereof can generally be prepared by carrying out the procedures disclosed in the Schemes and/or in the Examples and Preparations below, by substituting a readily available isotopically labelled reagent for a non-isotopically labelled reagent.

In one embodiment, this invention also encompasses pharmaceutical compositions containing, and methods of treating bacterial infections through administering, prodrugs of compounds of the formula 1, 2 or 3. Compounds of formula 1, 2 or 3 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1, 2 or 3. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, omithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

In one embodiment, the compounds of the present invention may have asymmetric carbon atoms. Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers, are considered as part of the invention.

Any compounds of formula 1, 2 or 3 that are basic in nature are capable of forming a wide variety of salts with various inorganic and organic acids.

Any compounds of the formula 1, 2 or 3 that are acidic in nature are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with any acidic compounds of formula 1, 2 or 3. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

In one embodiment, the compounds of formula 1, 2 or 3, and the pharmaceutically acceptable salts and solvates thereof (hereinafter "the active compounds"), may be administered through oral, parenteral, topical, or rectal routes in the treatment or prevention of bacterial or protozoal infections. Variations may nevertheless occur depending upon the species of mammal, fish or bird being treated and its individual response to said medicament, as well as on the type of pharmaceutical formulation chosen and the time period and interval at which such administration is carried out.

In one embodiment, the active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

In one embodiment, for oral administration, tablets containing various excipients such as microcrystalline cellulose, sodium citrate, calcium carbonate, dicalcium phosphate and glycine may be employed along with various disintegrants such as starch (and preferably corn, potato, or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

In one embodiment, for parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

In another embodiment, it is also possible to administer the active compounds of the present invention topically and this may be done by way of creams, jellies, gels, pastes, patches, ointments and the like, in accordance with standard pharmaceutical practice.

In one embodiment, for administration to animals other than humans, such as cattle or domestic animals, the active compounds may be administered in the feed of the animals or orally as a drench composition.

In one embodiment, the active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

In one embodiment, the active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross-linked or amphipathic block copolymers of hydrogels.

In one embodiment, the present invention provides a compound of formula 1,

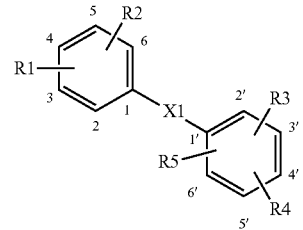

Formula 1 a pharmaceutically acceptable salt, or a solvate thereof wherein:

(1) $X_1$ is selected from the group consisting of —N=CH—, —CH=N—, —CH=CH—, —NH—CH$_2$—, —CH$_2$—NH—, —CH$_2$—CH$_2$—, —CH$_2$—O—, —O—CH$_2$—, —CH$_2$—S—, —S—CH$_2$—, —S(=O)—CH$_2$—, —S(=O)—NH—, —CH$_2$—S(=O)—, —NH—S(=O)—, —S(=O)$_2$—CH$_2$—, —S(=O)$_2$—NH—, —CH$_2$—S(=O)—, —NH—S(=O)$_2$—, —C(=O)—NH—, —NH—C(=O)—, and —C(=O)—; and (2) Each of $R_1$-$R_5$ is independently selected from the group consisting of hydrogen, hydroxy, nitro, acetyl, methyl, ethynyl, carboxy, carboxymethyl hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo.

In one embodiment, the present invention provides a compound including but not limited to:

MC1
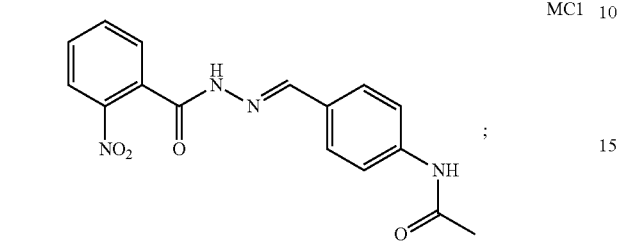

MC2
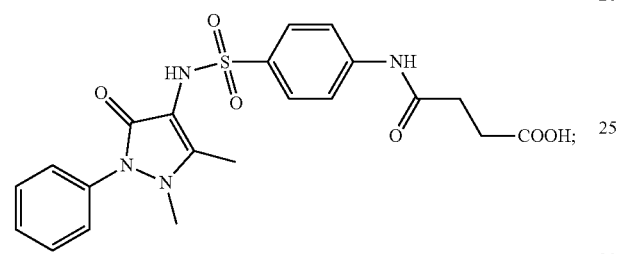

MC3
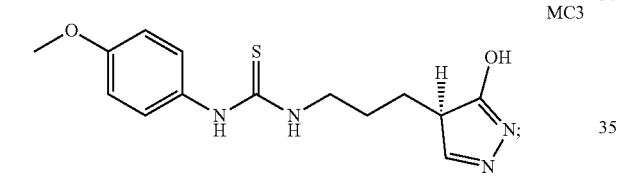

MC4
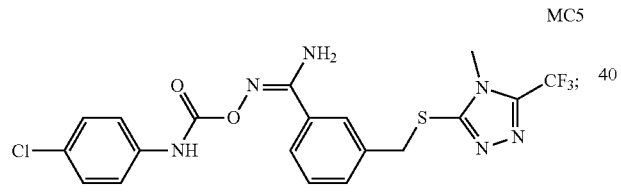

MC6
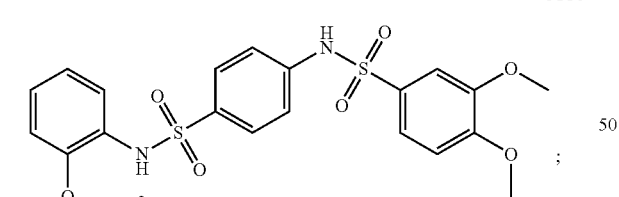

MC7

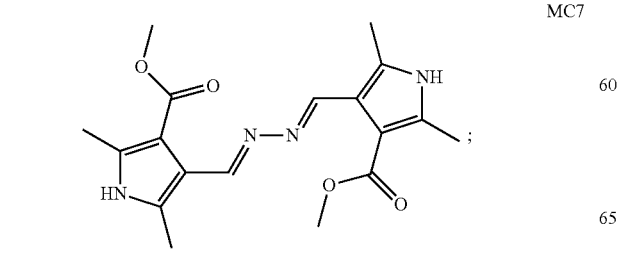

MC4-45
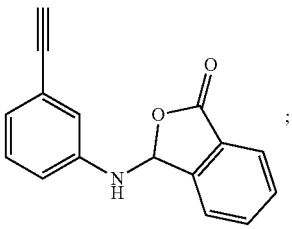

MC4-118
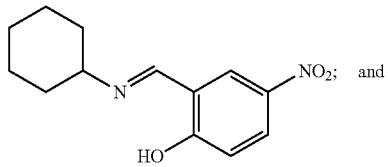

MC4-120
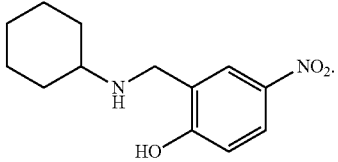

In one embodiment, the present invention provides a compound including but not limited to:

MC4 (MC4-11)
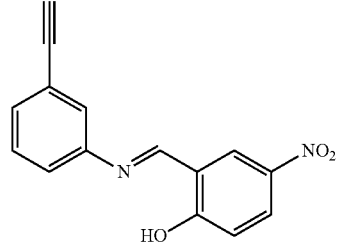

MC4-1
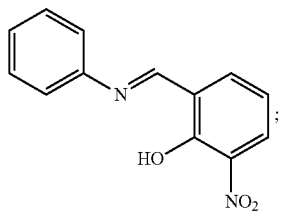

MC4-2
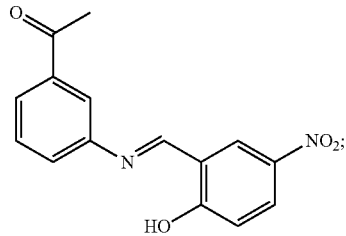

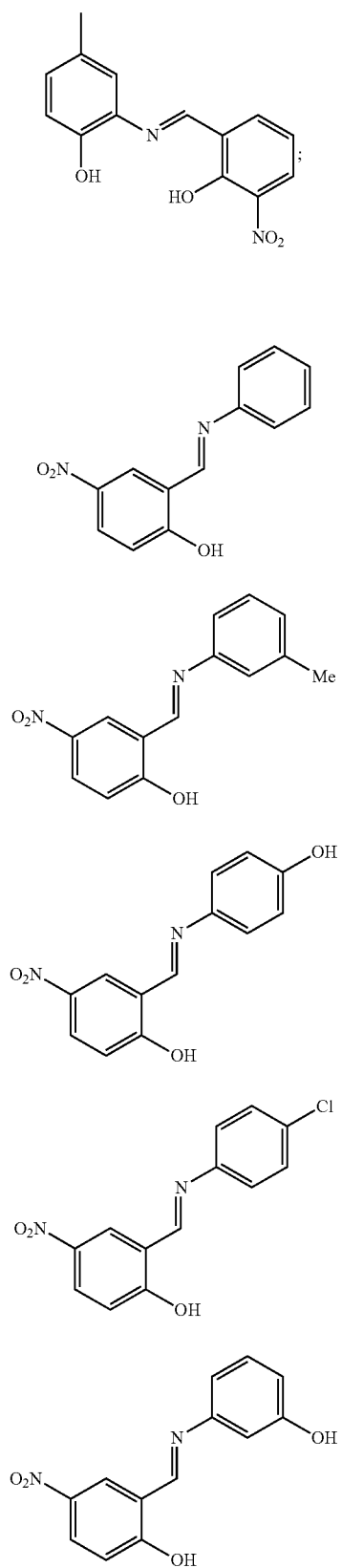

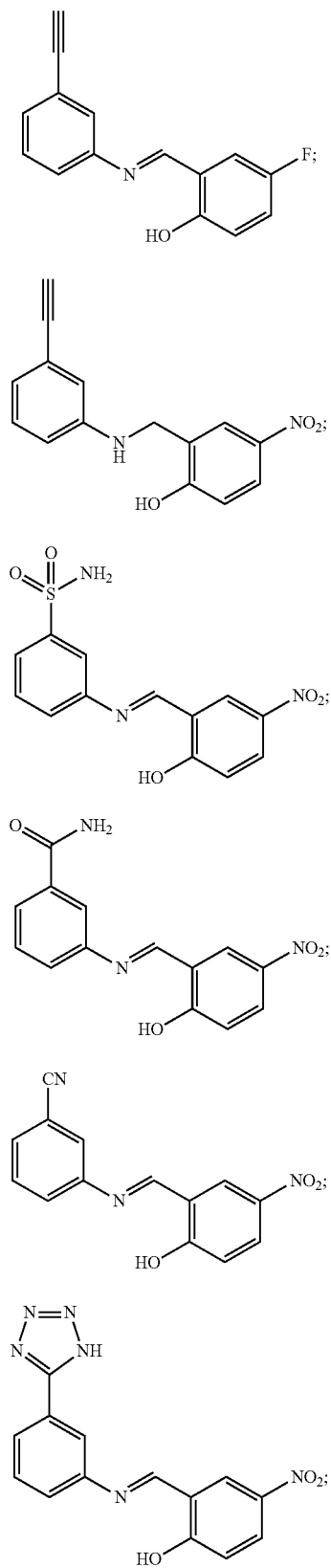
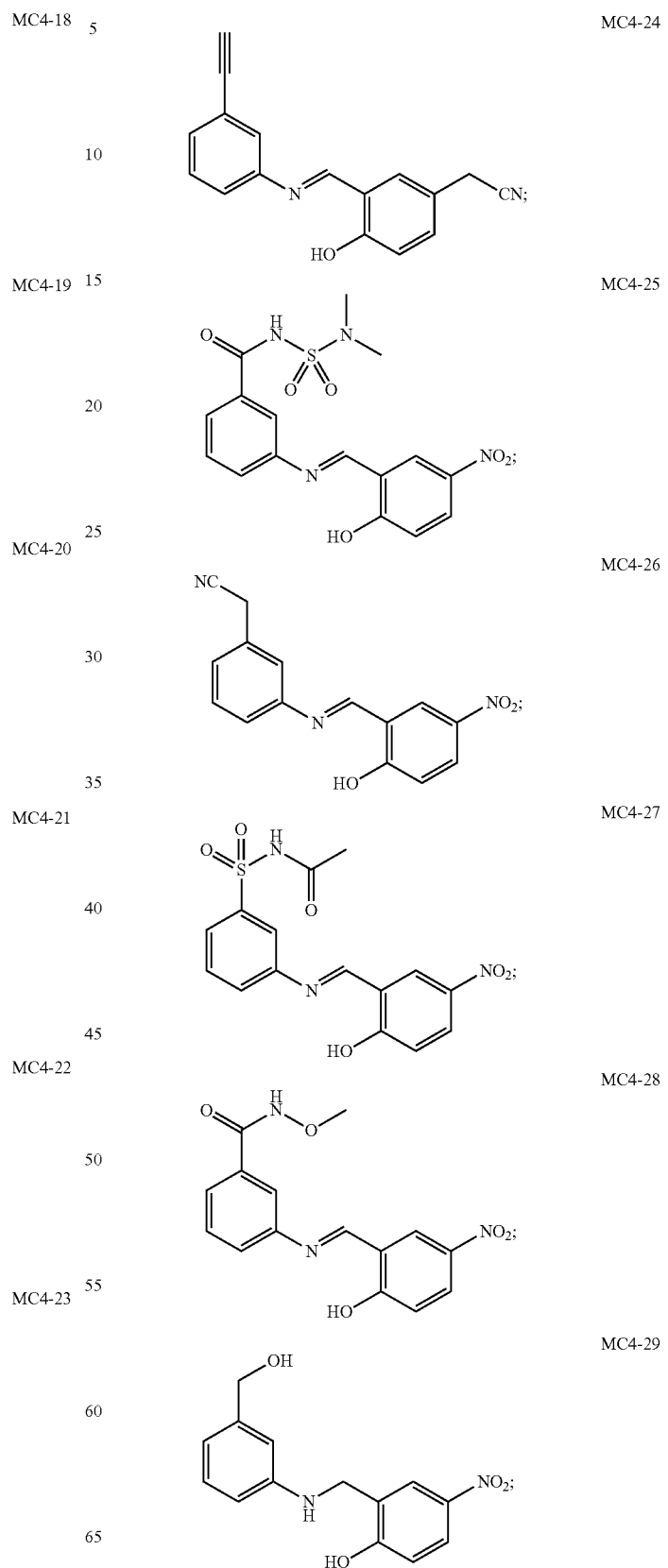

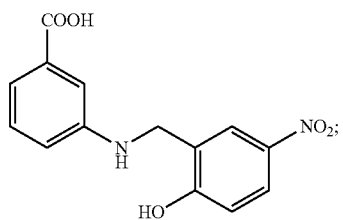 MC4-30
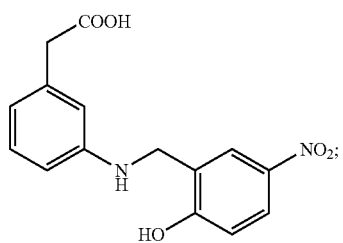 MC4-31
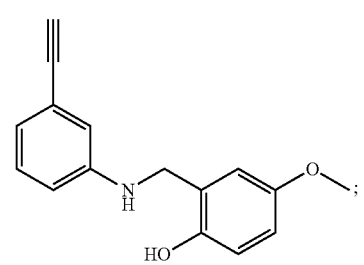 MC4-32
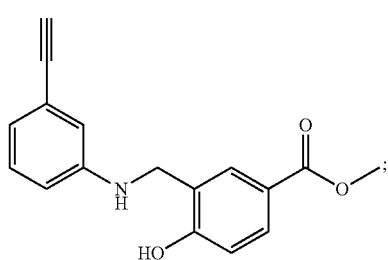 MC4-33
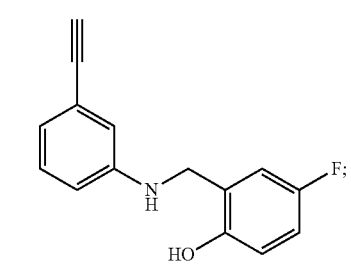 MC4-34
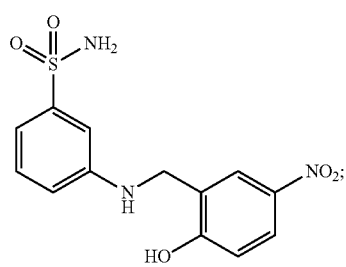 MC4-35
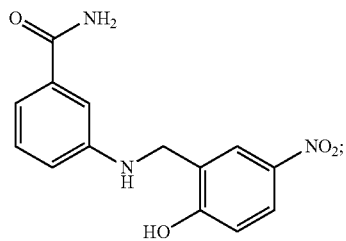 MC4-36
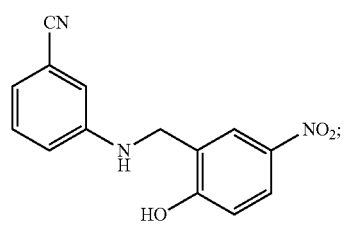 MC4-37
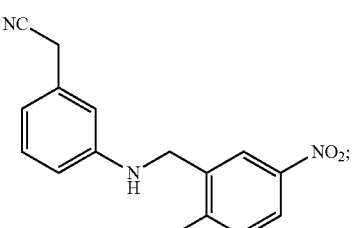 MC4-38
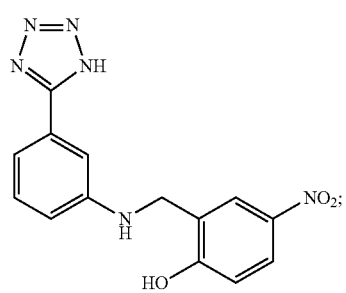 MC4-39
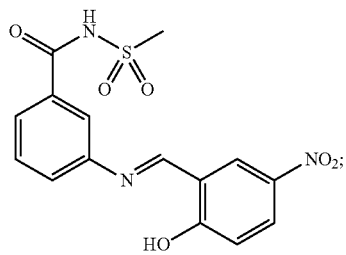 MC4-40
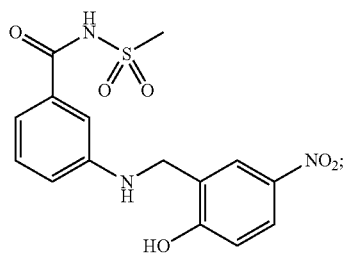 MC4-41

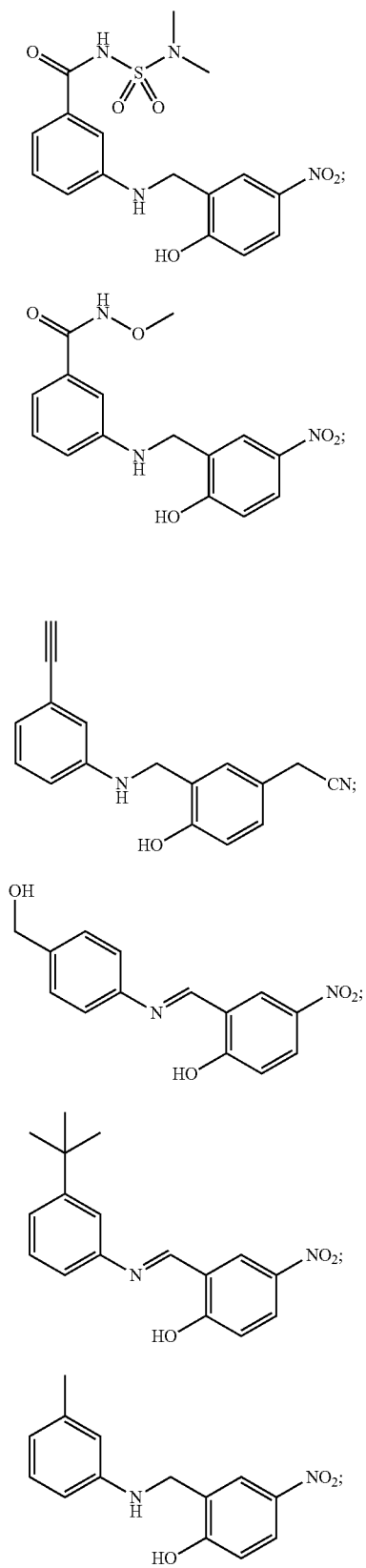
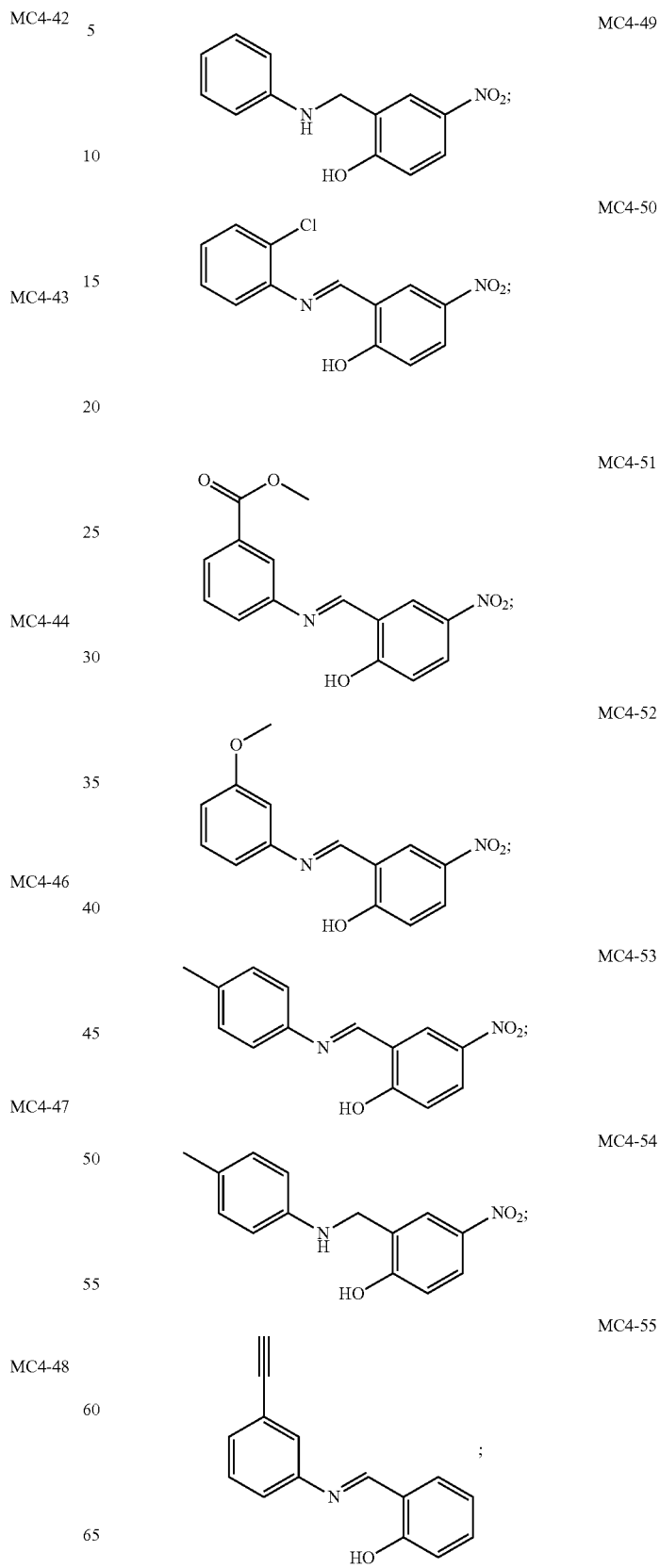

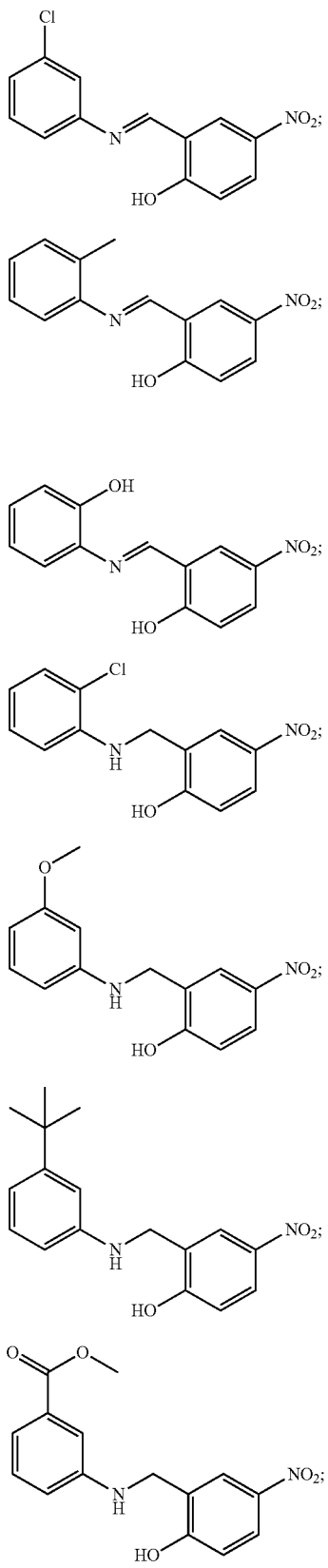
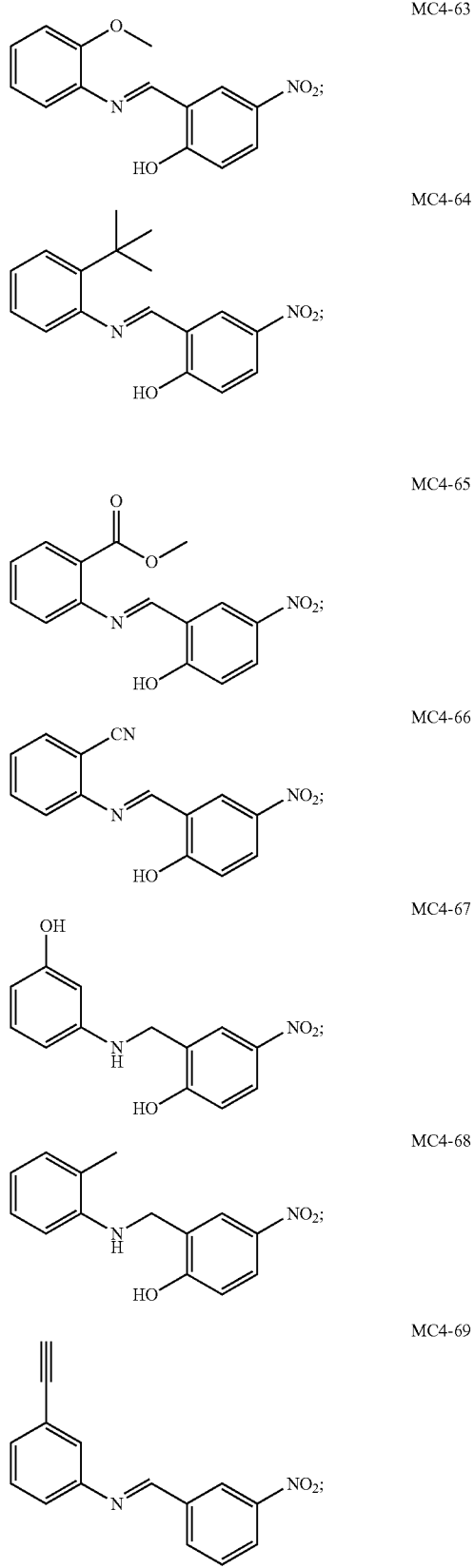

MC4-70
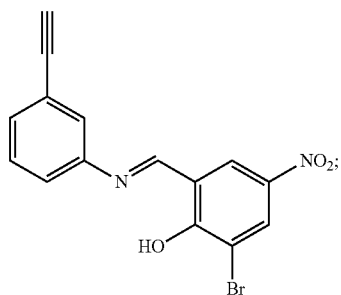
MC4-71
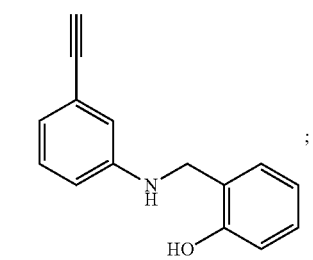
MC4-72
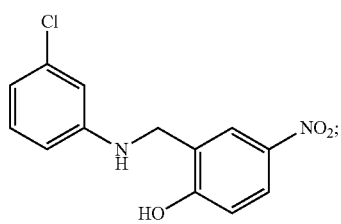
MC4-73
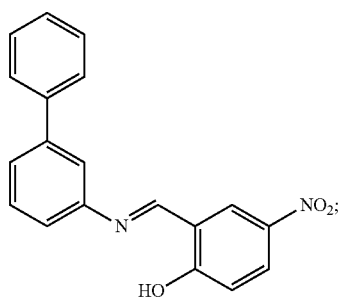
MC4-74
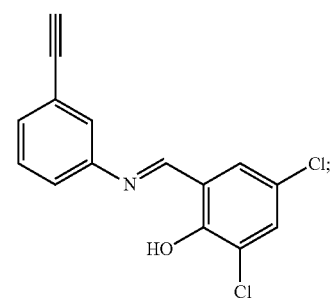
MC4-75
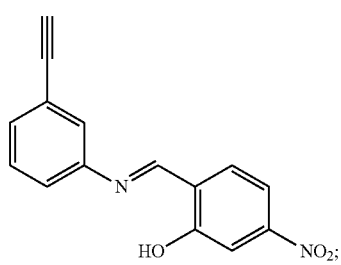
MC4-76
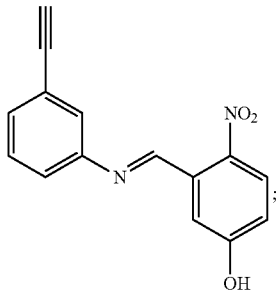
MC4-77
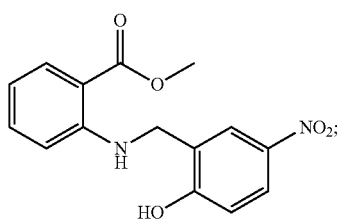
MC4-78
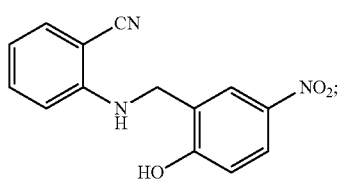
MC4-79
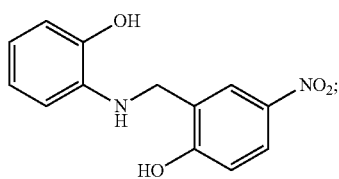
MC4-80
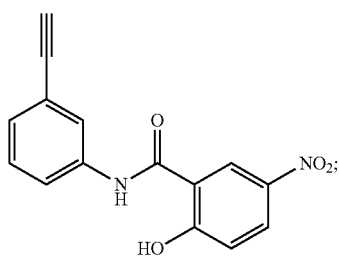
MC4-81
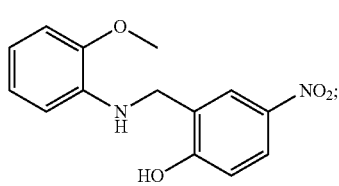
MC4-82
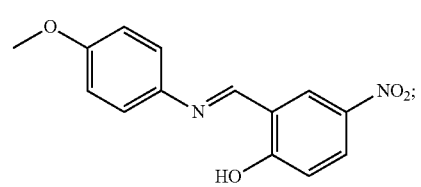

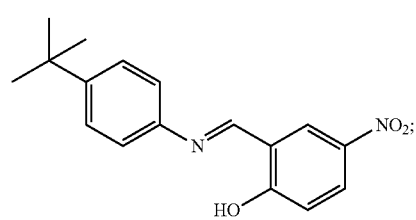
MC4-83
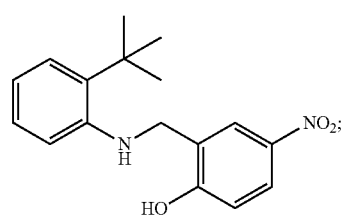
MC4-84
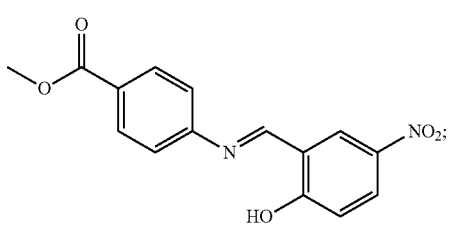
MC4-85
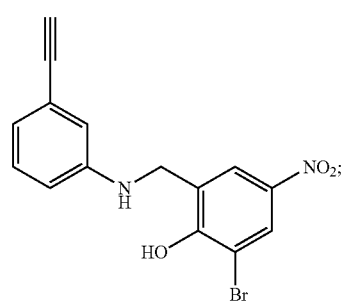
MC4-86
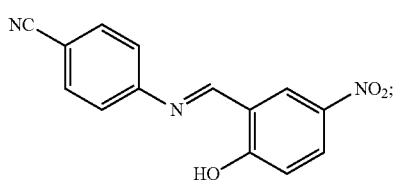
MC4-87
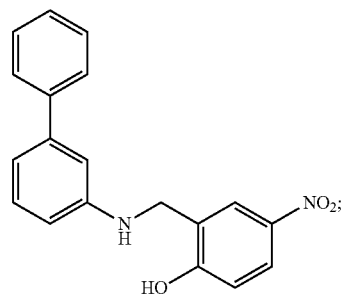
MC4-88
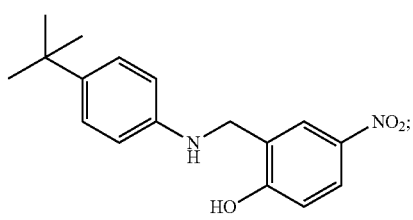
MC4-89
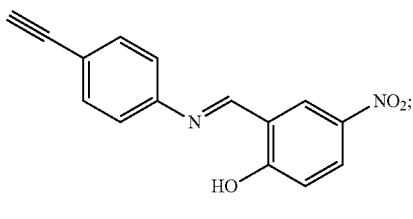
MC4-90
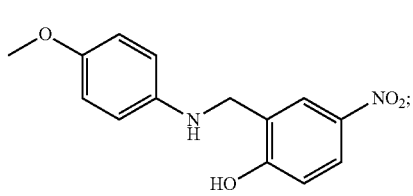
MC4-91
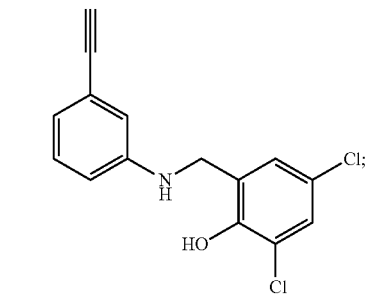
MC4-92
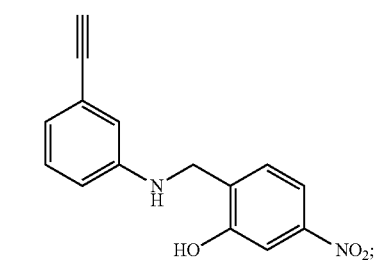
MC4-93
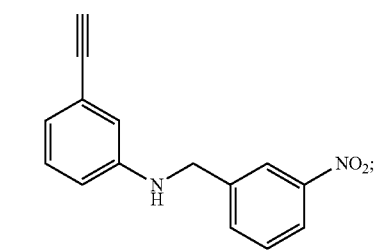
MC4-94

-continued
MC4-95
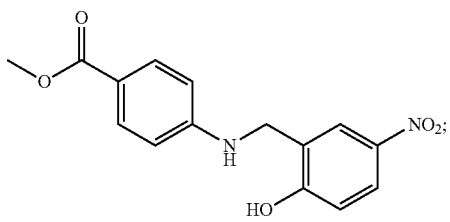
MC4-96
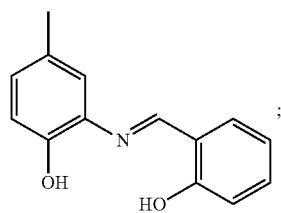
MC4-97
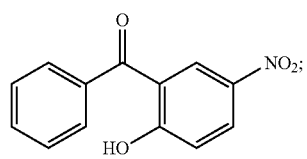
MC-98
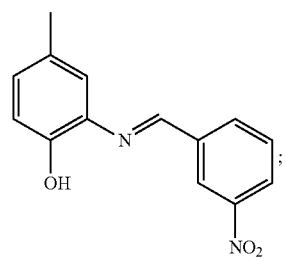
MC4-99
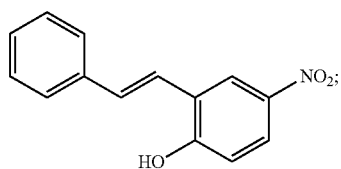
MC4-100
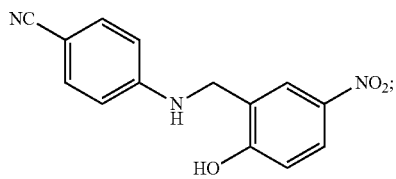
MC4-101
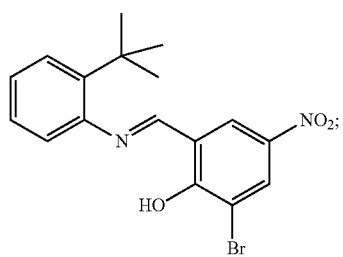
-continued
MC4-102
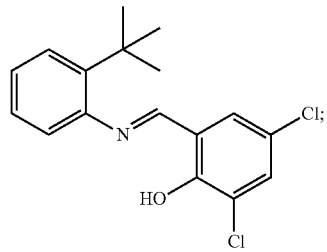
MC4-103
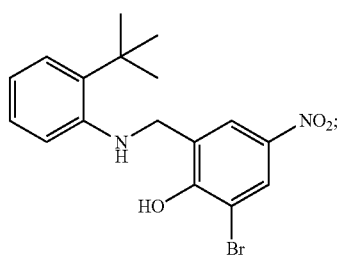
MC4-104
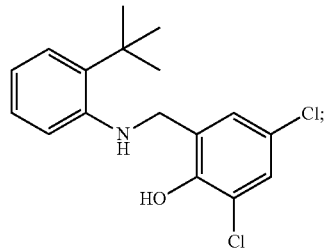
MC4-105
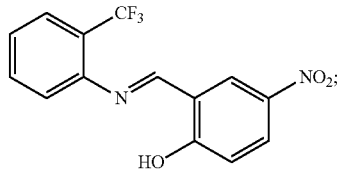
MC4-106
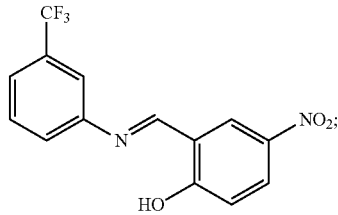
MC4-107
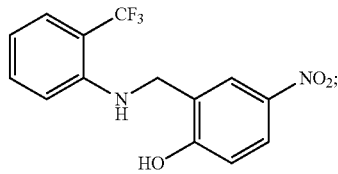
MC4-108
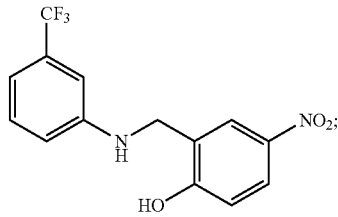

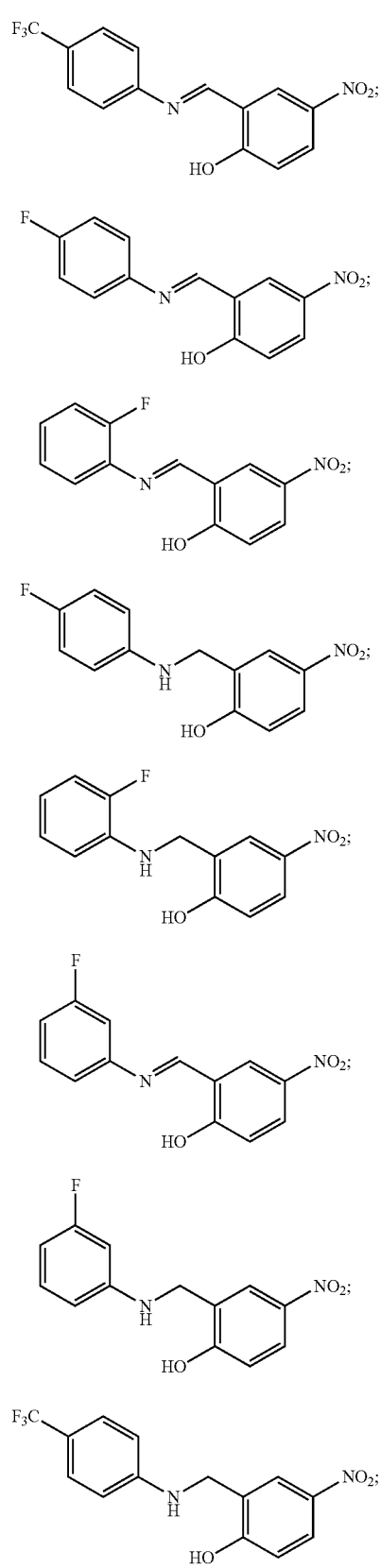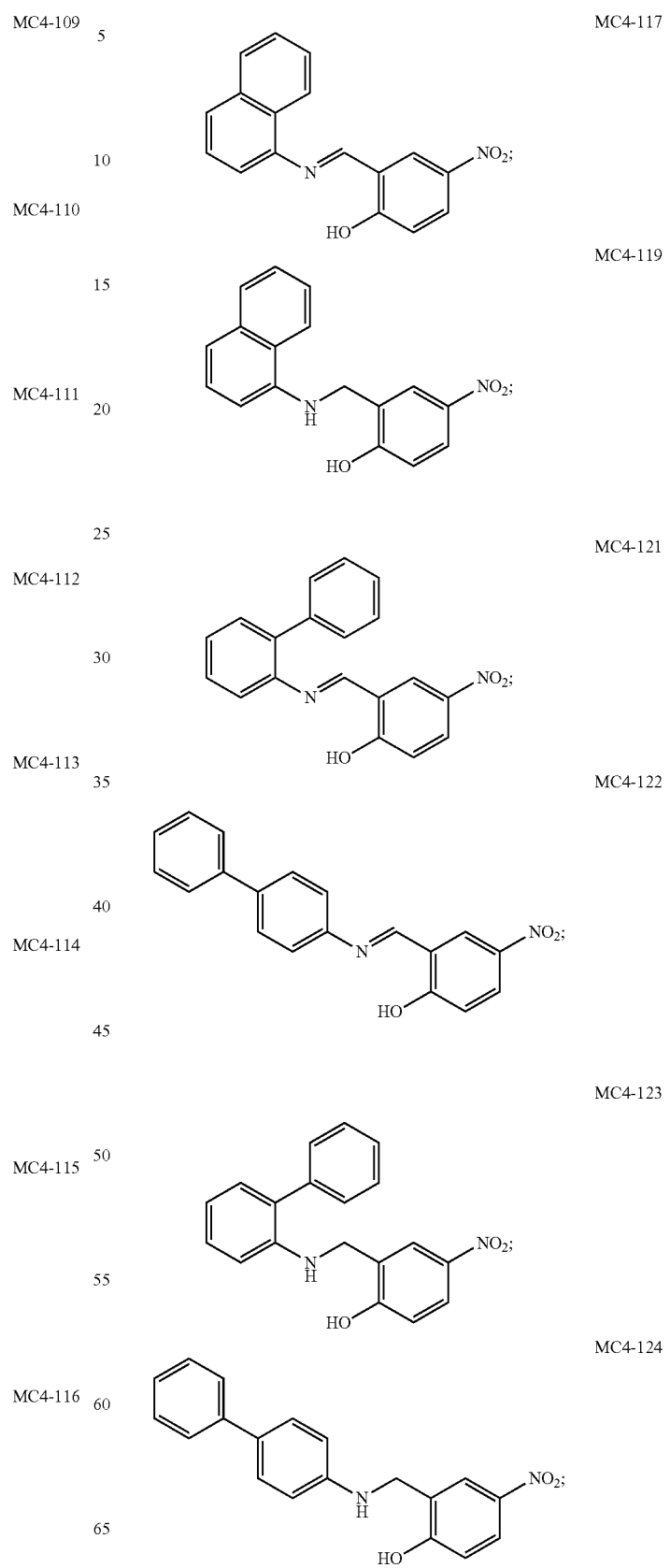

MC4-125
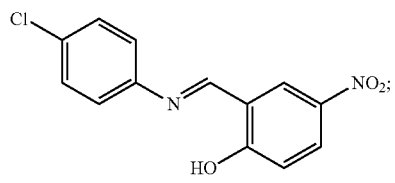
MC4-126
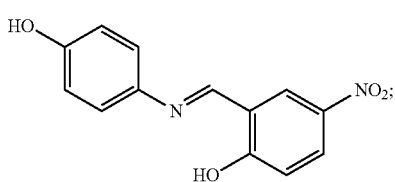
MC4-127
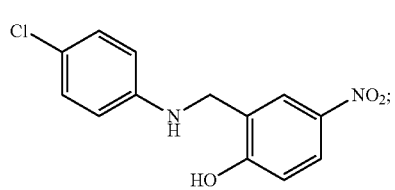
MC4-128
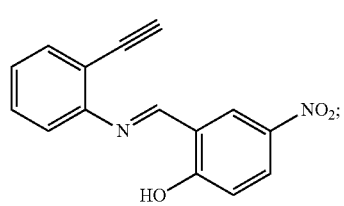
MC4-129
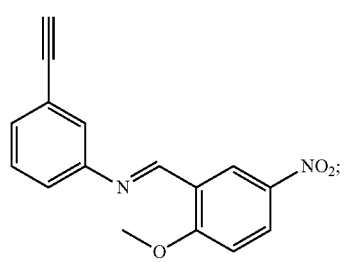
MC4-131
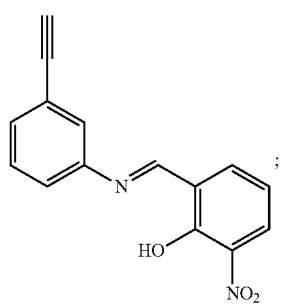
MC4-132
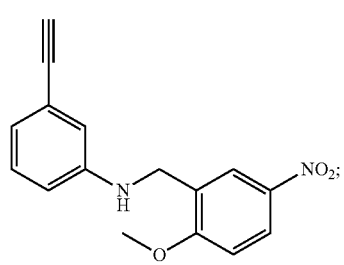
MC4-133
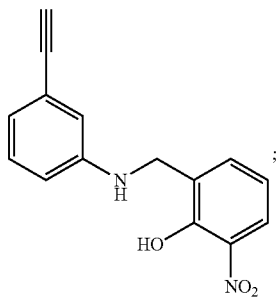
MC4-134
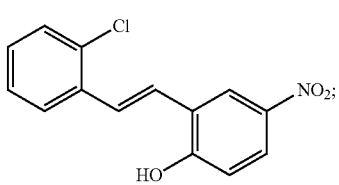
MC4-135
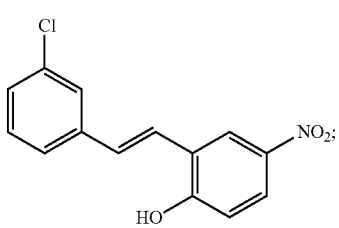
MC4-136
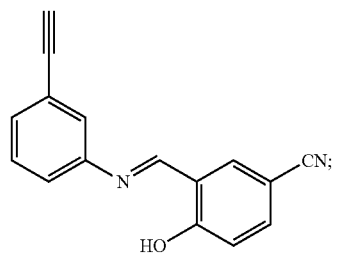
MC4-137
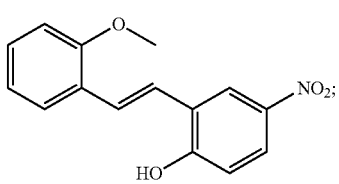
MC4-138
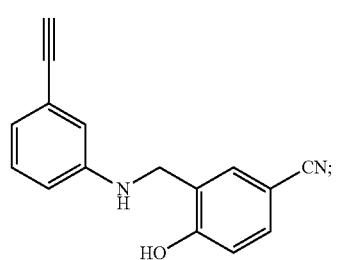

-continued

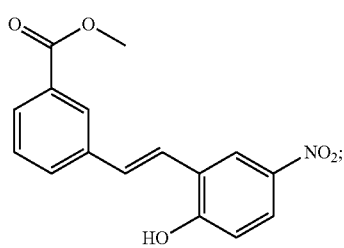

MC4-139

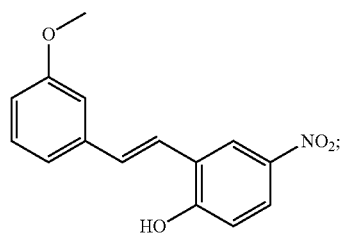

MC4-140

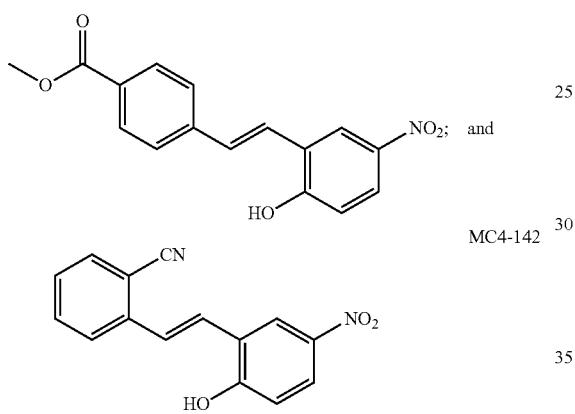

MC4-141

MC4-142

In one embodiment the present invention provides a pharmaceutical composition for treatment or prevention of bacterial or protozoal infections, comprising the compound.

In one embodiment, the composition is in the form of tablets, capsules, lozenges, troches, hard candies, powders, sprays, creams, salves, suppositories, jellies, gels, pastes, lotions, ointments, aqueous suspensions, injectable solutions, elixirs, or syrups.

In one embodiment, the pharmaceutical composition comprises 5% to 70% by weight of the compound.

In one embodiment, the bacterial or protozoal infections are caused by microorganism selected from the group consisting of *Enterococcus faecalis*, *Staphylococcus aureus*, *Klebsiella pneumoniae*, *Acinetobacter baumannii*, *Pseudomonas aeruginosa*, *Enterobacter cloacae*, *Escherichia coli*, and *Streptococcus pneumoniae*.

In one embodiment, the present invention provides a method to inhibit NusB-NusE interaction in a microorganism, comprising the step of contacting the compound with said microorganism.

In one embodiment, the NusB is selected from NusB E81, NusB Y18 and NusB E75, and NusE is selected from NusE H15, NusE D19, and NusE R16.

In one embodiment, the microorganism is selected from the group consisting of *Enterococcus faecalis*, *Staphylococcus aureus*, *Klebsiella pneumoniae*, *Acinetobacter baumannii*, *Pseudomonas aeruginosa*, *Enterobacter cloacae*, *Escherichia coli*, and *Streptococcus pneumoniae*.

In one embodiment, the present invention provides a method of treating or preventing bacterial or protozoal infections in a subject, comprising a step of administering a therapeutically effective amount of the compound to said subject.

In one embodiment, the compound is administered through an oral, parenteral, topical, or rectal route.

In one embodiment, the microorganism is selected from the group consisting of *Enterococcus faecalis*, *Staphylococcus aureus*, *Klebsiella pneumoniae*, *Acinetobacter baumannii*, *Pseudomonas aeruginosa*, *Enterobacter cloacae*, *Escherichia coli*, and *Streptococcus pneumoniae*.

In one embodiment, the NusB is selected from NusB E81, NusB Y18 and NusB E75, and NusE is selected from NusE 1-15, NusE D19 and NusE R16.

In one embodiment, the present invention provides a compound of formula 2,

Formula 2

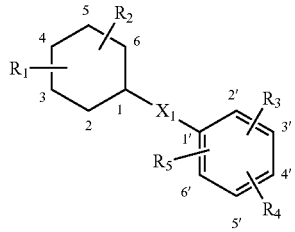

a pharmaceutically acceptable salt, or a solvate thereof, wherein (1) $X_1$ is selected from the group consisting of —N=CH—, —CH=N—, —CH=CH—, —NH—CH$_2$—, —CH$_2$—NH—, —CH$_2$—CH$_2$—, —CH$_2$—O—, —O—C$_2$—, —CH$_2$—S—, —S—CH$_2$—, —S(=O)—CH$_2$—, —S(=O)—NH—, —CH$_2$—S(=O)—, —NH—S(=O)—, —S(=O)$_2$—CH$_2$—, —S(=O)$_2$—NH—, —CH$_2$—S(=O)$_2$—, —NH—S(=O)$_2$—, —C(=O)—NH—, —NH—C(=O)—, and —C(=O)—; and (2) Each of $R_1$-$R_3$ is independently selected from the group consisting of hydrogen, hydroxy, nitro, acetyl, methyl, ethynyl, carboxy, carboxymethyl hydroxymethyl, methoxy, methoxycarbonyl, aminosulfonyl, aminocarbonyl, cyano, tetrazolyl, dimethylaiminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo.

In one embodiment, the compound is selected from the group consisting of:

MC4-118

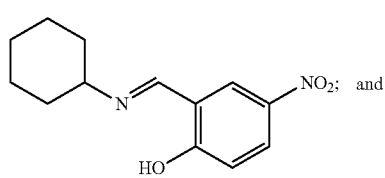

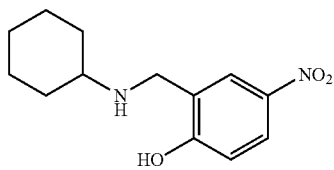

MC4-120

In one embodiment, the present invention provides a compound of formula 3,

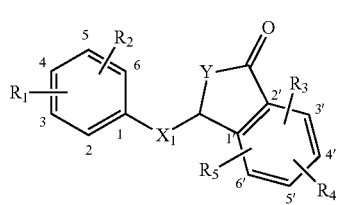

Formula 3 a pharmaceutically acceptable salt, or a solvate thereof, wherein:
(1) each of $X_1$ and Y is independently selected from the group consisting of —NH—, —$CH_2$—, —O—, and —S—; and
(2) each of $R_1$-$R_5$ is independently selected from the group consisting of hydrogen, hydroxy, nitro, acetyl, methyl, ethynyl, carboxy, carboxymethyl hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo.

In one embodiment, the compound is

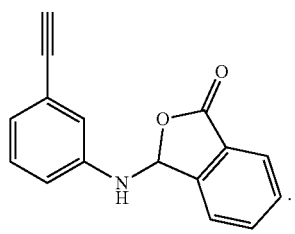

(MC4-45)

Example 1

Previously, by rational design and pharmacophore-based virtual screening, small chemical molecule inhibitors with antimicrobial activities were identified, targeting the interaction between bacterial RNA polymerase and the essential housekeeping transcription initiation factor σ.[12] Using a similar approach, an inhibitor against bacterial rRNA synthesis that has antimicrobial activities against *S. aureus* strains, including MRSA, was identified.

A bacterial rRNA transcription complex was modeled on the basis of the crystal structure of the RNA polymerase elongation complex[13] with a suite of Nus transcription factors NusA, NusB, NusE, and NusG (FIG. 1A). NusG binds to the central cleft of RNA polymerase via its N-terminal domain,[14] and its C-terminal domain interacts with NusE,[15] which anchors the NusB-NusE-boxA subcomplex to the downstream face of RNA polymerase (FIG. 1A). NusA binds to RNA polymerase near the RNA exit channel (FIG. 1A),[16] consistent with its binding to rRNA just downstream of the boxA sequence.[17] The interaction between RNA polymerase-Nus factors and rRNA results in a constrained loop, facilitating rapid and proper folding of the emerging transcript, which is consistent with previous biochemical observations that the RNA polymerase-Nus factor complex would play the role of a chaperone in rRNA synthesis.[18] This assembly also has possible roles in preventing the termination factor Rho from accessing the rRNA transcript,[19] ensuring complete transcription of the relatively large rRNA operons during rapid bacterial cell growth. Recently reported structural information about the phage protein λN-dependent transcription antitermination complex also was similar to that of the rRNA transcription complex model used in this invention.[20]

Figure 1B:
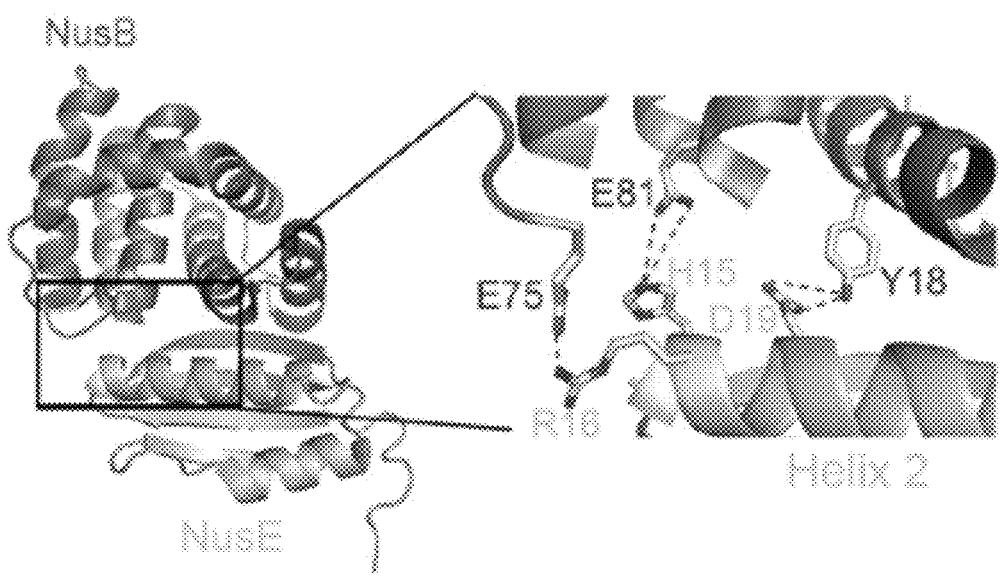
FIG. 1B. NusB-NusE interface.
Figure 5:
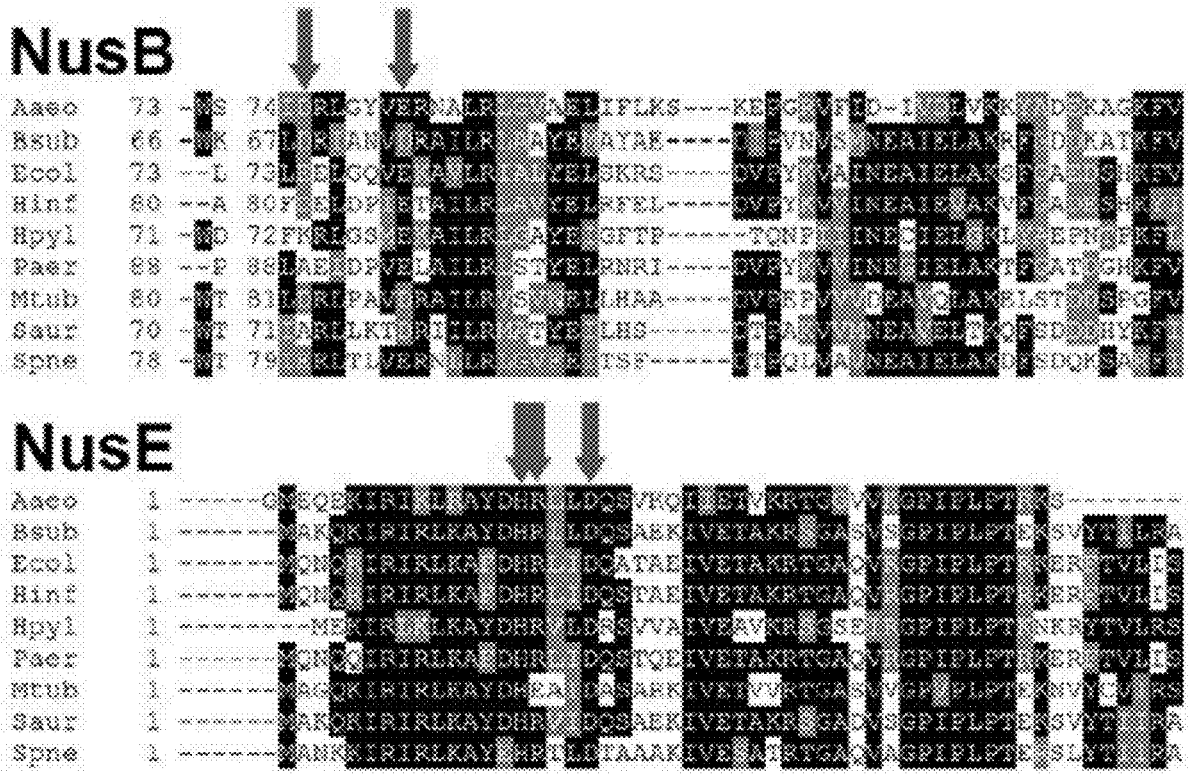
FIG. 5. Partial sequence alignments of NusB and NusE. Aaeo: *Aquifex aeolicus*; Bsub: *Bacillus subtilis*; Ecol: *Escherichia coli*; Hinf: *Haemophilus influenzae*; Hpyl: *Helicobacter pylori*; Paer: *Pseudomonas aeruginosa*; Mtub: *Mycobacterium tuberculosis*; Saur: *Staphylococcus aureus*; Spne: *Streptococcus pneumoniae*; Arrow indicates residues involved in NusB-E interaction.

Examination of the published crystal structures of the *Escherichia coli* NusB-NusE heterodimer [Protein Data Bank (PDB) entry 3D3B] (FIG. 1B)[21] reveals that NusE contains only 18% α-helix and binds with NusB mainly via interactions with helix 2 (FIG. 1B).[22] The hydrogen bonding interactions occur between NusB E81 and NusE H15, NusB Y18 and NusE D19, and NusB E75 and NusE. R16 (FIG. 1B, expanded view; *E. coli* amino acid residue numbering), which are highly conserved across prokaryotes (FIG. 5, arrows). Additionally, a nuclear magnetic resonance study of the *Aquifex aeolicus* NusB-NusE interaction also confirmed similar interactions exist in solution.[23]

Figure 2A:
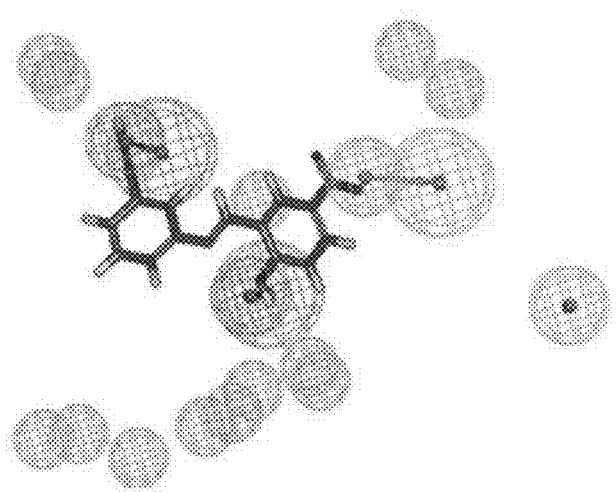

The structural information about the NusB-NusE heterodimer co-crystal (PDB entry 3D3B)[22] was used to develop a pharmacophore model (FIG. 2A). The pharmacophore model comprised two hydrogen donors (pink), one acceptor (green) to mimic the major hydrogen bonds between NusB and NusE as mentioned above, and one conserved hydrophobic interaction (cyan, FIG. 2A) between *E. coli* residues NusB L22 and NusE V26. In addition to the interactions, a series of exclusion zones (gray) were added to minimize steric clashes within the shallow pocket that forms the binding site on NusB. The final pharmacophore model was then created using Biovia DS4.5 to map on all the features required.[24] As the pharmacophore model was designed on the basis of the properties of the important amino acid residues on the NusE protein responsible for binding to NusB, theoretically, the ideal small molecules capable of docking into this pharmacophore model should be able to bind to NusB and demonstrate inhibitory activity against the NusB-NusE interaction accordingly.

Figure 6:
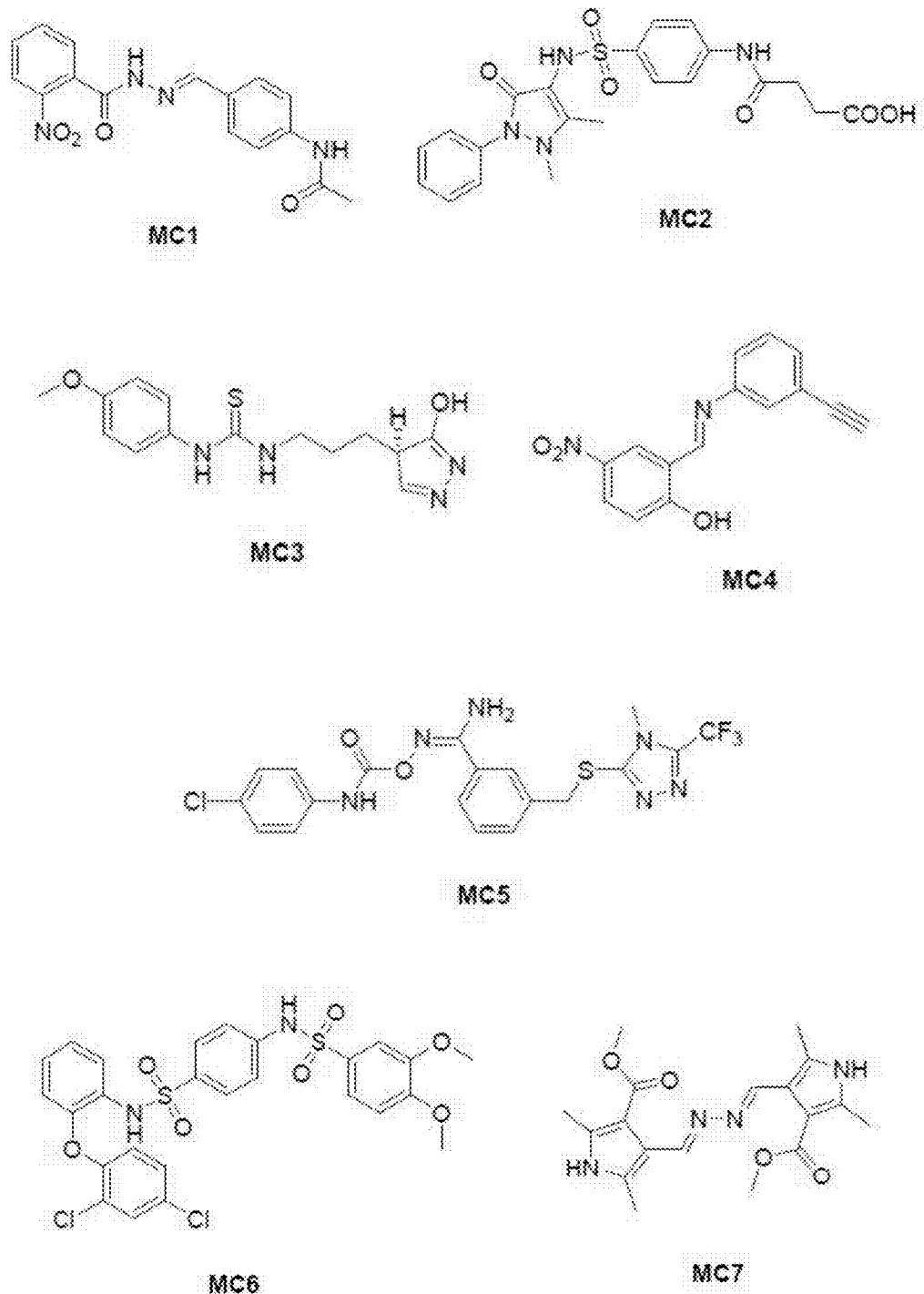
FIG. 6. Seven compounds short listed from in silico screening. MC1, N-{4-[2-(2-nitrobenzoyl)carbohydrazonoyl]phenyl}acetamide (CAS no. 679423-05-3) MC2, 3-({4-[(1,5-dimethyl-3-oxo-2-phenyl-2,3-dihydro-1H-pyrazol-4-yl)sulfamoyl]phenyl}carbamoyl)propanoic acid (CAS no. 253605-53-7); MC3, 3-[3-(3-hydroxy-4H-pyrazol-4-yl)propyl]-1-(4-methoxyphenyl)thiourea (CAS no. 656222-98-9); MC4, (E)-2-[[(3-ethynylphenyl)imino]methyl]-4-nitrophenol (CAS no. 219140-31-5); MC5, (E)-{amino[3-({[4-methyl-5-(trifluoromethyl)-4H-1,2,4-triazol-3-yl]sulfanyl}methyl)phenyl]methylidene}amino N-(4-chlorophenyl)carbamate (CAS no. 882256-39-5); MC6, N-(4-{[2-(2,4-dichlorophenoxy)phenyl]sulfamoyl}phenyl)-3,4-dimethoxybenzene-1-sulfonamide (CAS no. 312324-35-9); MC7, methyl 4-[(1E)-[(E)-2-{[4-(methoxycarbonyl)-2,5-dimethyl-1H-pyrrol-3-yl]methylidene}hydrazin-1-ylidene]methyl]-2,5-dimethyl-1H-pyrrole-3-carboxylate (CAS no. 883037-11-4).

On the basis of the pharmacophore model, an in silico screen was performed using a virtual compound library constructed by combining the mini-Maybridge library and the Enamine antibacterial library.[25] The top 50 hits from the initial virtual screen were re-mapped against the pharmacophore model and the energy-minimized conformations of compounds visually inspected. The compounds that poorly fit into the pharmacophore were removed. As a result, seven compounds (FIG. 6) were initially short-listed for wet-laboratory testing.

Figure 2B:
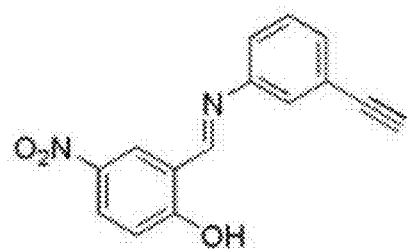
FIG. 2B. Chemical structure of (E)-2-{[3-ethynylphenyl)imino]methyl}-4-nitrophenol (MC4).
Figure 3:
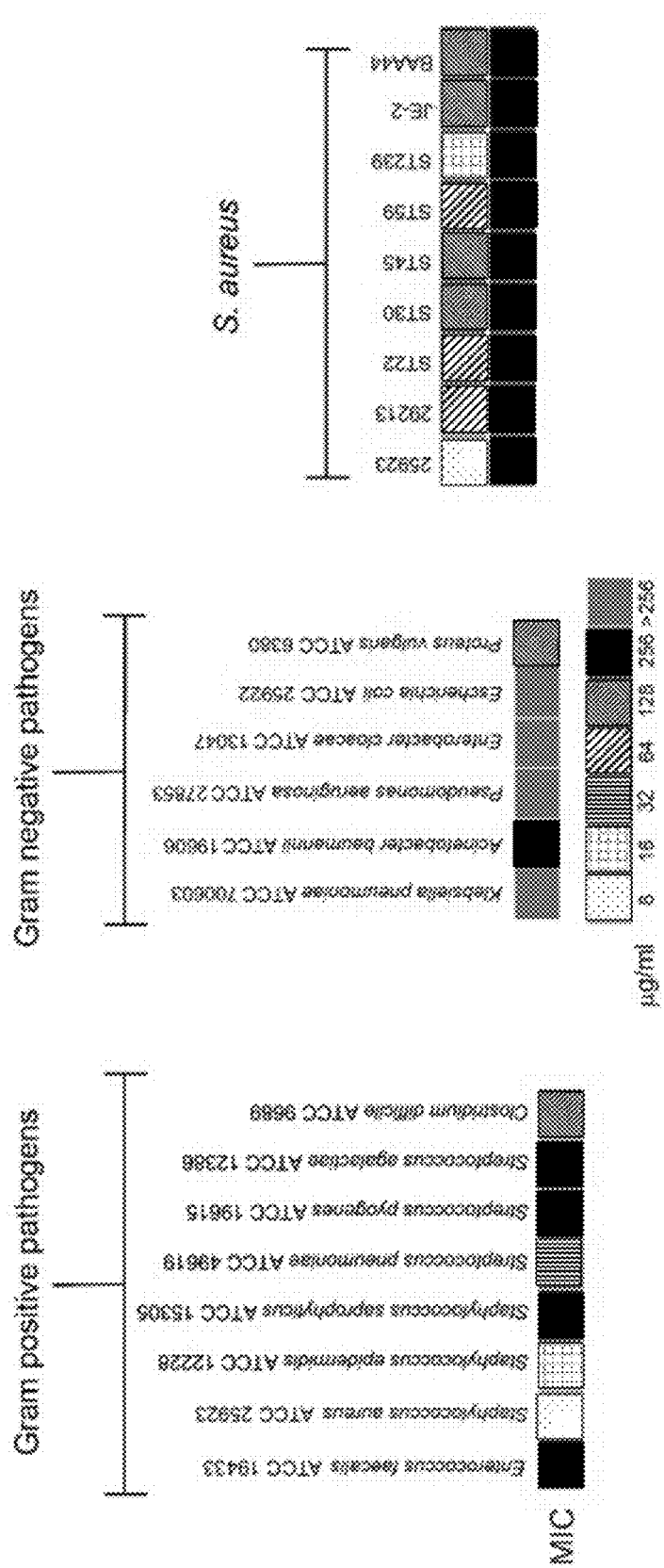
FIG. 3. Antimicrobial activity of MC4 against selected pathogenic bacteria. Abbreviations: MIC, minimum inhibitory concentration; MBC, minimum bactericidal concentration; ND, not determined.

The antimicrobial activity of the seven compounds against community-acquired MRSA strain USA300 were first screened. Of the analogues evaluated, MC4 (FIG. 2B) was found to demonstrate growth inhibition effects with a minimum inhibitory concentration (MIC) of 64 µg/mL (FIG. 3). With a molecular weight of 266.3, MC4 has been reported to be of use only to form a metal complex dye in optical layers for optical data recording.[26] The antimicrobial activities of MC4 against a panel of representative strains of pathogens were then tested. MC4 demonstrated preferred antimicrobial activity against *S. aureus* strains, including MRSA, over other pathogens tested, with MICs as low as 8 µg/mL against control strain *S. aureus* 25923 and 16 g/mL against healthcare acquired MRSA ST239 (FIG. 3). Additionally, MC4 did not show significant cytotoxicity against mammalian cell lines compared to 5-fluorouracil (Table 1).

Figure 4:
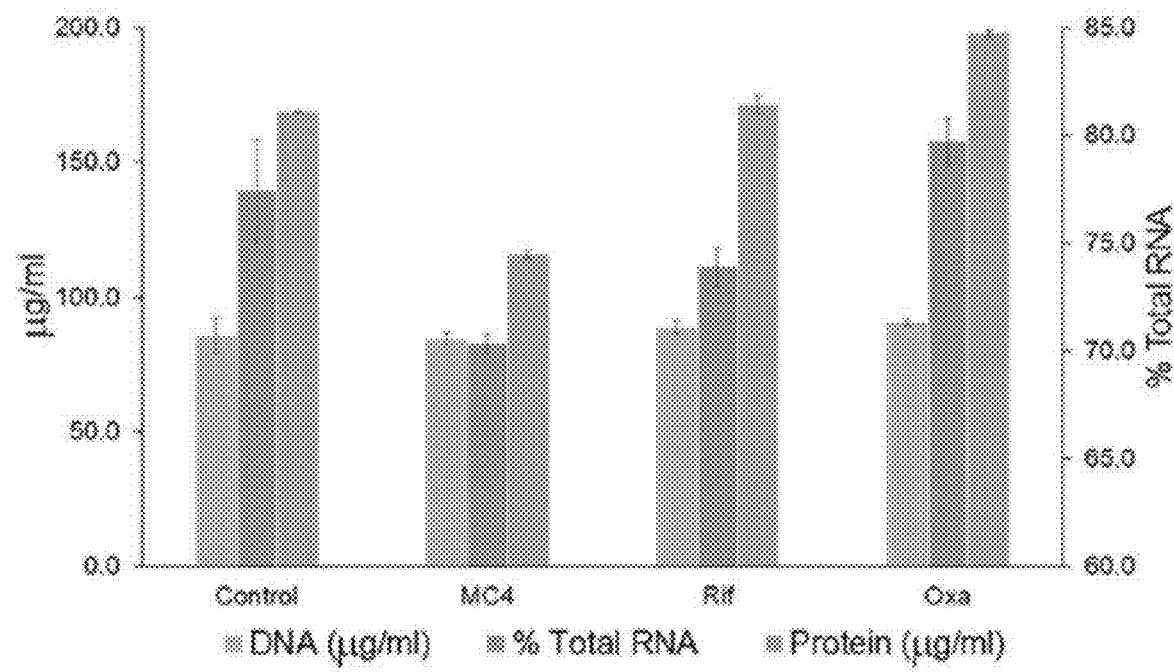
FIG. 4. Effects of MC4, rifampicin (Rif), and oxacillin (Oxa) at one-quarter minimum inhibitory concentrations (MICs) on DNA, rRA (16S+23S), and protein production in *S. aureus* 25923 cells.

The level of macromolecules in *S. aureus* ATCC 25923 cells during exponential growth due to MC4 treatment were analyzed. MC4, rifampicin, and oxacillin were added at a one-quarter MIC level, which did not interfere with the rate of growth of *S. aureus* ATCC 25923 cells. As shown in FIG. 4, none of the treatment affected the DNA level, as previewed by the mode of action. In the control cells, the level of major rRNA (16S+23S) was around 78% of total RNA (FIG. 4).[4] Rifampicin resulted in reduction in the rRNA level consistent with previous observations (FIG. 4).[27] MC4 showed a significant reduction in the rRNA level, which was lower than that of rifampicin treated cells (FIG. 4). Furthermore, MC4 treatment led to a significant reduction in the protein level, while rifampicin did not show this effect, probably as a result of a decreased level of ribosome production, affecting the protein synthesis ability. Oxacillin-treated cells displayed rRNA and protein production levels slightly higher than those of control cells.

Figure 7:
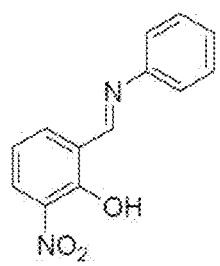
FIG. 7. Ten analogues of MC4. MC4-1, 2-nitro-6-[(E)-(phenylimino)methyl]phenol (CAS no. 243981-87-5); MC42, 2-{1[(1E)-(2-hydroxy-3-nitrophenyl)methylene]amino}-4-methylphenol (CAS no. 321726-90-3); MC4-3, 1-(3-{[(1E)-(2-hydroxy-5-nitrophenyl)methylene]amino}phenyl)ethanone (CAS no. 316133-49-0); MC4-4, 4-nitro-2-[(phenylimino)methyl]phenol (CAS no. 15667-99-9); MC4-5, 2-{(E)-[(3-methylphenyl)imino]methyl}-4-nitrophenol (CAS no. 303058-73-3); MC4-6, 2-{(E)-[(4-hydroxyphenyl)imino]methyl}-4-nitrophenol (CAS no. 1081780-22-4); MC4-7, 2-{(E)-[(4-chlorophenyl)imino]methyl}-4-nitrophenol (CAS no. 303215-49-8); MC4-8, 2-{(E)[(3-hydroxyphenyl)imino]methyl}-4-nitrophenol (CAS no. 303215-19-2).
Figure 7:
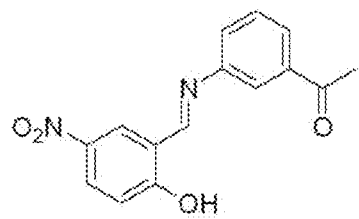
Figure 7:
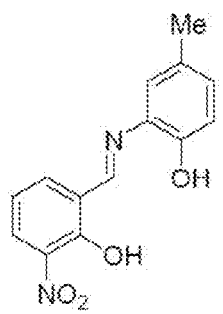
Figure 7:
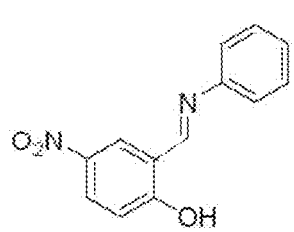
Figure 7:
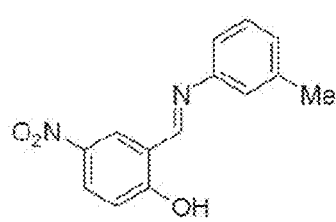
Figure 7:
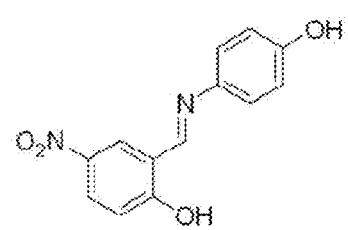
Figure 7:
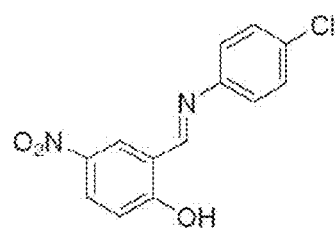
Figure 7:
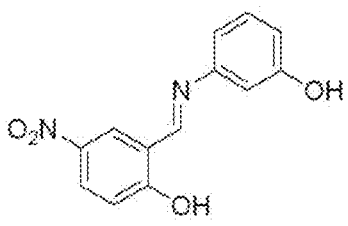

Finally, to establish MC4's mode of action at the molecular level, an enzyme-linked immunosorbant assay-based inhibitory assay was performed to assess the in vitro inhibition of NusB-NusE heterodimer formation by MC4.[24] Purified NusB was used to coat the 96-well plate, and GST-tagged NusE was used as the probe. MC4 showed positive inhibition of the NusB-NusE interaction with an IC50 of ~34.7±0.13 µM. By further testing a series of MC4 analogues (FIG. 7), it was found that three functional groups on the molecule targeting interactions between NusB E81 and NusE H15, NusB Y18 and NusE D19, and NusB E75 and NusE R16 were compulsory for inhibiting NusB-NusE binding, as predicted by FitScore of Biovia DS4.5 (Table 3). With the change in the phenyl acetylene group to phenols, the IC50 values of the corresponding MC4 analogues increased, while deletion of this terminal triple bond or replacing by methyl or chloride caused a reduced IC50. When p-nitrophenol was modified to o-nitrophenol, the IC50 values increased, probably because of the involvement of the phenol group in the binding interaction with NusB Y81 (Table 3). These results confirmed the pharmacophore model used in this invention and demonstrated that the reactivity of imine and p-nitrophenol did not contribute to the activity of MC4.

Figure 8A:
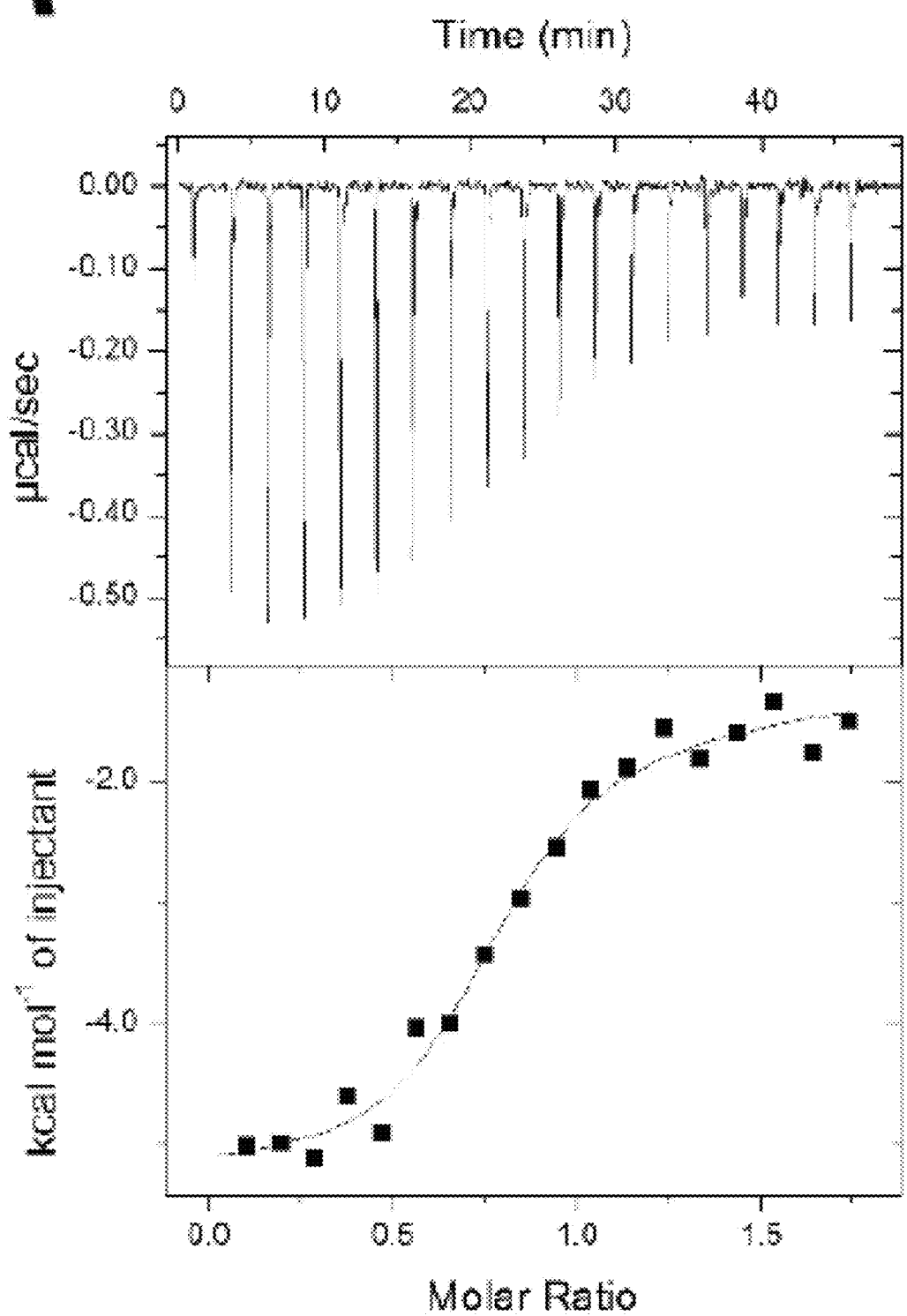
FIGS. 8A-8D. Isothermal titration calorimetry assay using MC4 and *B. subtilis* NusB wild type protein (FIG. 8A) and variants Y18A, D76A, D81A (FIG. 8B-8D, respectively), wherein N=0.988±0.076, Kd=1.45±0.55 µM, ΔH=−7141±939.8 cal/mol, and ΔS=−1.81 cal/mol/deg.
Figure 8B:
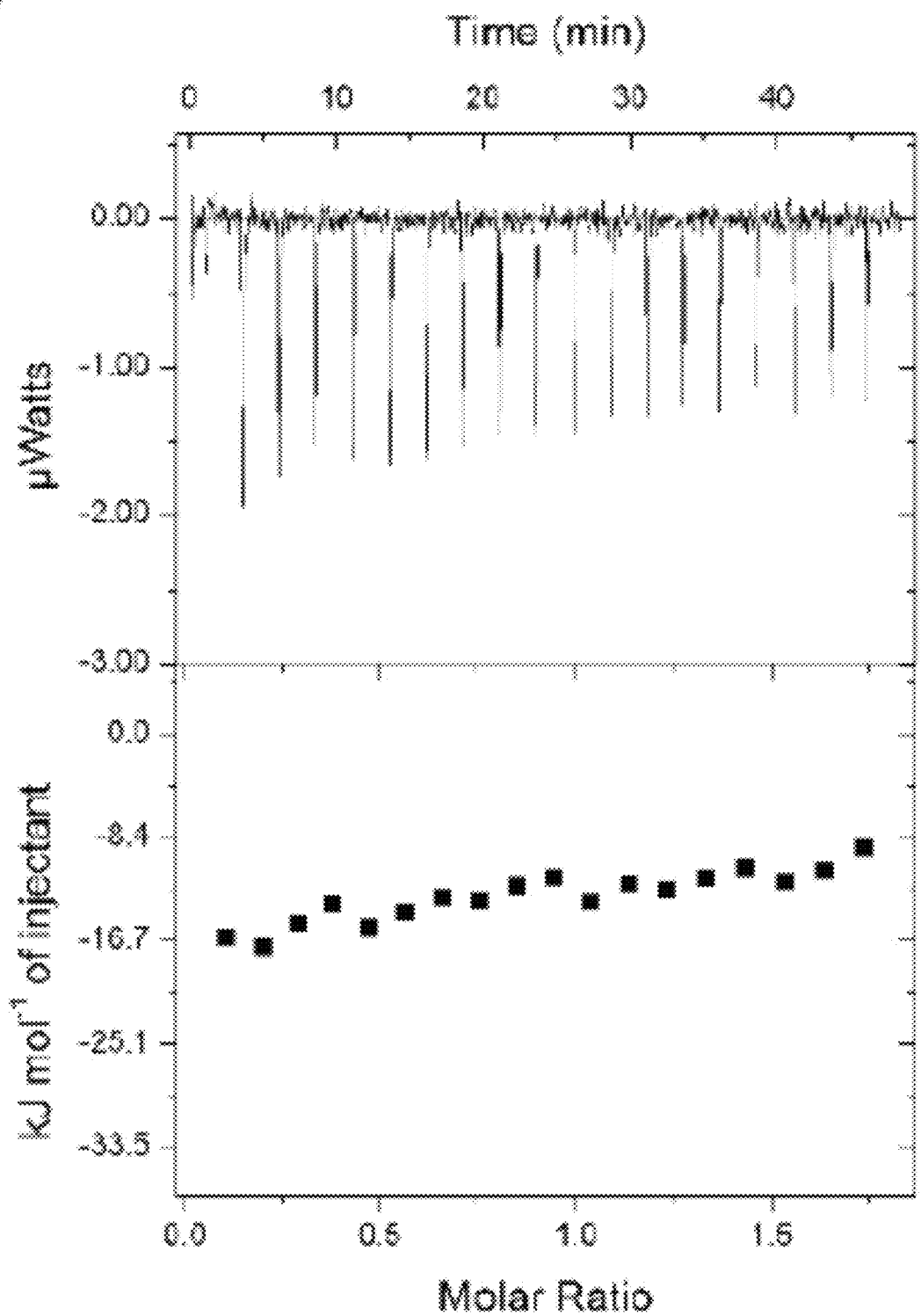
Figure 8C:
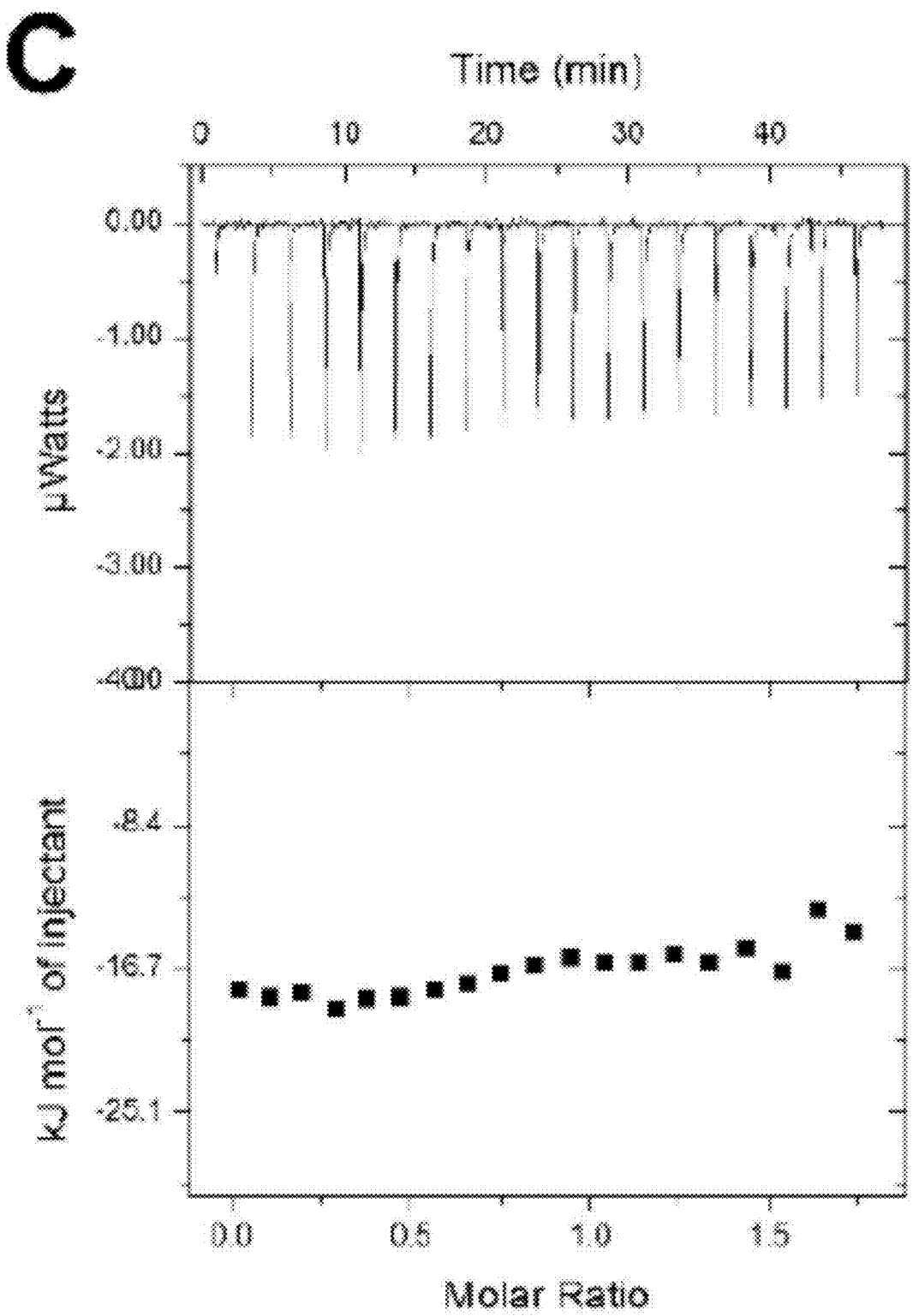
Figure 8D:
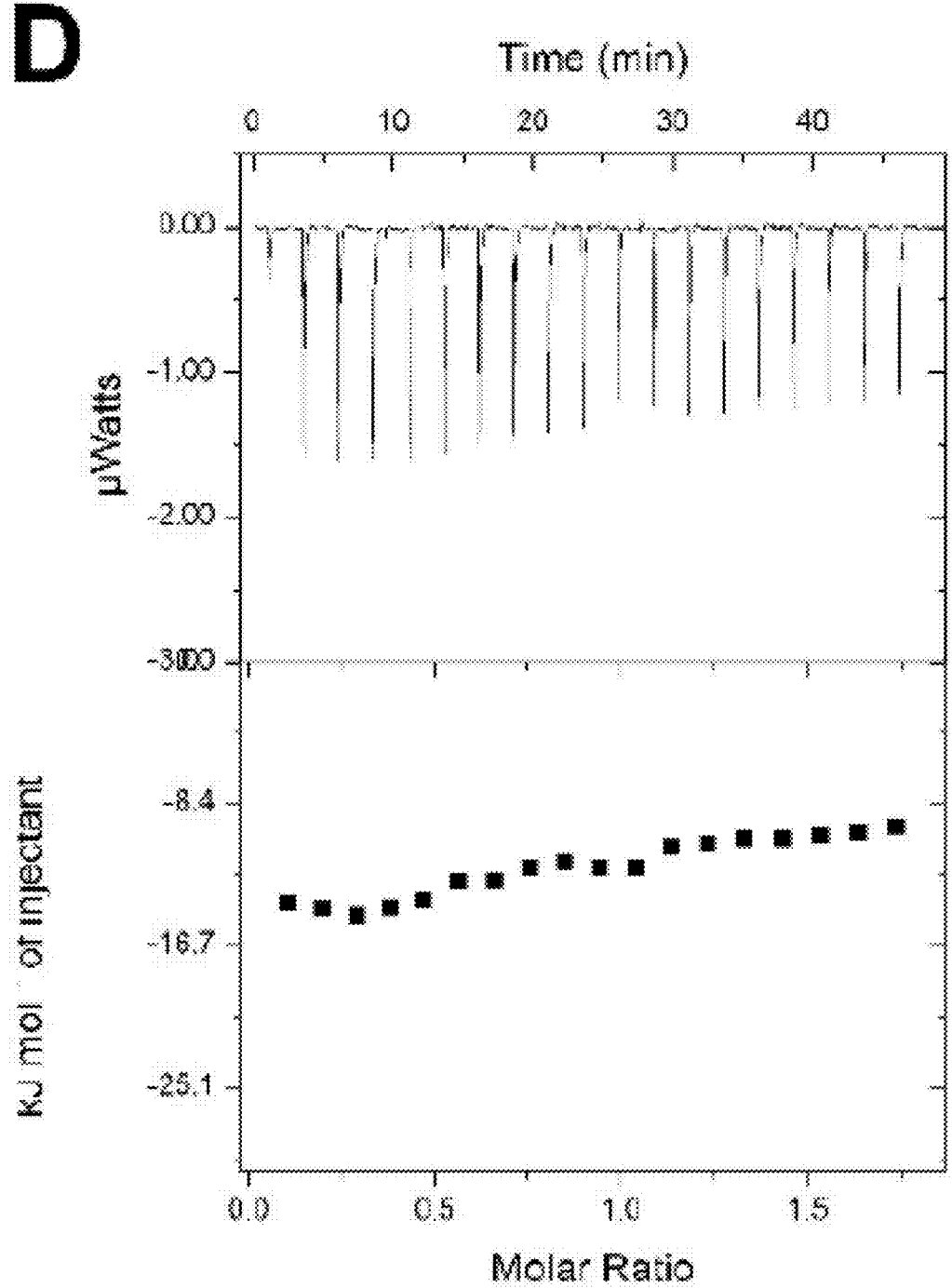

The interaction between MC4 and NusB was also biophysically quantified. A previous report demonstrated that NusB bound to NusE in a 1:1 ratio with a Kd of ~1 µM as determined by isothermal titration calorimetry (ITC).[21] In similar experiments, it was found that MC4 bound specifically to NusB (FIG. 8A) with a one-site binding mode with a Kd of 1.45±0.55 µM. Binding of MC4 to NusE could not be detected by ITC (not shown), or between MC4 and NusB variants (Y18A, D76A, and D81A) with the three amino acid residues responsible for NusE binding altered to alanine (FIG. 8B-D). These results together suggest the inhibition of NusB-NusE heterodimer formation is achieved via specific interaction between MC4 and NusB as designed. Further experiments will be performed to resolve the structure of NusB in complex with MC4 for target validation, as well as structure-based lead optimization.

The potential impact of untreatable antibiotic-resistant infections on society is profound, and there is an urgent need to identify new drug targets.[28] Traditionally, the bacterial ribosome itself (both 30S and 50S subunits) has been one of the most commonly exploited targets for antibiotics inhibiting protein synthesis.[29] Recent drug discovery research had validated the finding that inhibition of rescuing stalled ribosomes at the end of mRNAs resulted in antibacterial activity.[30] Given the ribosome is positively related to fast growth/proliferation and the large difference between eukaryotic and prokaryotic rRNA transcription machinery, it is tempting to hypothesize inhibition of rRNA synthesis would be expected to have a major impact on cell growth and/or viability. This hypothesis is strengthened by recent findings showing that many anticancer drugs inhibit rRNA synthesis or maturation.[31]

In this work, pharmacophore-based in silico screening followed by biological confirmation was used for identifying a potential new antibiotic lead. An essential interaction between transcription factors NusB and NusE that is required for the formation of highly processive complexes used for the synthesis of rRNA within bacterial cells was targeted. One of the short-listed compounds (MC4) showed specific activity against *S. aureus* strains, including MRSA, without significant toxicity to mammalian cell lines. This compound is like the first designed to target bacterial rRNA synthesis that has antimicrobial activities. The detailed effect of MC4 in rRNA transcription/processing, ribosome biogenesis, and *S. aureus* virulence is currently under investigation. Although MC4 has been shown to specifically inhibit NusB-NusE interaction at the molecular level, any potential off-target effect on bacterial cells remains to be elucidated. Because NusB and NusE are highly conserved in bacteria, the reason that MC4 has preferred antimicrobial activity against *S. aureus* over other pathogens needs to be further investigated.

An essential protein-protein interaction between transcription factors in the bacterial rRNA synthesis machinery as a novel antimicrobial target was validated. Other important protein-protein interactions involved in bacterial rRNA transcription, e.g., between NusE and NusG, the NusE-RNA polymerase complex might also have the potential as novel antimicrobial targets.[32] This work paves the way for the structural optimization of MC4, and potentially other compounds from more comprehensive screens, for development as prospective new antimicrobial lead molecules targeting bacterial rRNA synthesis.

Materials and Methods

Bacterial Strains and Chemicals. The following bacterial strains were used in this study for the microdilution assay: *Enterococcus faecalis* ATCC 29212, *Klebsiella pneumonia* ATCC 700603, *Acinetobacter baumannii* ATCC 19606, *Pseudomonas aeruginosa* PA01, *Enterobacter cloacae* ATCC 13047, *E. coli* ATCC 25922, *Proteus vulgaris* ATCC 6380, and *S. aureus* USA300, ATCC 25923, ATCC 29213, ST22, ST30, ST45, ST59, ST239, JE-2, BAA44. *E. coli* strain DH5a (Gibco BRL) was used in this study for cloning and BL21 (DE3) pLysS[23] was used for protein overproduction. 5-fluorouracil, rifampicin and other antibiotics used in the microdilution assay were purchased from SigmaAldrich. Compounds MC1-7 were purchased from MolPort.

Molecular modeling. The antitermination complex model was constructed by consolidating a number of published crystal structures, including the *Thermus thermophilus* transcription elongation complex (PDB: 2O5I),[34] *E. coli* RNA polymerase-NusG complex (PDB: 5 tbz),[35] *Aquifex aeolicus* NusB-E in complex with boxA RNA (PDB: 3R2C), *Myco-* bacterium tuberculosis NusA C-terminal domain-RNA complex (PDB: 2ASB);[37] as well as the NMR solution structure of E. coli NusE:NusG-CTD complex (PDB: 2KVQ),[38] and B. subtilis NusA N-terminal domain (PDB: 2MT4).[39] Structure matching was performed using the MatchMaker function of UCSF Chimera.[40] Images were generated with UCSF Chimera.

Pharmacophore design and virtual screening were performed as described previously.[41]

Antibacterial activity test. Microdilution assay was performed according to the Clinical & Laboratory Standards Institute recommendations.[42] Serial 2-fold dilutions of the tested compounds and antibiotic controls were made from 256 µg/ml to 0.5 µg/ml. DMSO was included as a negative control.

Cytotoxicity assay was performed as detailed previously[43] except A549 lung carcinoma and HaCaT immortalized human keratinocytes were used in this study.

DNA, protein and rRNA quantitation. MC4, oxacillin and rifampicin at ¼ MIC level were added to S. aureus strain ATCC 25923 in LB medium at early log phase (OD595=0.2), which was then grown to mid-log phase (OD595=0.5). For DNA and protein quantitation, 1 ml cells were harvested and treated with 10 mg/ml lysozyme+ 0.5 mg/ml lysostaphin at RT for 1 hr before centrifugation at 13000 g/min for 3 min. The supernatant was discarded and cells lysed with 600 µl Nuclei Lysis Solution (Promega/ Genomic DNA Purification Kit) for 5 min, followed by gentle sonication. The amount of DNA was quantified with Qubit dsDNA BR (broad range) and protein quantified with NanoOrange™ Protein Quantitation Kit (ThermoFisher). For rRNA quantitation, 1 ml culture was collected and treated with RNAProtect (Qiagen), before total RNA was extracted with an RNeasv Mini Kit (Qiagen). DNase I treatment was performed with a TURBO DNA-free Kit (ThermoFisher). The extracted RNA was subjected to Agilent 2100 analysis, and the level of major rRNA (the sum of 16S+23S rRNA) as percentage of total RNA. The values were compared across each treatment group. All experiments were repeated three times.

Plasmid Construction. All of the cloning steps were carried out in E. coli DH5α. The plasmids used and constructed in this work were confirmed by DNA sequencing, and are listed in Table 2. B. subtilis nusB was amplified using primers 5'-AAAGGAGATCTAGACATGAA AGAAGA-3' (SEQ ID NO: 1) and 5'TTTTCTGGTACCC-TATGATT CCC-3'AMD (SEQ ID NC: 2) from purified B. subtilis chromosomal DNA. The nusB mutants were made by PCR splicing[44] using mutant primers 5'-CTT CAGGCA-CIAgc 5'-CTTTGCAGGCACTAgcTCA AATTGATGTC-3' (SEQ ID NO: 3) and 5' GACATCAATTTGAgcTAGTG CCTGCAAAG-3' (SEQ ID NO: 4), 5'-GAATTG-GAAGCTCGATgcGATTGCCAATG-3' (SEQ ID NO: 5) and 5'-CATTGGCAATCgcATCGA GCTTCCAATTC-3' (SEQ ID NO: 6), and 5'GATTGCCAATGTTGCCCGTG CGATTTTGC-3' (SEQ ID NO: 7) and 5'-GCAAAATCGCACGGgCAAC ATTGGCAATC-3' (SEQ ID NO: 8) The amplicons were cut with XbaI and Acc65I and inserted into similarly cut pETMCSIII (Table 2) to produce pNG130, pNG1178, pNGi79, and pNl1180 respectively (Table 2). B. subtilis nusE was amplified using primers 5'-AAGGAGGGTCTAGAATGGCAAAAC-3' (SEQ ID NO: 9) and 5' CTATATTTTAGGTACCAAGT TTAATTT-3' (SEQ ID NO: 10) from B. subtilis chromosomal DNA and ligated into the NdeI and Acc65I sites of pNG651 to give pNG896 (Table 2).

Protein overproduction and purification. B. subtilis NusB (wild type and mutant) and NusE-GST were overproduced from plasmids (Table 2) and purified using a similar approach to that described previously.[45] Purified proteins were dialyzed into 20 mM KH2PO4, 150 mM NaCl, 30% glycerol, pH 7.8 and stored at 80° C.

ELISA-based assays. These assays were performed as described previously,[41] except NusB was used to coat the NUNC MaxiSorp™ 96-well plates and GST-tagged NusE used as the probe.

Isothermal calorimetric titration (ITC). ITC experiments were performed as described previously.[41] For compound testing, a 50 mM stock made up in DMSO was diluted to 500 µM in ITC buffer (50 mM KH2PO4, 150 mM NaCl, pH 7.4). All proteins were dialysed into ITC buffer and were supplemented with the same concentration of DMSO (1% v/v) to minimize buffer miss-match. MC4 was then titrated against 50 µM NusB wild type and mutants as described previously[41] using 1% DMSO in ITC buffer as the negative control.

TABLE I

Cytotoxicity (CC50) of MC4 against human cell lines.

| | Cell line | |
| --- | --- | --- |
| Treatment | A549 lung carcinoma | HaCaT immortalized human keratinocytes |
| 5-fluorouracil | 5.62 ± 0.002 nM | <1 nM |
| MC4 | 183.33 ± 7.71 µM | 695.15 ± 5.95 µM |

TABLE 2

Strains and plasmids used and created in this study.

| Plasmids | Genotype | Source/Construction |
| --- | --- | --- |
| Vectors for cloning | | |
| pETMCSIII | bla P$\varphi_{10}$-6xHis-T$\varphi$ | [46] |
| pNG651 | bla P$\varphi_{10}$-3CGST-T$\varphi$ | [47] |
| Vectors for protein overproduction | | |
| pNG130 | bla P$\varphi_{10}$-6His-nusB-T$\varphi$ | This work. nusB cloned into XbaI and Acc65I cut pETMCSIII |
| pNG134 | bla P$\varphi_{10}$-6His-nusE-T$\varphi$ | This work. nusE cloned into XbaI and Acc65I cut pETMCSIII |
| pNG896 | bla P$\varphi_{10}$-nusE-3CGST-T$\varphi$ | This work. nusE cloned into NdeI and Acc65I cut pNG651 |
| pNG1178 | Bla P$\varphi_{10}$-6xHis-nusB$_{(F15A)}$-T$\varphi$ | This work. nusB$_{(F15A)}$ cloned into XbaI and Acc65I cut pETMCSIII |
| pNG1179 | blaP$\varphi_{10}$-6xHis-nusB$_{(R70A)}$-T$\varphi$ | This work. nusB$_{(R70A)}$ cloned into XbaI and Acc65I cut pETMCSIII |
| pNG1180 | bla P$\varphi_{10}$- 6xHis-nusB$_{(D75A)}$-T$\varphi$ | This work. nusB$_{(D75A)}$ cloned into XbaI and Acc65I cut pETMCSIII | bla, cat, ampicillin and chloramphenicol resistance gene; P$\varphi_{10}$, phage T7 promoter; P$_{xyl}$, xylose inducible promoter, T$_\phi$, T7 transcription terminator; 3C, the recognition sequence of 3C protease; GFP green florescence protein; GST, Glutathione S-transferase; PKA, protein kinase A recognition site.

TABLE 3

Comparison of MC4 and analogues in predicted properties and IC$_{50}$.

| | IC50 (µM) | FitScore[a] | AlogP[a] | PSA-2D[a](Å) |
|---|---|---|---|---|
| MC4 | 34.7 ± 0.13 | 2.638 | 4.206 | 74.961 |
| MC4-1 | 14.4 ± 2.59 | NA[b] | 3.078 | 74.961 |
| MC4-2 | 38.2 ± 8.78 | NA[b] | 2.818 | 92.262 |
| MC4-3 | 5.94 × 10$^{-3}$ ± 1.80 | NA[b] | 3.323 | 95.777 |
| MC4-4 | 147 ± 17.9 | NA[b] | 3.078 | 74.961 |
| MC4-5 | 971 ± 11.6 | NA[b] | 3.565 | 74.961 |
| MC4-6 | 8.15 × 10$^{-3}$ ± 1.68 | 2.569 | 2.836 | 95.777 |
| MC4-7 | 1639 ± 12.7 | NA[b] | 3.743 | 74.961 |
| MC4-8 | 6.92 × 10$^{-3}$ ± 0.68 | 2.460 | 2.836 | 95.777 |

[a]Biovia DS4.5 calculation;
[b]No FitScore provided by the software

Example 2

Mc4 Analogues

The structures of further MC4 analogues are presented below with their minimum inhibitory concentrations on 9 microorganisms are shown in FIG. 9 (EFAE 19433: *Enterococcus faecalis* ATCC 19433:SAUR 25923: *Staphylococcus aureus* ATCC 25923; SAUR 29213; *Staphylococcus aureus* ATCC 29213; KPNE 700603: *Klebsiella pneumoniae* ATCC 700603; ABAU 19606: *Acinetobacter baumannii* ATCC 19606; PAER 27853: *Pseudomonas aeruginosa* AFCC 27853; ECLO 13047: *Enterobacter cloacae* ATCC 13047; ECOL 25922: *Escherichia coli* ATCC 25922; SPNE 49619: *Streptococcus pneumoniae* ATCC 49619).

The antimicrobial activity of the compounds was determined by broth microdilution according to the CLSI guidelines (1). The test medium was cation-adjusted Mueller-Hinton broth (MH). Serial two-fold dilutions were performed for the tested chemicals starting from 256 µg/ml to 0.0625 µg/ml, and the bacterial cell inoculum was adjusted to approximately 5×105 CFU per ml. Results were taken after 20 h of incubation at 37° C. MIC was defined as the lowest concentration of antibiotic with no visible growth. Experiments were performed in duplicates.

| No. | Structure | Formula | Mol. Wt |
|---|---|---|---|
| MC4-1 | 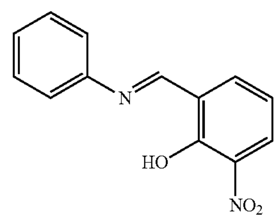 [SMILES: O=[N+]([O-])c1cccc(/C=N/c2ccccc2)c1O] | $C_{13}H_{10}N_2O_3$ | 242.23 |
| MC4-2 | 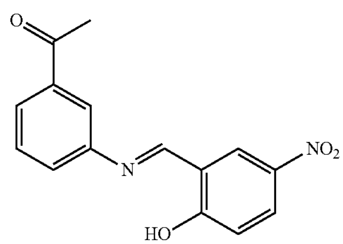 [SMILES: CC(=O)c1cccc(/N=C/c2cc([N+](=O)[O-])ccc2O)c1] | $C_{15}H_{12}N_2O_4$ | 284.27 |
| MC4-3 | 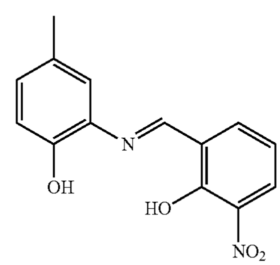 [SMILES: Cc1ccc(O)c(/N=C/c2cccc([N+](=O)[O-])c2O)c1] | $C_{14}H_{12}N_2O_4$ | 272.26 |
| MC4-11 | 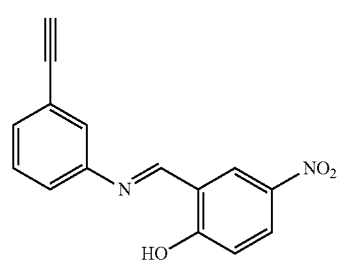 [SMILES: C#Cc1cccc(/N=C/c2cc([N+](=O)[O-])ccc2O)c1] | $C_{15}H_{10}N_2O_3$ | 266.26 |

| No. | Structure | Formula | Mol. Wt |
|---|---|---|---|
| MC4-12 | 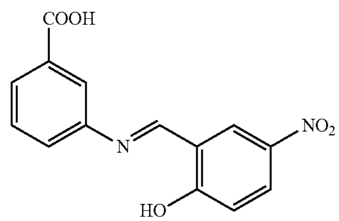 [SMILES: O=C(O)c1cccc(/N=C/c2cc([N+](=O)[O-])ccc2O)c1] | $C_{14}H_{10}N_2O_5$ | 286.24 |
| MC4-13 | 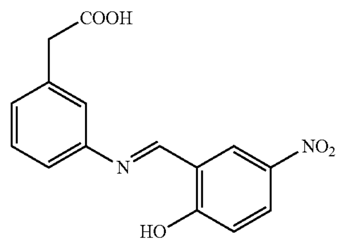 [SMILES: O=C(O)Cc1cccc(/N=C/c2cc([N+](=O)[O-])ccc2O)c1] | $C_{15}H_{12}N_2O_5$ | 300.27 |
| MC4-14 | 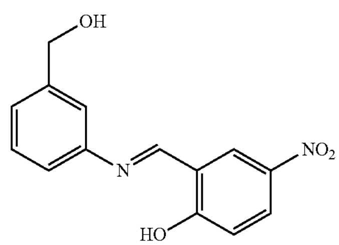 [SMILES: O=[N+]([O-])c1ccc(O)c(/C=N/c2cccc(CO)c2)c1] | $C_{14}H_{12}N_2O_4$ | 272.26 |
| MC4-15 | 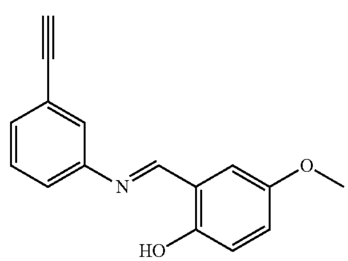 [SMILES: C#Cc1cccc(/N=C/c2cc(OC)ccc2O)c1] | $C_{16}H_{13}NO_2$ | 251.29 |
| MC4-16 | 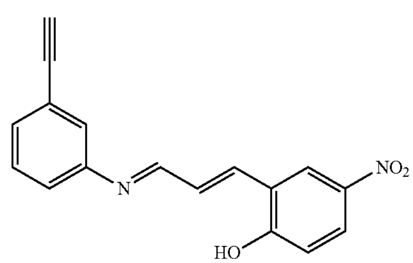 [SMILES: C#Cc1cccc(/N=C/C=C/c2cc([N+](=O)[O-])ccc2O)c1] | $C_{17}H_{12}N_2O_3$ | 292.29 |
| MC4-17 | 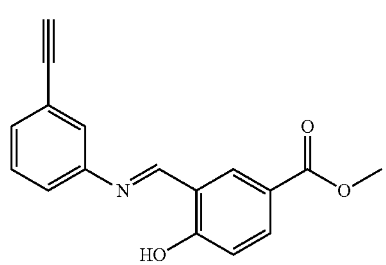 [SMILES: C#Cc1cccc(/N=C/c2cc(C(=O)OC)ccc2O)c1] | $C_{17}H_{13}NO_3$ | 279.30 |

| No. | Structure | Formula | Mol. Wt |
|---|---|---|---|
| MC4-18 | 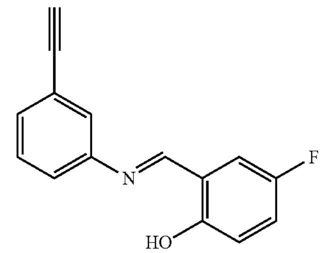 [SMILES: C#Cc1cccc(/N=C/c2cc(F)ccc2O)c1] | C₁₅H₁₀FNO | 239.25 |
| MC4-19 | 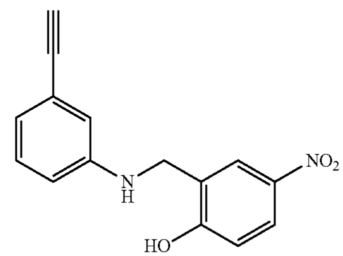 [SMILES: C#Cc1cccc(NCc2cc([N+](=O)[O-])ccc2O)c1] | C₁₅H₁₂N₂O₃ | 268.27 |
| MC4-20 | 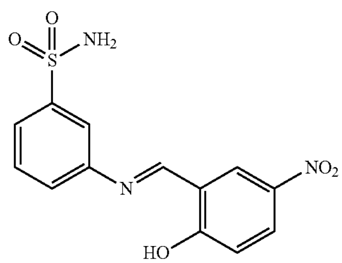 [SMILES: NS(=O)(=O)c1cccc(/N=C/c2cc([N+](=O)[O-])ccc2O)c1] | C₁₃H₁₁N₃O₅S | 321.31 |
| MC4-21 | 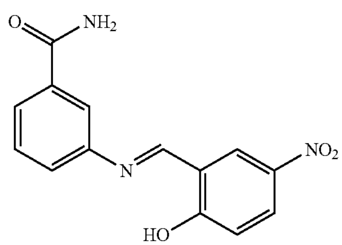 [SMILES: NC(=O)c1cccc(/N=C/c2cc([N+](=O)[O-])ccc2O)c1] | C₁₄H₁₁N₃O₄ | 285.26 |
| MC4-22 | 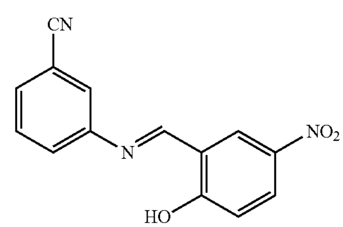 [SMILES: N#Cc1cccc(/N=C/c2cc([N+](=O)[O-])ccc2O)c1] | C₁₄H₉N₃O₃ | 267.24 |
| MC4-23 | 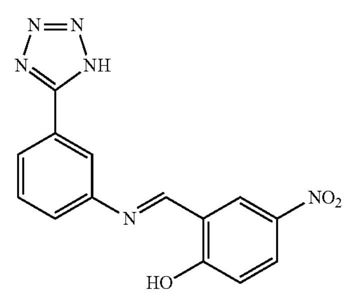 [SMILES: O=[N+]([O-])c1ccc(O)c(/C=N/c2cccc(-c3nnn[nH]3)c2)c1] | C₁₄H₁₀N₆O₃ | 310.27 |

-continued

| No. | Structure | Formula | Mol. Wt |
|---|---|---|---|
| MC4-24 | 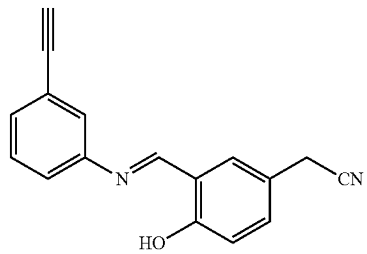 [SMILES: C#Cc1cccc(/N=C/c2cc(CC#N)ccc2O)c1] | $C_{17}H_{12}N_2O$ | 260.30 |
| MC4-25 | 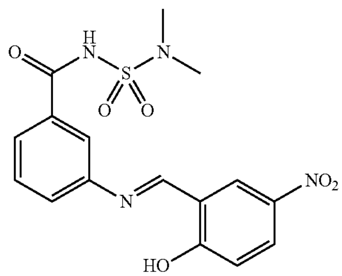 [SMILES: CN(C)S(=O)(=O)NC(=O)c1cccc(/N=C/c2cc([N+](=O)[O-])ccc2O)c1] | $C_{16}H_{16}N_4O_6S$ | 392.39 |
| MC4-26 | 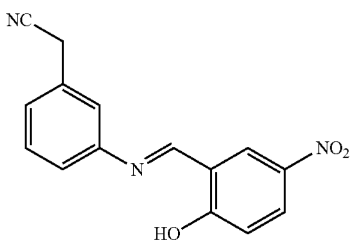 [SMILES: N#CCc1cccc(/N=C/c2cc([N+](=O)[O-])ccc2O)c1] | $C_{15}H_{11}N_3O_3$ | 281.27 |
| MC4-27 | 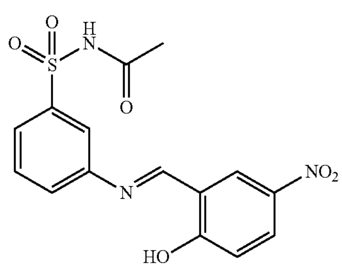 [SMILES: CC(=O)NS(=O)(=O)c1cccc(/N=C/c2cc([N+](=O)[O-])ccc2O)c1] | $C_{15}H_{13}N_3O_6S$ | 363.34 |
| MC4-28 | 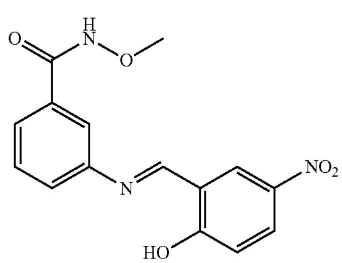 [SMILES: CONC(=O)c1cccc(/N=C/c2cc([N+](=O)[O-])ccc2O)c1] | $C_{15}H_{13}N_3O_5$ | 315.29 |
| MC4-29 | 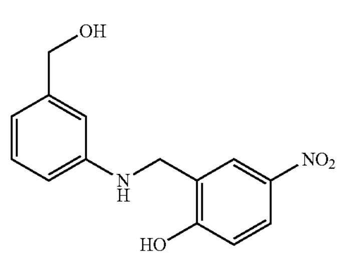 [SMILES: O=[N+]([O-])c1ccc(O)c(CNc2cccc(CO)c2)c1] | $C_{14}H_{14}N_2O_4$ | 274.28 |

-continued

| No. | Structure | Formula | Mol. Wt |
|---|---|---|---|
| MC4-30 | 3-[(2-hydroxy-5-nitrobenzyl)amino]benzoic acid | C₁₄H₁₂N₂O₅ | 288.26 |
| MC4-31 | 2-{3-[(2-hydroxy-5-nitrobenzyl)amino]phenyl}acetic acid | C₁₅H₁₄N₂O₅ | 302.29 |
| MC4-32 | 2-[(3-ethynylphenyl)aminomethyl]-4-methoxyphenol | C₁₆H₁₅NO₂ | 253.30 |
| MC4-33 | methyl 3-[(3-ethynylphenyl)aminomethyl]-4-hydroxybenzoate | C₁₇H₁₅NO₃ | 281.31 |
| MC4-34 | 2-[(3-ethynylphenyl)aminomethyl]-4-fluorophenol | C₁₅H₁₂FNO | 241.27 |
| MC4-35 | 3-{[(2-hydroxy-5-nitrobenzyl)amino]}benzenesulfonamide | C₁₃H₁₃N₃O₅S | 323.32 |

-continued

| No. | Structure | Formula | Mol. Wt |
|---|---|---|---|
| MC4-36 | 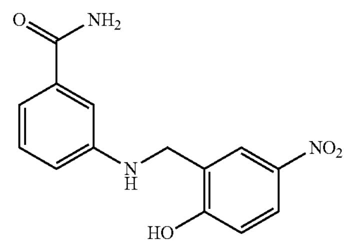 [SMILES: NC(=O)c1cccc(NCc2cc([N+](=O)[O-])ccc2O)c1] | C$_{14}$H$_{13}$N$_3$O$_4$ | 287.28 |
| MC4-37 | 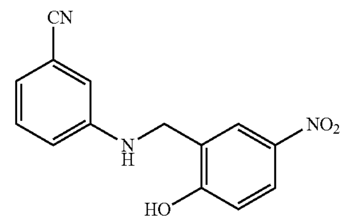 [SMILES: N#Cc1cccc(NCc2cc([N+](=O)[O-])ccc2O)c1] | C$_{14}$H$_{11}$N$_3$O$_3$ | 269.26 |
| MC4-38 | 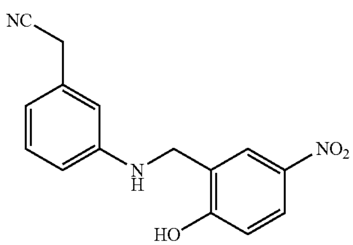 [SMILES: N#CCc1cccc(NCc2cc([N+](=O)[O-])ccc2O)c1] | C$_{15}$H$_{13}$N$_3$O$_3$ | 283.29 |
| MC4-39 | 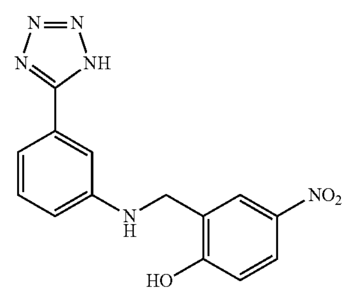 [SMILES: O=[N+]([O-])c1ccc(O)c(CNc2cccc(-c3nnn[nH]3)c2)c1] | C$_{14}$H$_{12}$N$_6$O$_3$ | 312.29 |
| MC4-40 | 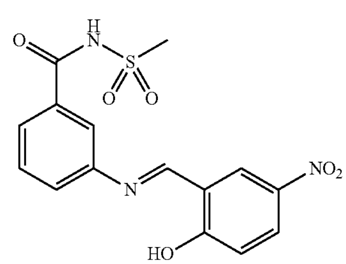 [SMILES: CS(=O)(=O)NC(=O)c1cccc(/N=C/c2cc([N+](=O)[O-])ccc2O)c1] | C$_{15}$H$_{13}$N$_3$O$_6$S | 363.34 |
| MC4-41 | 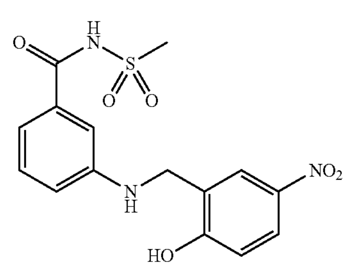 [SMILES: CS(=O)(=O)NC(=O)c1cccc(NCc2cc([N+](=O)[O-])ccc2O)c1] | C$_{15}$H$_{15}$N$_3$O$_6$S | 365.36 |

-continued

| No. | Structure | Formula | Mol. Wt |
|---|---|---|---|
| MC4-42 | 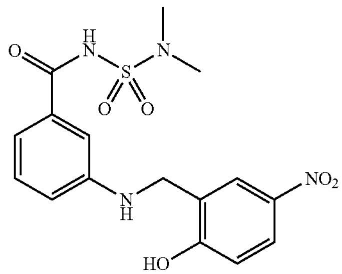 [SMILES: CN(C)S(=O)(=O)NC(=O)c1cccc(NCc2cc([N+](=O)[O-])ccc2O)c1] | $C_{16}H_{18}N_4O_6S$ | 394.40 |
| MC4-43 | 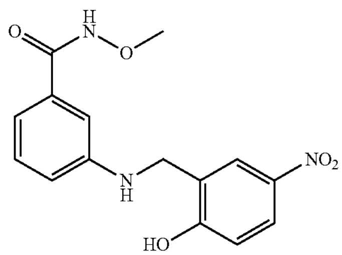 [SMILES: CONC(=O)c1cccc(NCc2cc([N+](=O)[O-])ccc2O)c1] | $C_{15}H_{15}N_3O_5$ | 317.30 |
| MC4-44 | 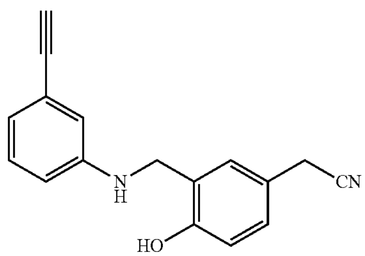 [SMILES: C#Cc1cccc(NCc2cc(CC#N)ccc2O)c1] | $C_{17}H_{14}N_2O$ | 262.31 |
| MC4-45 | 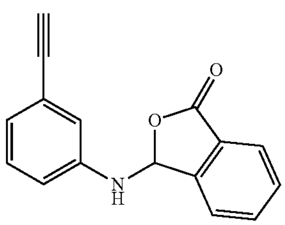 [SMILES: C#Cc1cccc(NC2OC(=O)c3ccccc32)c1] | $C_{16}H_{11}NO_2$ | 249.27 |
| MC4-46 | 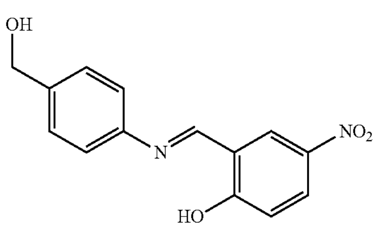 [SMILES: O=[N+]([O-])c1ccc(O)c(/C=N/c2ccc(CO)cc2)c1] | $C_{14}H_{12}N_2O_4$ | 272.26 |
| MC4-47 | 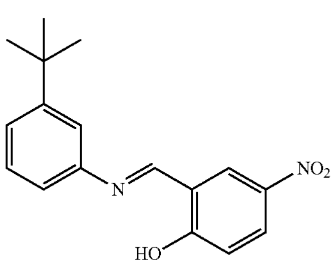 [SMILES: CC(C)(C)c1cccc(/N=C/c2cc([N+](=O)[O-])ccc2O)c1] | $C_{17}H_{18}N_2O_3$ | 298.34 |

-continued

| No. | Structure | Formula | Mol. Wt |
|---|---|---|---|
| MC4-48 | 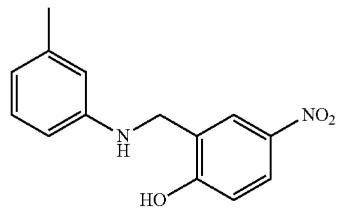 [SMILES: Cc1cccc(NCc2cc([N+](=O)[O-])ccc2O)c1] | $C_{14}H_{14}N_2O_3$ | 258.28 |
| MC4-49 | 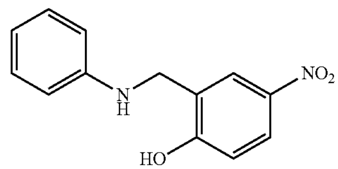 [SMILES: O=[N+]([O-])c1ccc(O)c(CNc2ccccc2)c1] | $C_{13}H_{12}N_2O_3$ | 244.25 |
| MC4-50 | 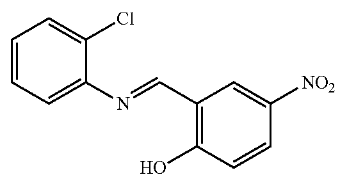 | $C_{13}H_9ClN_2O_3$ | 276.68 |
| MC4-51 | 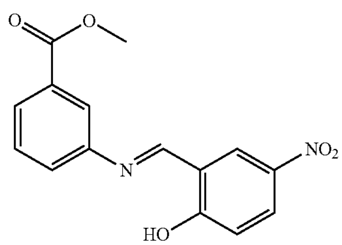 [SMILES: COC(=O)c1cccc(/N=C/c2cc([N+](=O)[O-])ccc2O)c1] | $C_{15}H_{12}N_2O_5$ | 300.27 |
| MC4-52 | 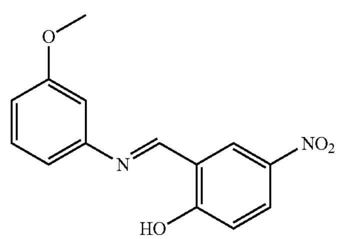 [SMILES: COc1cccc(/N=C/c2cc([N+](=O)[O-])ccc2O)c1] | $C_{14}H_{12}N_2O_4$ | 272.26 |
| MC4-53 | 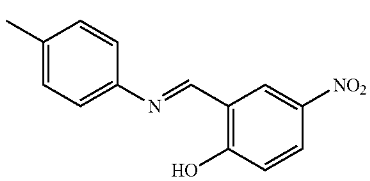 [SMILES: Cc1ccc(/N=C/c2cc([N+](=O)[O-])ccc2O)cc1] | $C_{14}H_{12}N_2O_3$ | 256.26 |
| MC4-54 | 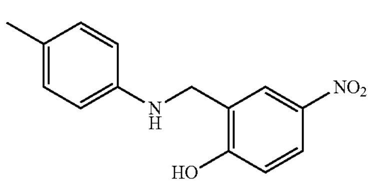 [SMILES: Cc1ccc(NCc2cc([N+](=O)[O-])ccc2O)cc1] | $C_{14}H_{14}N_2O_3$ | 258.28 |

-continued

| No. | Structure | Formula | Mol. Wt |
|---|---|---|---|
| MC4-55 | 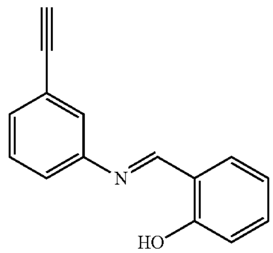 [SMILES: C#Cc1cccc(/N=C/c2ccccc2O)c1] | $C_{15}H_{11}NO$ | 221.26 |
| MC4-56 | 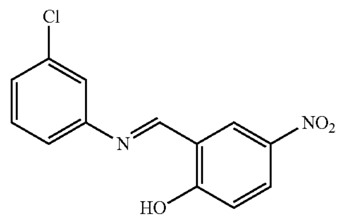 [SMILES: O=[N+]([O-])c1ccc(O)c(/C=N/c2cccc(Cl)c2)c1] | $C_{13}H_9ClN_2O_3$ | 276.68 |
| MC4-57 | 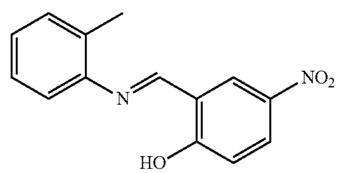 [SMILES: Cc1ccccc1/N=C/c1cc([N+](=O)[O-])ccc1O] | $C_{14}H_{12}N_2O_3$ | 256.26 |
| MC4-58 | 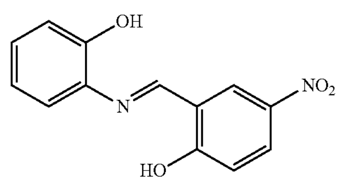 [SMILES: O=[N+]([O-])c1ccc(O)c(/C=N/c2ccccc2O)c1] | $C_{13}H_{10}N_2O_4$ | 258.23 |
| MC4-59 | 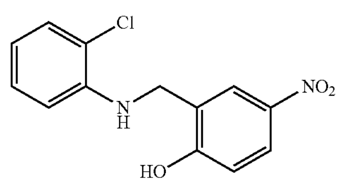 | $C_{13}H_{11}ClN_2O_3$ | 278.69 |
| MC4-60 | 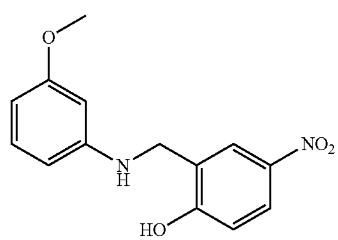 [SMILES: COc1cccc(NCc2cc([N+](=O)[O-])ccc2O)c1] | $C_{14}H_{14}N_2O_4$ | 274.28 |
| MC4-61 | 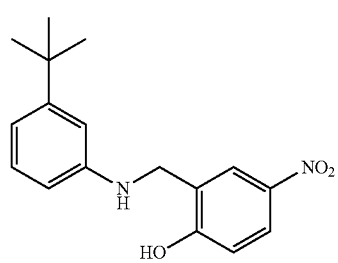 [SMILES: CC(C)(C)c1cccc(NCc2cc([N+](=O)[O-])ccc2O)c1] | $C_{17}H_{20}N_2O_3$ | 300.36 |

-continued
| No. | Structure | Formula | Mol. Wt |
|---|---|---|---|
| MC4-62 | 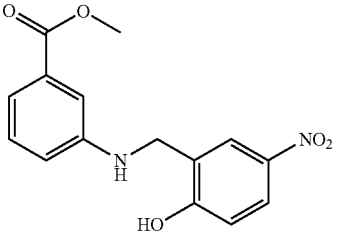 [SMILES: COC(=O)c1cccc(NCc2cc([N+](=O)[O-])ccc2O)c1] | $C_{15}H_{14}N_2O_5$ | 302.29 |
| MC4-63 | 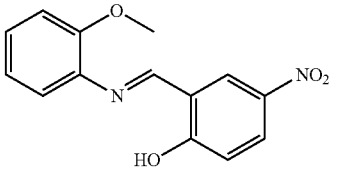 [SMILES: COc1ccccc1/N=C/c1cc([N+](=O)[O-])ccc1O] | $C_{14}H_{12}N_2O_4$ | 272.26 |
| MC4-64 | 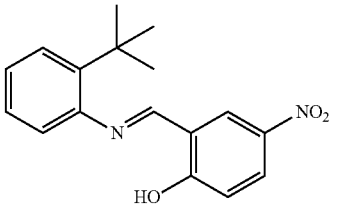 [SMILES: CC(C)(C)c1ccccc1/N=C/c1cc([N+](=O)[O-])ccc1O] | $C_{17}H_{18}N_2O_3$ | 298.34 |
| MC4-65 | 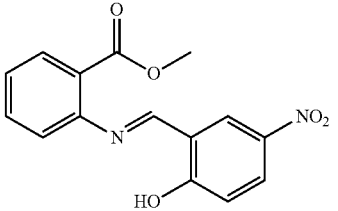 [SMILES: COC(=O)c1ccccc1/N=C/c1cc([N+](=O)[O-])ccc1O] | $C_{15}H_{12}N_2O_5$ | 300.27 |
| MC4-66 | 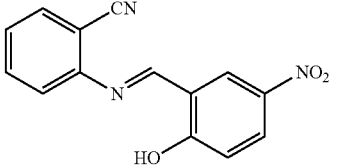 [SMILES: N#Cc1ccccc1/N=C/c1cc([N+](=O)[O-])ccc1O] | $C_{14}H_9N_3O_3$ | 267.24 |
| MC4-67 | 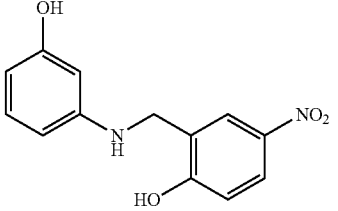 [SMILES: O=[N+]([O-])c1ccc(O)c(CNc2cccc(O)c2)c1] | $C_{13}H_{12}N_2O_4$ | 260.25 |
| MC4-68 | 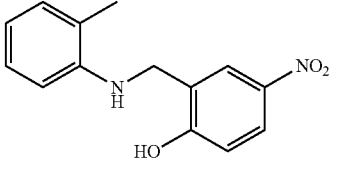 [SMILES: Cc1ccccc1NCc1cc([N+](=O)[O-])ccc1O] | $C_{14}H_{14}N_2O_3$ | 258.28 |

-continued
| No. | Structure | Formula | Mol. Wt |
|---|---|---|---|
| MC4-69 | 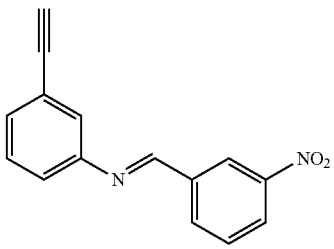 [SMILES: C#Cc1cccc(/N=C/c2cccc([N+](=O)[O-])c2)c1] | C$_{15}$H$_{10}$N$_2$O$_2$ | 250.26 |
| MC4-70 | 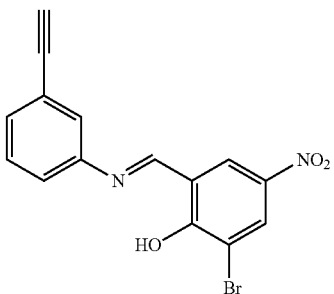 [SMILES: C#Cc1cccc(/N=C/c2cc([N+](=O)[O-])cc(Br)c2O)c1] | C$_{15}$H$_9$BrN$_2$O$_3$ | 345.15 |
| MC4-71 | 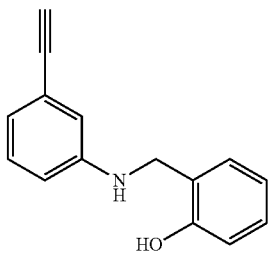 [SMILES: C#Cc1cccc(NCc2ccccc2O)c1] | C$_{15}$H$_{13}$NO | 223.28 |
| MC4-72 | 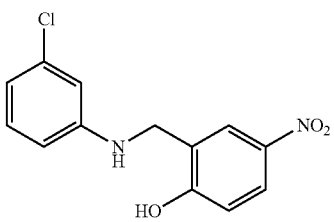 [SMILES: O=[N+]([O-])c1ccc(O)c(CNc2cccc(Cl)c2)c1] | C$_{13}$H$_{11}$ClN$_2$O$_3$ | 278.69 |
| MC4-73 | 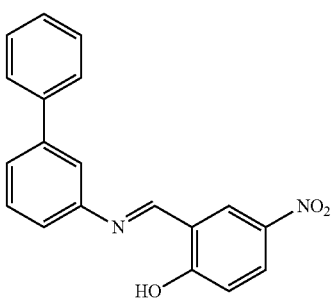 [SMILES: O=[N+]([O-])c1ccc(O)c(/C=N/c2cccc(-c3ccccc3)c2)c1] | C$_{19}$H$_{14}$N$_2$O$_3$ | 318.33 |

-continued

| No. | Structure | Formula | Mol. Wt |
|---|---|---|---|
| MC4-74 | 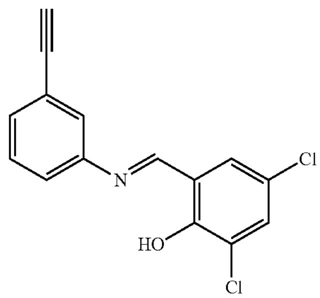 [SMILES: C#Cc1cccc(/N=C/c2cc(Cl)cc(Cl)c2O)c1] | $C_{15}H_9Cl_2NO$ | 290.14 |
| MC4-75 | 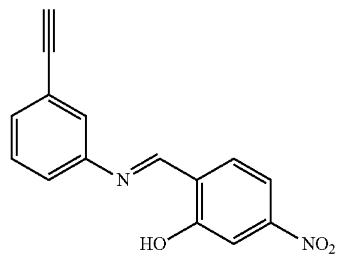 [SMILES: C#Cc1cccc(/N=C/c2ccc([N+](=O)[O-])cc2O)c1] | $C_{15}H_{10}N_2O_3$ | 266.26 |
| MC4-76 | 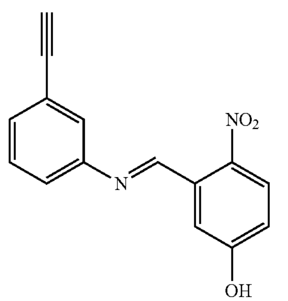 [SMILES: C#Cc1cccc(/N=C/c2cc(O)ccc2[N+](=O)[O-])c1] | $C_{15}H_{10}N_2O_3$ | 266.26 |
| MC4-77 | 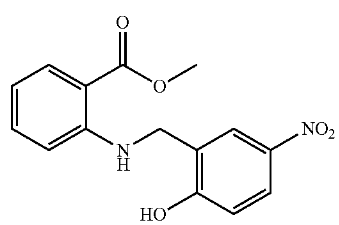 [SMILES: COC(=O)c1ccccc1NCc1cc([N+](=O)[O-])ccc1O] | $C_{15}H_{14}N_2O_5$ | 302.29 |
| MC4-78 | 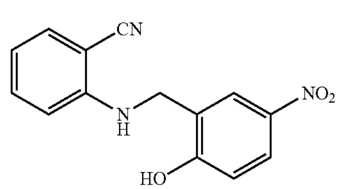 [SMILES: N#Cc1ccccc1NCc1cc([N+](=O)[O-])ccc1O] | $C_{14}H_{11}N_3O_3$ | 269.26 |
| MC4-79 | 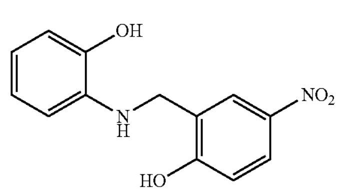 [SMILES: O=[N+]([O-])c1ccc(O)c(CNc2ccccc2O)c1] | $C_{13}H_{12}N_2O_4$ | 260.25 |

-continued

| No. | Structure | Formula | Mol. Wt |
|---|---|---|---|
| MC4-80 | 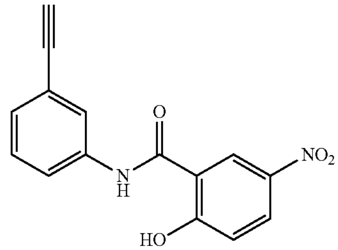 [SMILES: C#Cc1cccc(NC(=O)c2cc([N+](=O)[O-])ccc2O)c1] | $C_{15}H_{10}N_2O_4$ | 282.26 |
| MC4-81 | 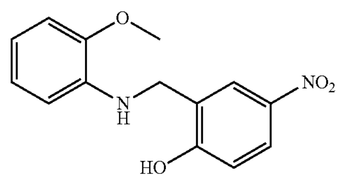 [SMILES: COc1ccccc1NCc1cc([N+](=O)[O-])ccc1O] | $C_{14}H_{14}N_2O_4$ | 274.28 |
| MC4-82 | 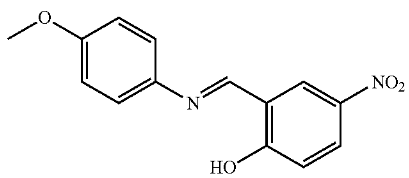 [SMILES: COc1ccc(/N=C/c2cc([N+](=O)[O-])ccc2O)cc1] | $C_{14}H_{12}N_2O_4$ | 272.26 |
| MC4-83 | 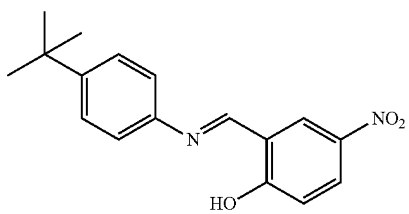 [SMILES: CC(C)(C)c1ccc(/N=C/c2cc([N+](=O)[O-])ccc2O)cc1] | $C_{17}H_{18}N_2O_3$ | 298.34 |
| MC4-84 | 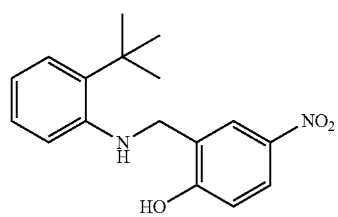 [SMILES: CC(C)(C)c1ccccc1NCc1cc([N+](=O)[O-])ccc1O] | $C_{17}H_{20}N_2O_3$ | 300.36 |
| MC4-85 | 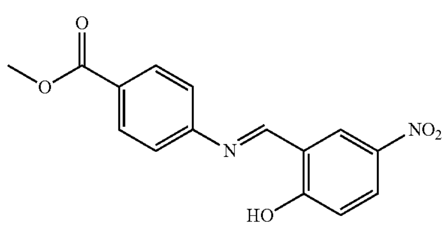 [SMILES: COC(=O)c1ccc(/N=C/c2cc([N+](=O)[O-])ccc2O)cc1] | $C_{15}H_{12}N_2O_5$ | 300.27 |
| MC4-86 | 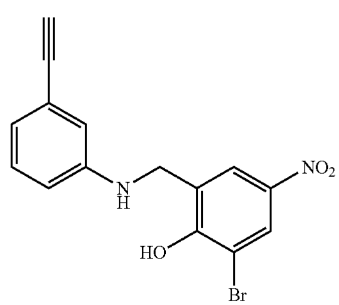 [SMILES: C#Cc1cccc(NCc2cc([N+](=O)[O-])cc(Br)c2O)c1] | $C_{15}H_{11}BrN_2O_3$ | 347.17 |

-continued

| No. | Structure | Formula | Mol. Wt |
|---|---|---|---|
| MC4-87 | 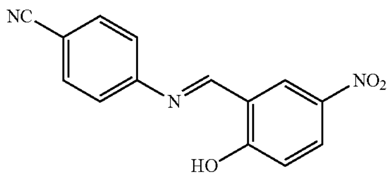 [SMILES: N#Cc1ccc(/N=C/c2cc([N+](=O)[O-])ccc2O)cc1] | $C_{14}H_9N_3O_3$ | 267.24 |
| MC4-88 | 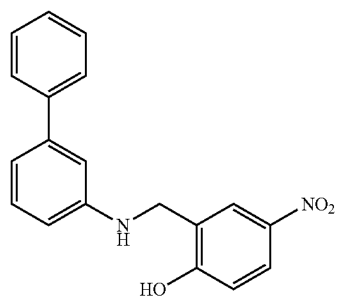 [SMILES: O=[N+]([O-])c1ccc(O)c(CNc2cccc(-c3ccccc3)c2)c1] | $C_{19}H_{16}N_2O_3$ | 320.35 |
| MC4-89 | 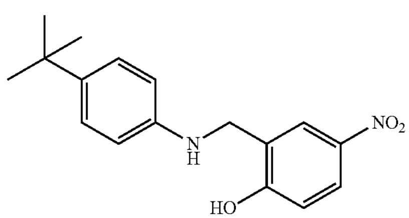 [SMILES: CC(C)(C)c1ccc(NCc2cc([N+](=O)[O-])ccc2O)cc1] | $C_{17}H_{20}N_2O_3$ | 300.36 |
| MC4-90 | 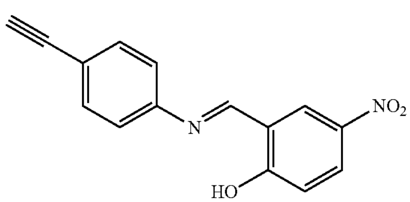 [SMILES: C#Cc1ccc(/N=C/c2cc([N+](=O)[O-])ccc2O)cc1] | $C_{15}H_{10}N_2O_3$ | 266.26 |
| MC4-91 | 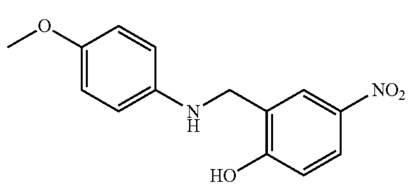 [SMILES: COc1ccc(NCc2cc([N+](=O)[O-])ccc2O)cc1] | $C_{14}H_{14}N_2O_4$ | 274.28 |
| MC4-92 | 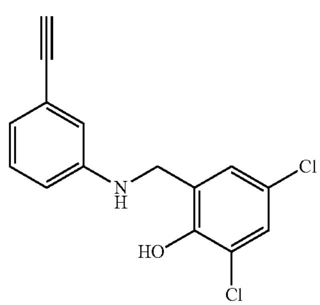 [SMILES: C#Cc1cccc(NCc2cc(Cl)cc(Cl)c2O)c1] | $C_{15}H_{11}Cl_2NO$ | 292.16 |

-continued

| No. | Structure | Formula | Mol. Wt |
|---|---|---|---|
| MC4-93 | 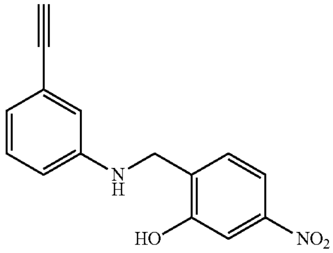 [SMILES: C#Cc1cccc(NCc2ccc([N+](=O)[O-])cc2O)c1] | $C_{15}H_{12}N_2O_3$ | 268.27 |
| MC4-94 | 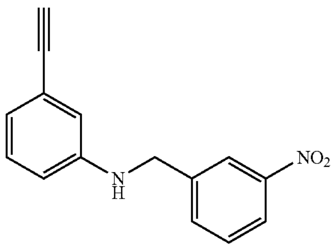 [SMILES: C#Cc1cccc(NCc2cccc([N+](=O)[O-])c2)c1] | $C_{15}H_{12}N_2O_2$ | 252.27 |
| MC4-95 | 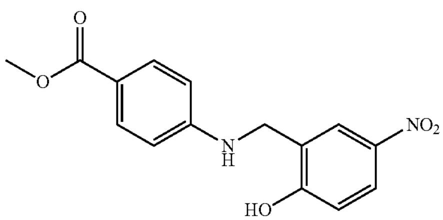 [SMILES: COC(=O)c1ccc(NCc2cc([N+](=O)[O-])ccc2O)cc1] | $C_{15}H_{14}N_2O_5$ | 302.29 |
| MC4-96 | 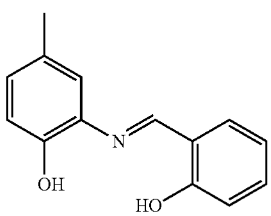 [SMILES: Cc1ccc(O)c(/N=C/c2ccccc2O)c1] | $C_{14}H_{13}NO_2$ | 227.26 |
| MC4-97 | 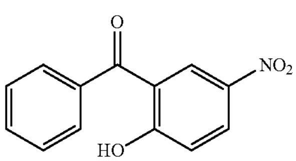 [SMILES: O=C(c1ccccc1)c1cc([N+](=O)[O-])ccc1O] | $C_{13}H_9NO_4$ | 243.22 |
| MC4-98 | 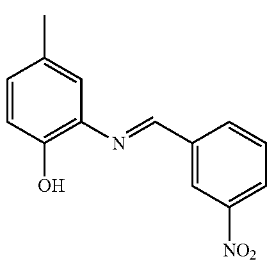 [SMILES: Cc1ccc(O)c(/N=C/c2cccc([N+](=O)[O-])c2)c1] | $C_{14}H_{12}N_2O_3$ | 256.26 |
| MC4-99 | 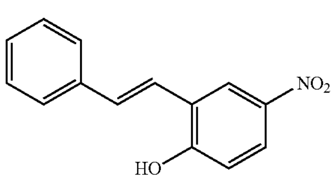 [SMILES: O=[N+]([O-])c1ccc(O)c(/C=C/c2ccccc2)c1] | $C_{14}H_{11}NO_3$ | 241.25 |

| No. | Structure | Formula | Mol. Wt |
|---|---|---|---|
| MC4-100 | 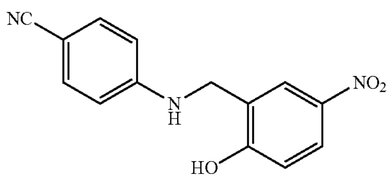 [SMILES: N#Cc1ccc(NCc2cc([N+](=O)[O-])ccc2O)cc1] | $C_{14}H_{11}N_3O_3$ | 269.26 |
| MC4-101 | 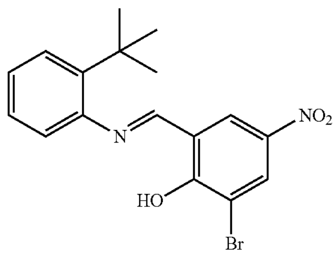 [SMILES: CC(C)(C)c1ccccc1/N=C/c1cc([N+](=O)[O-])cc(Br)c1O] | $C_{17}H_{17}BrN_2O_3$ | 377.24 |
| MC4-102 | 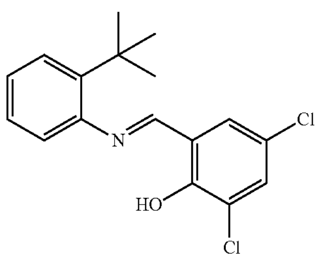 [SMILES: CC(C)(C)c1ccccc1/N=C/c1cc(Cl)cc(Cl)c1O] | $C_{17}H_{17}Cl_2NO$ | 322.23 |
| MC4-103 | 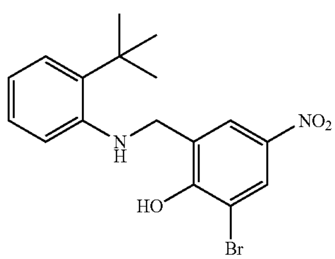 [SMILES: CC(C)(C)c1ccccc1NCc1cc([N+](=O)[O-])cc(Br)c1O] | $C_{17}H_{19}BrN_2O_3$ | 379.25 |
| MC4-104 | 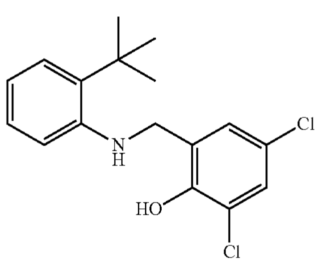 [SMILES: CC(C)(C)c1ccccc1NCc1cc(Cl)cc(Cl)c1O] | $C_{17}H_{19}Cl_2NO$ | 324.25 |
| MC4-105 | 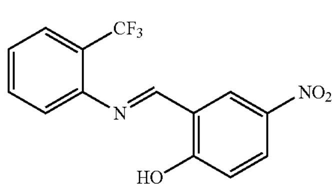 | $C_{14}H_9F_3N_2O_3$ | 310.23 |

-continued
| No. | Structure | Formula | Mol. Wt |
|---|---|---|---|
| MC4-106 | 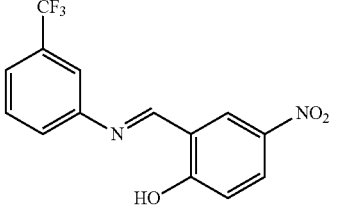 | $C_{14}H_9F_3N_2O_3$ | 310.23 |
| MC4-107 | 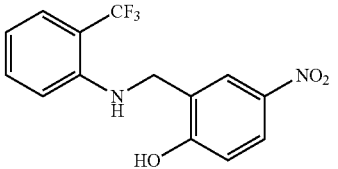 | $C_{14}H_{11}F_3N_2O_3$ | 312.25 |
| MC4-108 | 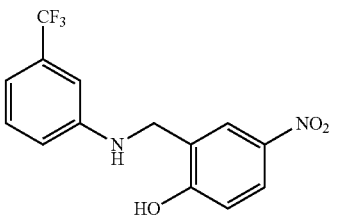 [SMILES: O=[N+]([O-])c1ccc(O)c(CNc2cccc(C(F)(F)F)c2)c1] | $C_{14}H_{11}F_3N_2O_3$ | 312.25 |
| MC4-109 | 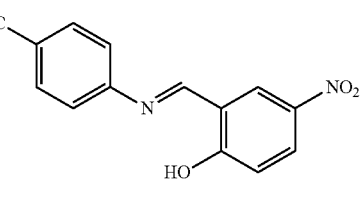 | $C_{14}H_9F_3N_2O_3$ | 310.23 |
| MC4-110 | 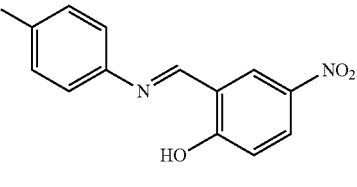 | $C_{13}H_9FN_2O_3$ | 260.22 |
| MC4-111 | 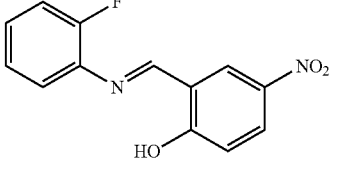 | $C_{13}H_9FN_2O_3$ | 260.22 |
| MC4-112 | 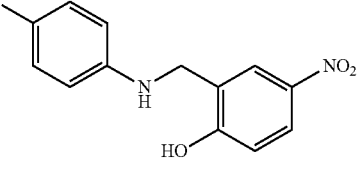 | $C_{13}H_{11}FN_2O_3$ | 262.24 |
| MC4-113 | 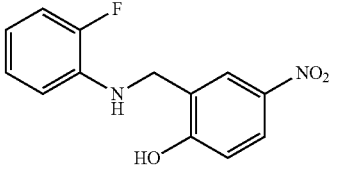 [SMILES: O=[N+]([O-])c1ccc(O)c(CNc2ccccc2F)c1] | $C_{13}H_{11}FN_2O_3$ | 262.24 |

-continued

| No. | Structure | Formula | Mol. Wt |
|---|---|---|---|
| MC4-114 | 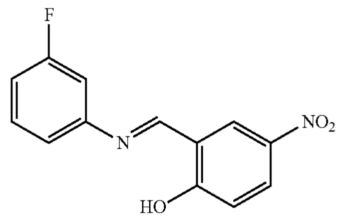 [SMILES: O=[N+]([O-])c1ccc(O)c(/C=N/c2cccc(F)c2)c1] | $C_{13}H_9FN_2O_3$ | 260.22 |
| MC4-115 | 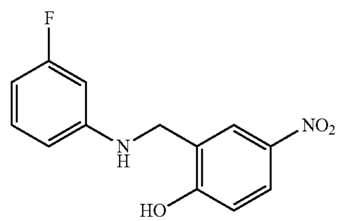 [SMILES: O=[N+]([O-])c1ccc(O)c(CNc2cccc(F)c2)c1] | $C_{13}H_{11}FN_2O_3$ | 262.24 |
| MC4-116 | 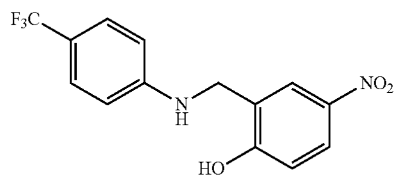 [SMILES: O=[N+]([O-])c1ccc(O)c(CNc2ccc(C(F)(F)F)cc2)c1] | $C_{14}H_{11}F_3N_2O_3$ | 312.25 |
| MC4-117 | 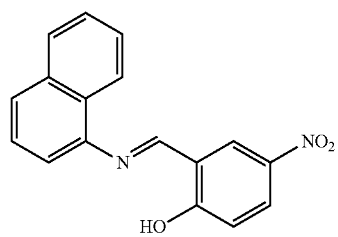 [SMILES: O=[N+]([O-])c1ccc(O)c(/C=N/c2cccc3ccccc23)c1] | $C_{17}H_{12}N_2O_3$ | 292.29 |
| MC4-118 | 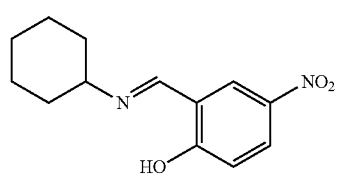 [SMILES: O=[N+]([O-])c1ccc(O)c(/C=N/C2CCCCC2)c1] | $C_{13}H_{16}N_2O_3$ | 248.28 |
| MC4-119 | 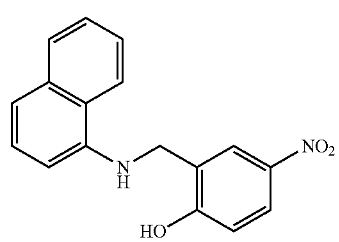 [SMILES: O=[N+]([O-])c1ccc(O)c(CNc2cccc3ccccc23)c1] | $C_{17}H_{14}N_2O_3$ | 294.31 |
| MC4-120 | 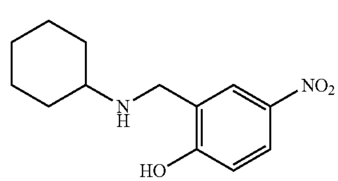 [SMILES: O=[N+]([O-])c1ccc(O)c(CNC2CCCCC2)c1] | $C_{13}H_{18}N_2O_3$ | 250.30 |

-continued

| No. | Structure | Formula | Mol. Wt |
|---|---|---|---|
| MC4-121 | 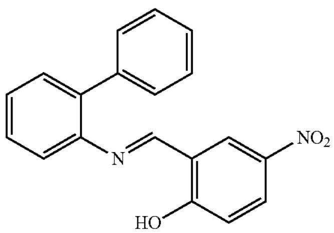 [SMILES: O=[N+]([O-])c1ccc(O)c(/C=N/c2ccccc2-c2ccccc2)c1] | $C_{19}H_{14}N_2O_3$ | 318.33 |
| MC4-122 | 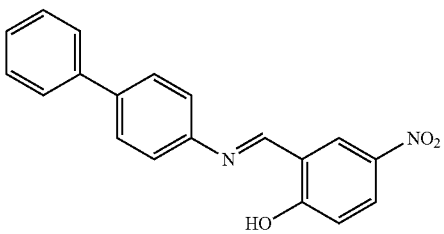 [SMILES: O=[N+]([O-])c1ccc(O)c(/C=N/c2ccc(-c3ccccc3)cc2)c1] | $C_{19}H_{14}N_2O_3$ | 318.33 |
| MC4-123 | 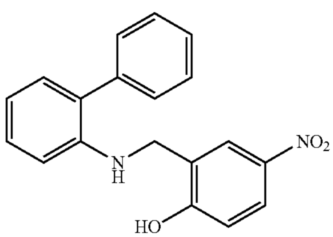 [SMILES: O=[N+]([O-])c1ccc(O)c(CNc2ccccc2-c2ccccc2)c1] | $C_{19}H_{16}N_2O_3$ | 320.35 |
| MC4-124 | 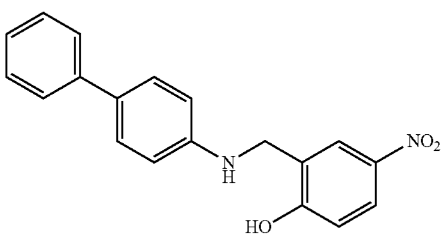 [SMILES: O=[N+]([O-])c1ccc(O)c(CNc2ccc(-c3ccccc3)cc2)c1] | $C_{19}H_{16}N_2O_3$ | 320.35 |
| MC4-125 | 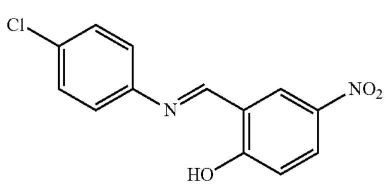 [SMILES: O=[N+]([O-])c1ccc(O)c(/C=N/c2ccc(Cl)cc2)c1] | $C_{13}H_9ClN_2O_3$ | 276.68 |
| MC4-126 | 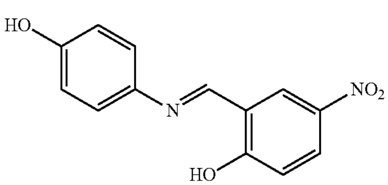 [SMILES: O=[N+]([O-])c1ccc(O)c(/C=N/c2ccc(O)cc2)c1] | $C_{13}H_{10}N_2O_4$ | 258.23 |
| MC4-127 | 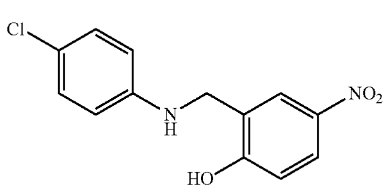 [SMILES: O=[N+]([O-])c1ccc(O)c(CNc2ccc(Cl)cc2)c1] | $C_{13}H_{11}ClN_2O_3$ | 278.69 |

-continued

| No. | Structure | Formula | Mol. Wt |
|---|---|---|---|
| MC4-128 | 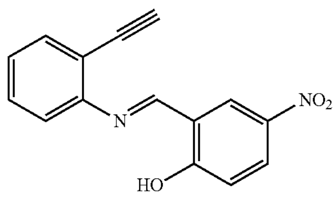 [SMILES: C#Cc1ccccc1/N=C/c1cc([N+](=O)[O-])ccc1O] | $C_{15}H_{10}N_2O_3$ | 266.26 |
| MC4-129 | 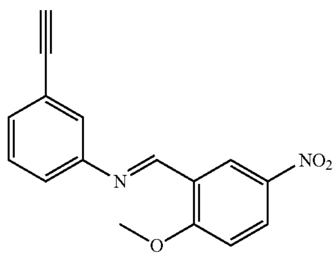 [SMILES: C#Cc1cccc(/N=C/c2cc([N+](=O)[O-])ccc2OC)c1] | $C_{16}H_{12}N_2O_3$ | 280.28 |
| MC4-131 | 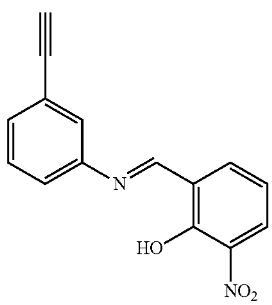 [SMILES: C#Cc1cccc(/N=C/c2cccc([N+](=O)[O-])c2O)c1] | $C_{15}H_{10}N_2O_3$ | 266.26 |
| MC4-132 | 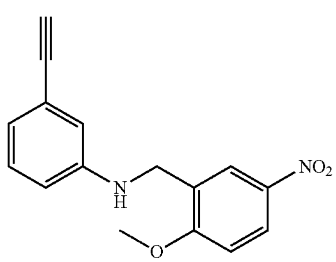 [SMILES: C#Cc1cccc(NCc2cc([N+](=O)[O-])ccc2OC)c1] | $C_{16}H_{14}N_2O_3$ | 282.30 |
| MC4-133 | 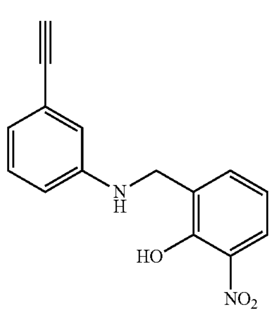 [SMILES: C#Cc1cccc(NCc2cccc([N+](=O)[O-])c2O)c1] | $C_{15}H_{12}N_2O_3$ | 268.27 |
| MC4-134 | 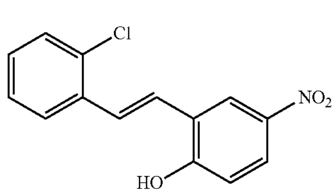 | $C_{14}H_{10}ClNO_3$ | 275.69 |

| No. | Structure | Formula | Mol. Wt |
|---|---|---|---|
| MC4-135 | 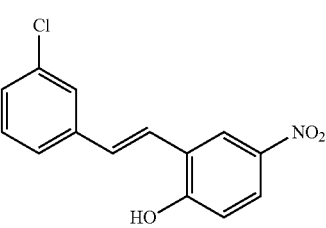 [SMILES: O=[N+]([O-])c1ccc(O)c(/C=C/c2cccc(Cl)c2)c1] | C$_{14}$H$_{10}$ClNO$_3$ | 275.69 |
| MC4-136 | 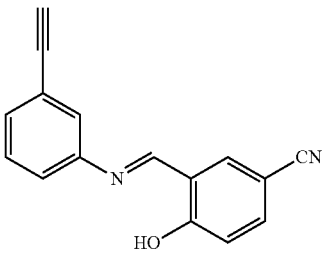 [SMILES: C#Cc1cccc(/N=C/c2cc(C#N)ccc2O)c1] | C$_{16}$H$_{10}$N$_2$O | 246.27 |
| MC4-137 | 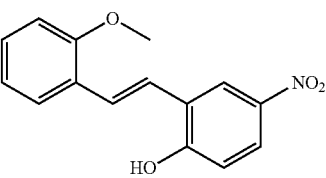 [SMILES: COc1ccccc1/C=C/c1cc([N+](=O)[O-])ccc1O] | C$_{15}$H$_{13}$NO$_4$ | 271.27 |
| MC4-138 | 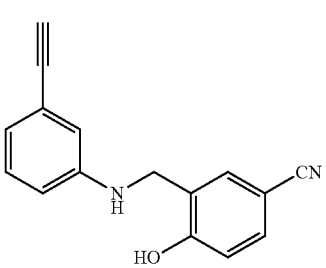 [SMILES: C#Cc1cccc(NCc2cc(C#N)ccc2O)c1] | C$_{16}$H$_{12}$N$_2$O | 248.29 |
| MC4-139 | 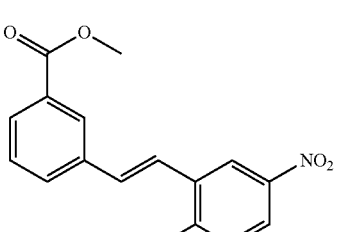 | C$_{16}$H$_{13}$NO$_5$ | 299.28 |
| MC4-140 | 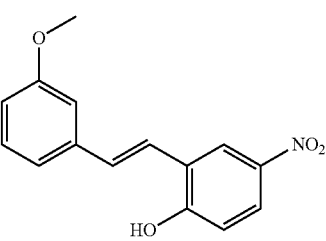 [SMILES: COc1cccc(/C=C/c2cc([N+](=O)[O-])ccc2O)c1] | C$_{15}$H$_{13}$NO$_4$ | 271.27 |

-continued

| No. | Structure | Formula | Mol. Wt |
|---|---|---|---|
| MC4-141 | 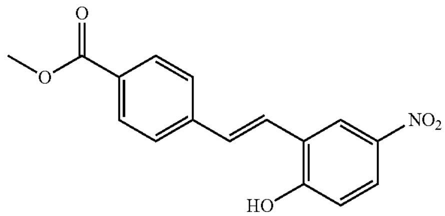 [SMILES: COC(=O)c1ccc(/C=C/c2cc([N+](=O)[O-])ccc2O)cc1] | $C_{16}H_{13}NO_5$ | 299.28 |
| MC4-142 | 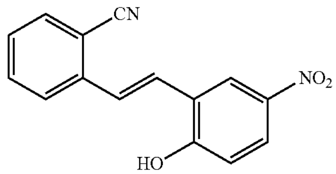 [SMILES: N#Cc1ccccc1/C=C/c1cc([N+](=O)[O-])ccc1O] | $C_{15}H_{10}N_2O_3$ | 266.26 |

REFERENCES (1)(a) Jean, S. S., and Hsueh, P. R. (2011) Int. J. Antimicrob. Agents 37, 291-295. (b) Frieden, T. R. (2013) N. Engl. J. Med. 368, 1857-1859.

(2) Chambers, H. F., and Deleo, F. R. (2009) Nat. Rev. Microbiol. 7, 629-641.

(3) (a) Gardete, S., and Tomasz, A. (2014) J. Clin. Invest. 124, 2836-2840. (b) Nannini, E., Murray, B. E., and Arias, C. A. (2010) Curr. Opin. Pharmacol. 10, 516-521.

(4) Jin, D. J., Cagliero, C., and Zhou, Y N. (2012) FEMS MicrobioLRev. 36, 269-287.

(5) Viktorovskaya, V., and Schneider, D. A. (2015) Gene 556, 19-26.

(6) Santangelo, T. J., and Artsimovitch, 1. (2011) Nat. Rev. Microbiol. 9, 319-329.

(7) Richardson, J. P., and Greenblatt, J. (1996) in *Escherichia coli* and *Salmonella*: Cellular and molecular biology, 2nd ed., pp 822-848, American Society for Microbiology, Washington, D.C.

(8) Greive, S. J., Lins, A. F., and von Hippel, P. H. (2005) J. Biol. Chem. 280, 36397-36408.

(9) (a) Nodwell, J. R., and Greenblatt, J. (1993) Cell 72, 261-268. (b) Burmann, B. M., Luo, X., Rosch, P., Wahl, M. C., and Gottesman, M. E. (2010) Nucleic Acids Res. 38, 314-326.

(10) Werner, F., and Grohmann, D. (2011) Nat. Rev. Microbiol. 9, 85-98.

(11) (a) Kato, J., and Hashimoto, M. (2007) Mol. Syst. Biol. 3, 132. (b) Bubunenko, M., Baker, T., and Court, D. L. (2007) J. Bacteriol. 189, 2844-2853.

(12) (a) Ma, C., Yang, X., Kandemir, H., Mielczarek, M., Johnston, E. B., Griffith, R., Kumar, N., and Lewis, P. J. (2013) ACS Chem. Biol. 8, 1972-1980. (b) Ma, C., Yang, X., and Lewis, P. J. (2016) ACS Infect. Dis. 2, 39-46.

(13) Vassylyev, D. G., Vassylyeva, M. N., Perederina, A., Tahirov, T. H., and Artsimovitch, I. (2007) Nature 448, 157-162.

(14) Liu, B., and Steitz, T. A. (2017) Nucleic Acids Res. 45, 968-974.

(15) Burmann, B. M., Schweimer, K., Luo, X., Wahl, M. C., Stitt, B. L., Gottesman. M. E., and Rosch, P. (2010) Science 328, 501-504.

(16) Yang, X., Molimau, S., Doherty, G. P., Johnston, E. B., Marles-Wright, J., Rothnagel, R., Hankarner, B., Lewis, R. J., and Lewis, P. J. (2009) EMBO Rep. 10, 997-1002.

(17) (a) Beuth, B., Pennell, S., Arnvig, K. B., Martin, S. R., and Taylor, I. A. (2005) EMBO J. 24, 3576-3587. (b) Prasch, S., Jurk, M., Washburn, R. S., Gottesman, M. E., Wöhrl, B. M, and Rosch, P. (2009) Nucleic Acids Res. 37, 4736-4742.

(18) (a) Bubunenko, M., Court, D. L., Al Refaii, A., Saxena, S., Korepanov, A., Friedman, D. I., Gottesman, M. E., and Alix, J. H. (2013) Mol. Microbiol. 87, 382-393. (b) Wong, T., Sosnick, T. R., and Pan, T. (2005) Biochemistry 44, 7535-7542.

(19) Anderson, A. C. (2003) Chem. Biol. 10, 787-797.

(20) Said, N., Krupp, F., Anedchenko, E., Santos, K. F., Dybkov, O., Huang, Y. H., Lee, C. T., Loll, B., Behrmann, E., Bnrger, J., Mielke, T, Loerke, J., Urlaub, H., Spahn, C. M. T, Weber, G., and Wahl, M. C. (2017) Nat. Microbiol. 2, 17062.

(21) Das, R., Loss, S., Li, J., Waugh, D. S., Tarasov, S. Wingfield, P. T., Byrd, R. A., and ltieri, A. S. (2008) J. Mol. Bi ol. 376, 705-720.

(22) Luo, X., Hsiao, H. H., Bubunenko, M., Weber, G., Court, D. L., Gottesman, M. E., Urlaub, H., and Wahl, M. C. (2008) Mol. Cell 31791-802.

(23) Stagno, J. R., Altieri, A. S., Bubunenko, M., Tarasov, S. G., Li, J., Court, D. L., Byrd, R. A., and Ji, X. (2011) Nucleic Acids Res. 39, 7803-7815.

(24) Yang, X., Ma, C., and Lewis, P. J. (2015) Methods 86, 45-50.

(25) Lipinski, C. A., Lombardo, F., Dominy B. W., and Feeney, P. J. (2001) Adv. Drug Delivery Rev. 46, 3-26.

(26) (a) Luecke, L., Weiss A., Graciet, J.-C., Steffanut, P., Klein, C., and Winter, M. A. (2008) Eur. Pat. Appl. EP 1930378. (b) Luecke, L., Weiss A., Graciet, J.-C., Steffanut, P., Klein, C., and Winter, M. A. (2008) Fur. Pat. Appl. EP 1925643.

(27) (a) Cangelosi, G. A., and Brabant, W. H. (1997) J. Bacteriol. 179, 4457-4463. (b) Halford, C., Gonzalez, R., Campuzano, S., Hu. B., Babbitt, J. T., Liu, J., Wang, J., Churchill, B. M., and Haake, D. A. (2013) Antirnicrob. Agents Chemother. 57, 936-943.

(28) O'Neil, J. (2014) Antimicrobial resistance: Tackling a crisis for the health and wealth of nations, Wellcome Trust and HM Government, London.

(29) Chellat, M. F., Raguž, L., and Riedl, R. (2016) Angew. Chem., Int. Ed. 55, 6600-6626.

(30) Goralski, T. D., Dewan, K. K., Alumasa, J. N., Avanzato, V. Place, D. E., Markley, R. L., Katkere, B., Rabadi, S. M., Bakshi, C. S., Keiler, K. C., and Kirirnanjeswara, G. S. (2016) Antimicrob. Agents Chemother. 60, 3276-3282.

(31) Brighenti, E., Trere, D., and Derenzini, M. (2015) Oncotarget 6, 38617-38627.

(32) Ma, C., Yang, X., and Lewis, P. J. (2016) Microbiol. Mol. Biol. Rev. 80, 139-160.

(33) Studier, F. W.; Moffatt, B A. (1986). *Mol. Biol.* 189, 113-130.

(34) Vassylyev, D. G.; Vassylyeva, M. N.; Perederina. A.; Tahirov, T. H.: Artsimovitch, I. (2007) *Nature* 448, 157-162.

(35) Liu, B.; Steitz, T. A. (2017)*Nucleic Acids Res.* 45, 968-974.

(36) Stagno, J. R.; Altieri, A. S.; Bubunenko, M.; Tarasov, S. G.; Li, J.; Court, D. L.; Byrd R. A.; Ji, X. (2011) *Nucleic Acids Res.* 39, 7803-7815.

(37) Beuth, B.; Pennell, S.; Arnvig, K. B.; Martin S. R.; Taylor, I. A. (2005) *EMBO J.* 24, 3576-3587.

(38) Burmann, B. M.; Schweimer, K.; Luo, X.; Wahl, M. C.; Stitt, B. L.; Gottesman. M. E. Rosch, P. (2010) *Science* 328, 501-504.

(39) Ma, C.; Mobli, M.; Yang, X.; Keller, A. N.; King G. F.; Lewis, P. J. (2015) *Nucleic Acids Res.* 43, 2829-2840.

(40) Pettersen, E. F.; Goddard, T. D.; Huang, C. C.; Couch, G. S.; Greenblatt, D. M.; Meng E. C.; Ferrin, T E. (2004) *J. Comput. Chem.* 25, 1605-1612.

(41) Yang, X.; Ma C.; Lewis, P. J. (2015) Methods 86, 45-50.

(42) CLSI, Clinical and Laboratory Standards Institute. (2015) Performance Standards for Antimicrobial Susceptibility Testing, Twenty-Fifth Informational Supplement (M100S25).

(43) Bi, Y; Yang, X.; Zhang, T.; Lii, Z.; Zhang, X.; Lu, J.; Cheng, K. Xu, J.; Wang, H.; Lv, G.; Lewis, P. J.; Meng Q.; Ma, C. (2015) *Eur J Med Chem.* 101, 71-80

(44) Heckman K. L.; Pease, L. R. (2007) *Nat. Protoc.* 2, 924-932.

(45) Ma, C.; Yang, X.; Lewis, P. J. (2016)*ACS Infect. Dis.* 2, 39-46.

(46) Neylon, C.; Brown, S. E.; Kralicek, A. V.; Miles, C. S.: Love, C. A.; Dixon, N. E. (2000) *Biochemistry* 39, 11989-11999.

(47) Ma, C.; Yang, X.; Kandemir, H.; Mielczarek, M.; Johnston, E. B.; Griffith, R.; Kumar, N.; Lewis, P. J. (2013) *ACS Chem. Biol.* 8, 1972-1980.

What is claimed is:

1. A method of treating or preventing a bacterial or a protozoal infection in a subject, the method comprising: administering a therapeutically effective amount of a compound of Formula 1 to said subject, wherein said compound has the structure:

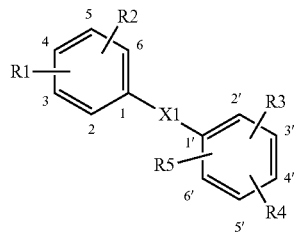

Formula 1 or a pharmaceutically acceptable salt or a solvate thereof, wherein:

$X_1$ is —NH—$CH_2$; and $R_1$ is selected from the group consisting of hydrogen, acetyl, ethynyl, carboxy, carboxymethyl, hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo;

$R_2$ is selected from the group consisting of acetyl, ethynyl, carboxy, carboxymethyl, hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo;

$R_3$ is nitro;

$R_4$ is chloro, bromo, fluoro, cyano, cyanomethyl, carboxymethyl, methoxy, or nitro; and $R_5$ is hydroxy.

2. The method of claim 1, wherein said compound is administered through an oral, parenteral, topical, or rectal route.

3. The method of claim 1, wherein said bacterial infection is caused by a bacterium selected from the group consisting of *Enterococcus faecalis, Staphylococcus aureus, Acinetobacter baumannii*, and *Streptococcus pneumoniae*.

4. The method of claim 1, wherein said compound inhibits a NusB-NusE interaction.

5. The method of claim 4, wherein said NusB-NusE interaction comprises the interaction of a NusB selected from the group consisting of NusB E81, NusB Y18 and NusB E75, and a NusE selected from the group consisting of NusE H15, NusE D19 and NusE R16.

6. The method of claim 1, wherein said compound is selected from the group consisting of:

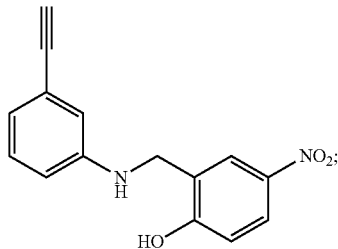
MC4-19

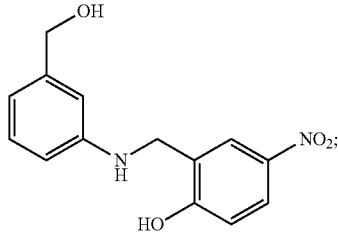
MC4-29

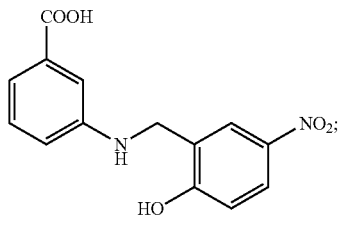
MC4-30

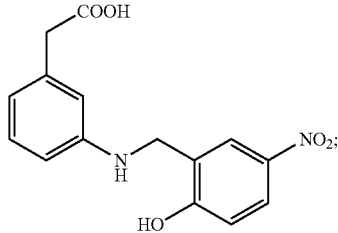
MC4-31

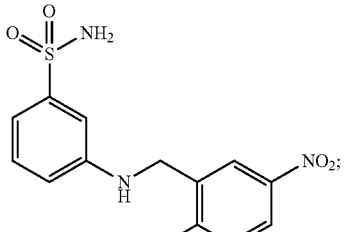
MC4-35

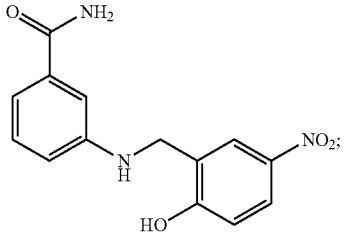
MC4-36

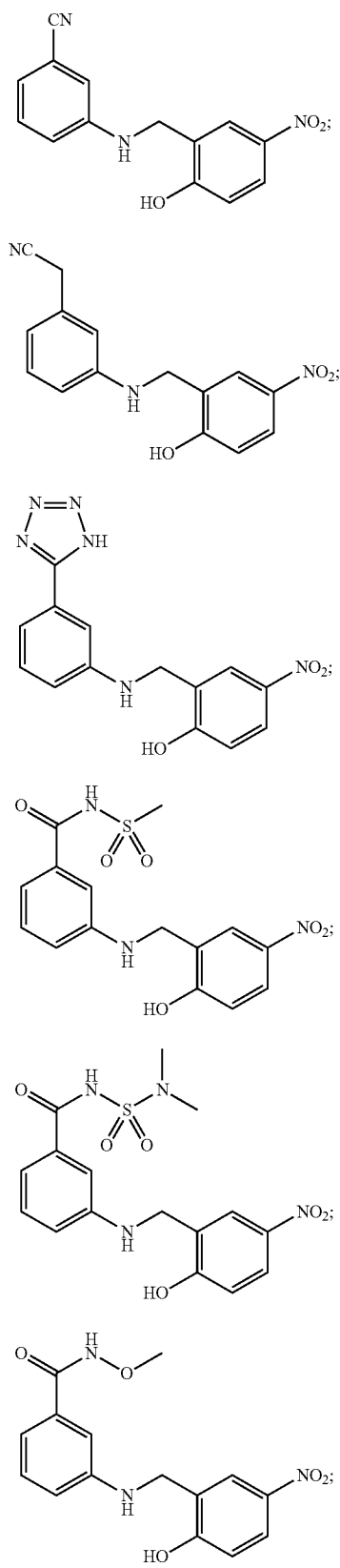
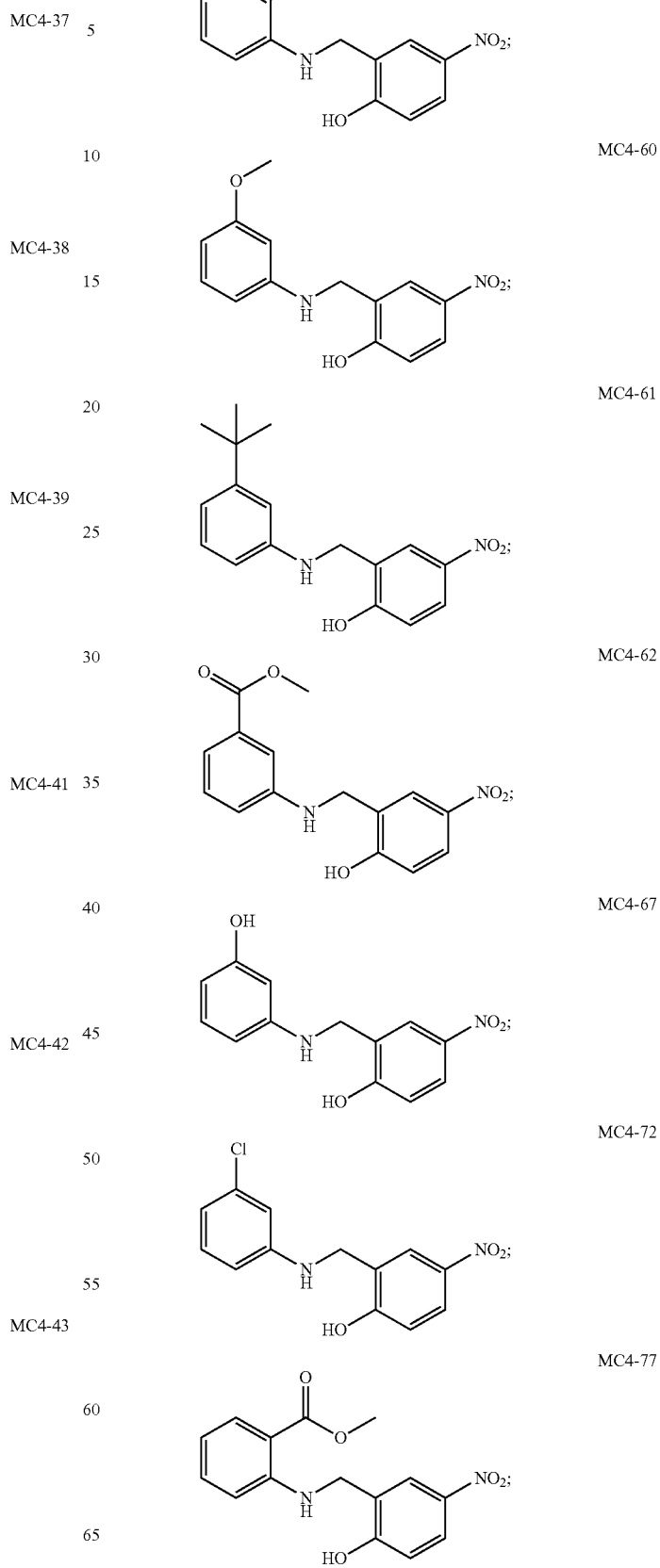

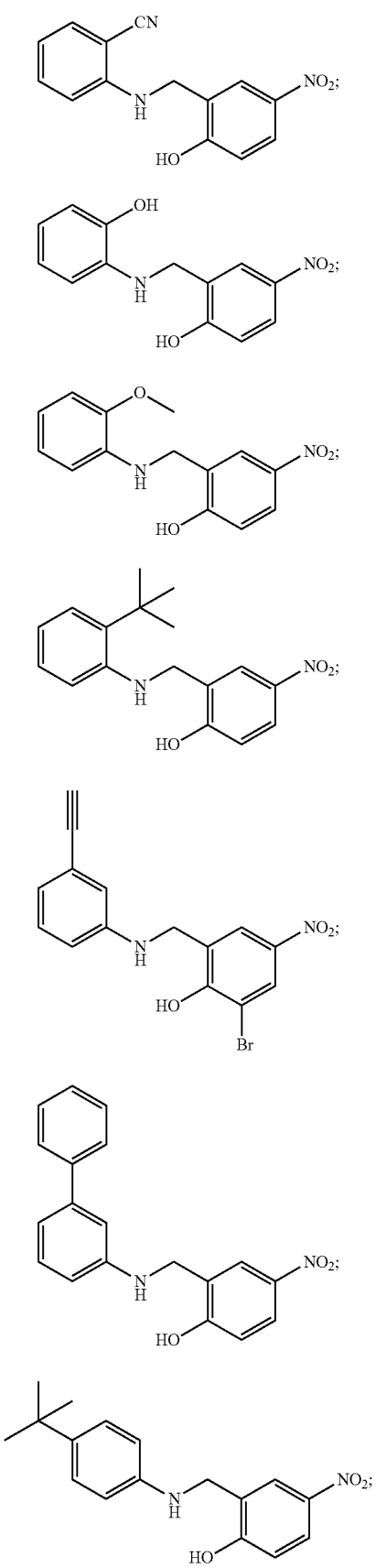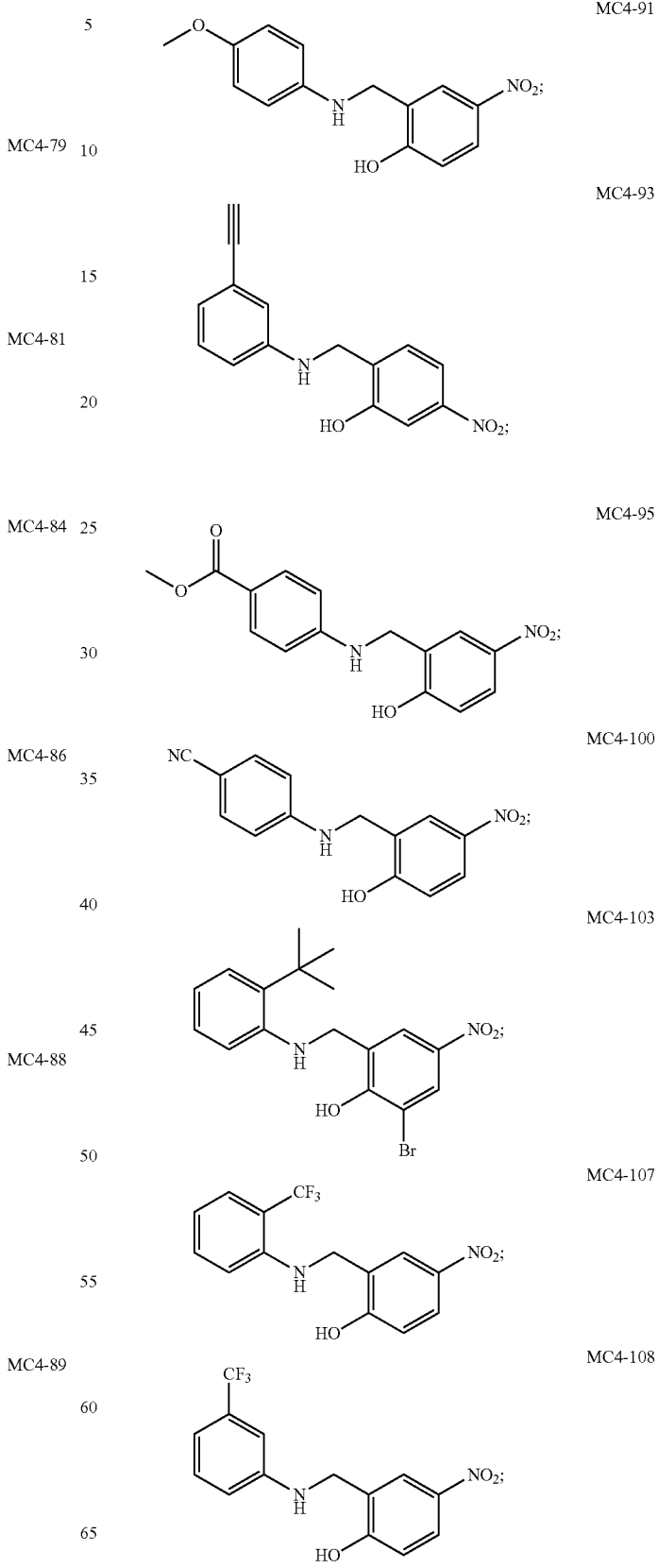

MC4-112
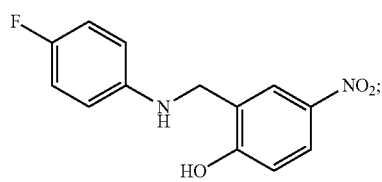
MC4-113
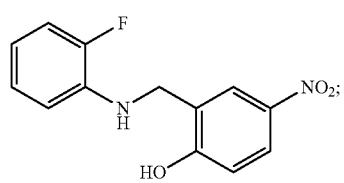
MC4-115
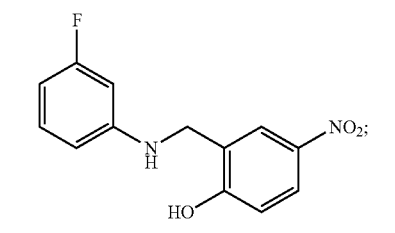
MC4-116
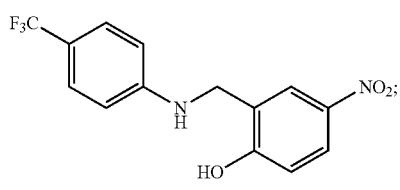
MC4-123
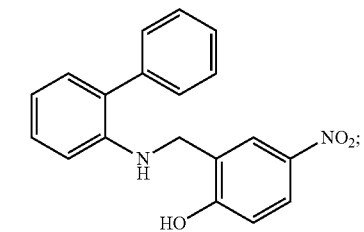
MC4-124
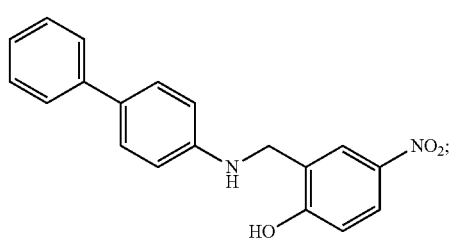
MC4-127
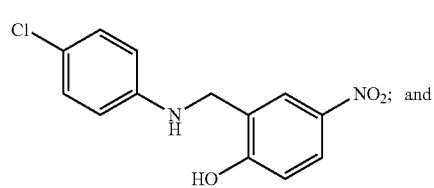
MC4-133
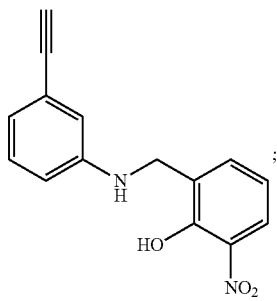
or a pharmaceutically acceptable salt or a solvate thereof.
7. The method of claim 1, wherein said compound is selected from the group consisting of:
MC4-19
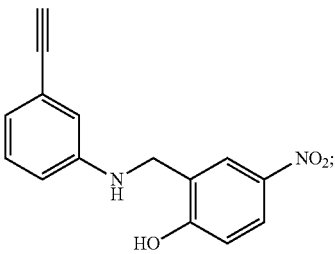
MC4-42
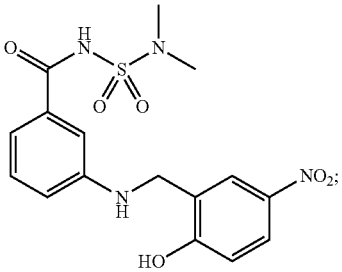
MC4-41
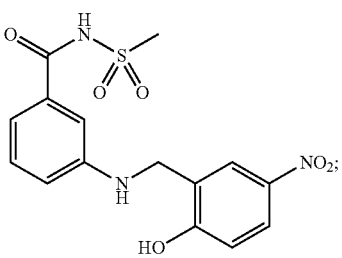
MC4-43
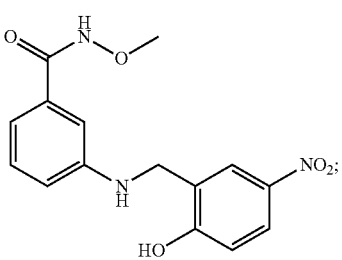

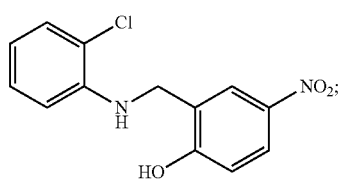
MC4-59
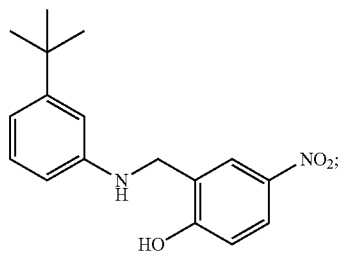
MC4-61
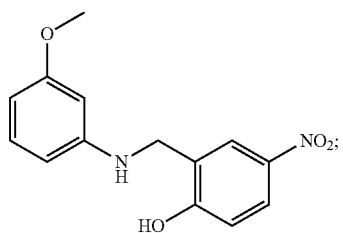
MC4-60
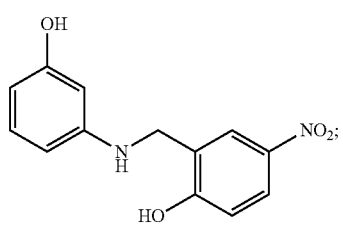
MC4-67
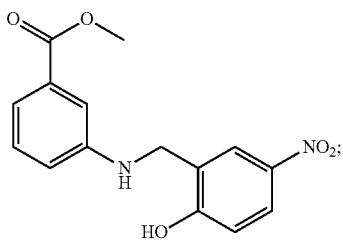
MC4-62
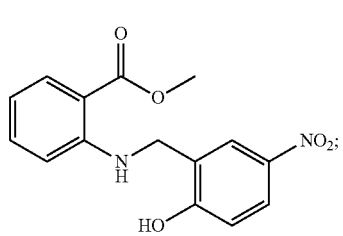
MC4-77
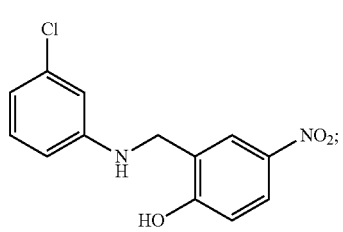
MC4-72
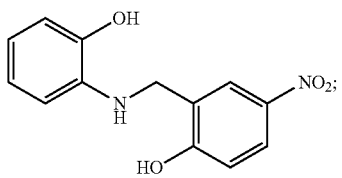
MC4-79
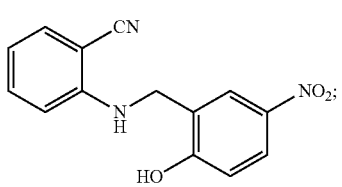
MC4-78
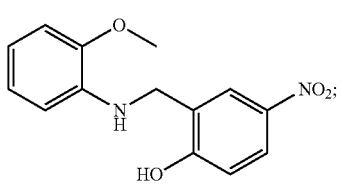
MC4-81
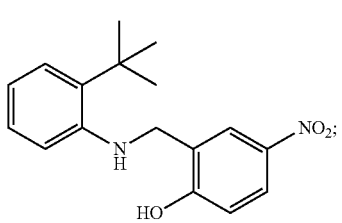
MC4-84
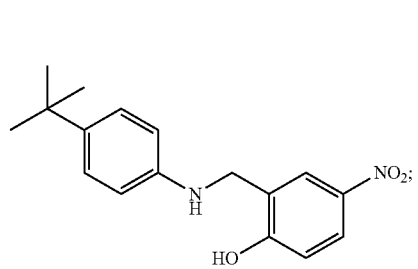
MC4-89
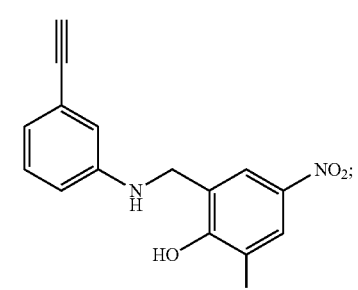
MC4-86
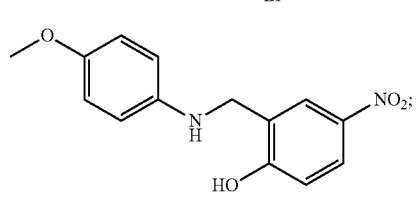
MC4-91

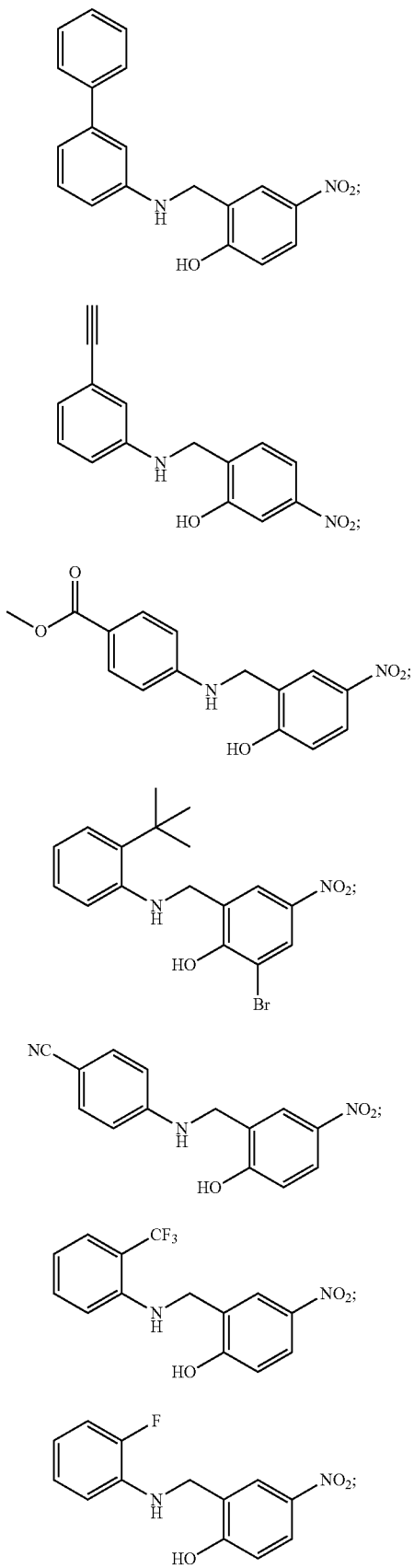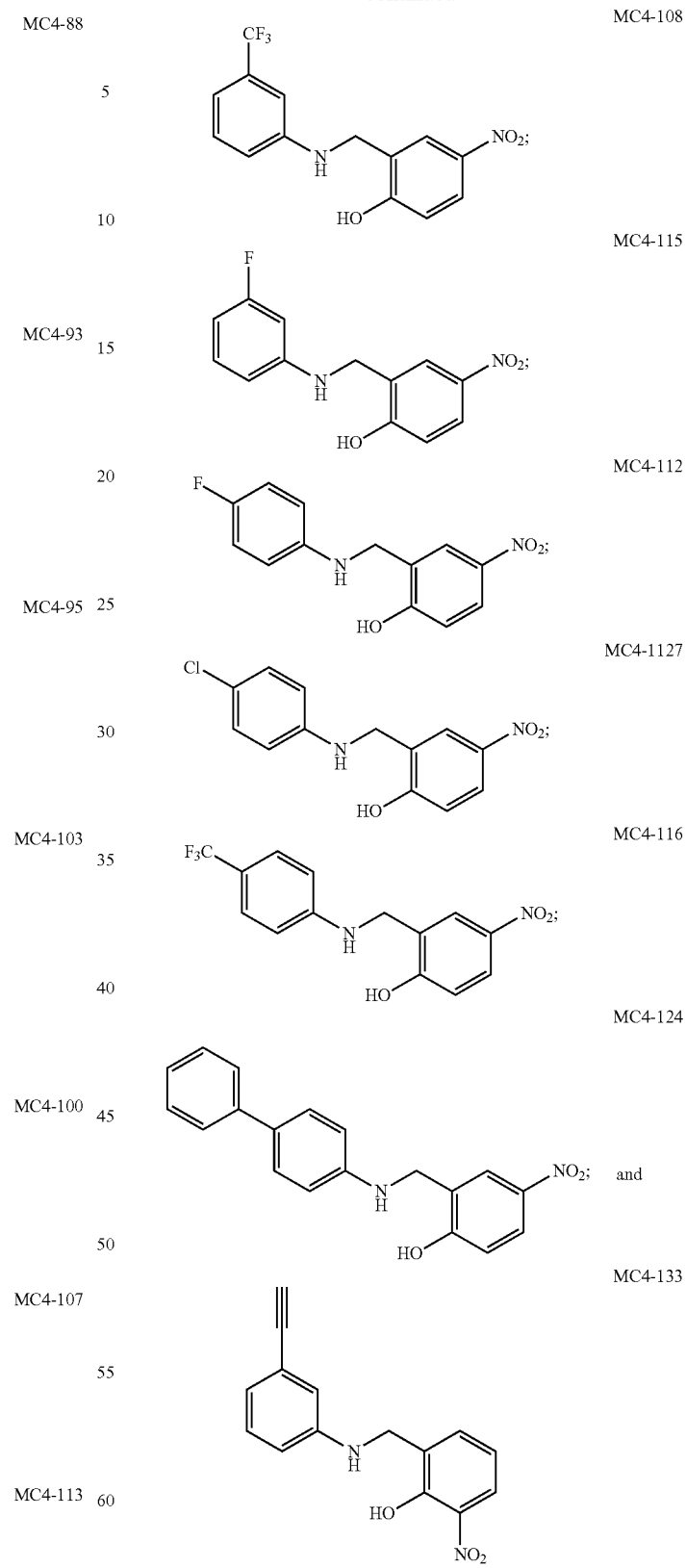
or a pharmaceutically acceptable salt or a solvate thereof.
8. The method of claim 1, wherein said compound is selected from the group consisting of:

MC4-84

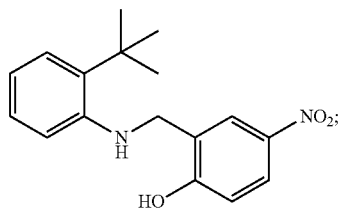

and

MC4-123

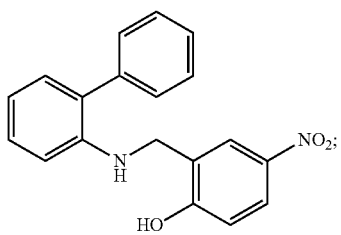

or a pharmaceutically acceptable salt or a solvate thereof.

9. The method of claim 1, wherein the bacterial infection is a *Staphylococcus aureus* infection.

10. The method of claim 1, wherein $R_1$ is t-butyl, ethynyl, phenyl, cyanomethyl, cyano, carboxymethyl, hydroxyl, methoxy, fluoro, chloro, or trifluoromethyl.

11. The method of claim 1, wherein the compound has Formula 4:

Formula 4

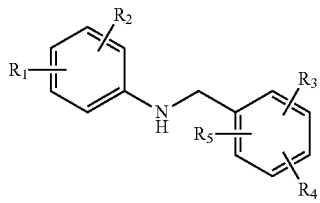

a pharmaceutically acceptable salt, or a solvate thereof, wherein:

$R_1$ is selected from the group consisting of hydrogen, acetyl, ethynyl, carboxy, carboxymethyl, hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo;

$R_2$ is selected from the group consisting of acetyl, ethynyl, carboxy, carboxymethyl, hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo;

$R_3$ is nitro;

$R_4$ is chloro, bromo, fluoro, cyano, cyanomethyl, carboxymethyl, methoxy, and nitro; and $R_5$ is hydroxy.

12. The method of claim 11, wherein $R_1$ is t-butyl, ethynyl, phenyl, cyanomethyl, cyano, Carboxymethyl, methoxy, fluoro, chloro, or trifluoromethyl.

13. The method of claim 12, wherein $R_4$ is nitro.

14. The method of claim 1, wherein the compound has Formula 5:

Formula 5

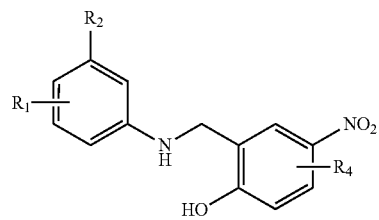

a pharmaceutically acceptable salt, or a solvate thereof, wherein:

$R_1$ is selected from the group consisting of hydrogen, acetyl, ethynyl, carboxy, carboxymethyl, hydroxymethyl, methoxy, methoxycarbonyl, aminosulfonyl, aminocarbonyl, cyano, tetrazolyl, dimethylaminosulfonylaminocarbonyl, cyanomethyl, acetylaminosulfonyl, methoxyaminocarbonyl, methylsulfonylaminocarbonyl, t-butyl, fluoro, chloro, bromo, phenyl, trifluoromethyl and benzo;

$R_2$ is t-butyl, ethynyl, phenyl, cyanomethyl, cyano, carboxymethyl, methoxy, fluoro, chloro, or trifluoromethyl; and $R_4$ is chloro, bromo, fluoro, cyano, cyanomethyl, carboxymethyl, methoxy, or nitro.

15. The method of claim 14, wherein the bacterial infection is *Staphylococcus aureus, Streptococcus pneumoniae, Enterococcus faecalis,* or *Acinetobacter baumannii* infection.

16. The method of claim 14, wherein the bacterial infection is a *Staphylococcus aureus* infection.

\* \* \* \* \*

SEQUENCE LISTING

```
<160> NUMBER OF SEQ ID NOS: 10

<210> SEQ ID NO 1
<211> LENGTH: 26
<212> TYPE: DNA
<213> ORGANISM: Artificial Sequence
<220> FEATURE:
<223> OTHER INFORMATION: Primer for B. subtilis nusB

<400> SEQUENCE: 1
aaaggagatc tagacatgaa agaaga                                            26

<210> SEQ ID NO 2
<211> LENGTH: 23
<212> TYPE: DNA
<213> ORGANISM: Artificial Sequence
<220> FEATURE:
<223> OTHER INFORMATION: Primer for B. subtilis nusB

<400> SEQUENCE: 2
ttttctggta ccctatgatt ccc                                               23

<210> SEQ ID NO 3
<211> LENGTH: 29
<212> TYPE: DNA
<213> ORGANISM: Artificial Sequence
<220> FEATURE:
<223> OTHER INFORMATION: Primer for nusB mutants

<400> SEQUENCE: 3
ctttgcaggc actagctcaa attgatgtc                                         29

<210> SEQ ID NO 4
<211> LENGTH: 29
<212> TYPE: DNA
<213> ORGANISM: Artificial Sequence
<220> FEATURE:
<223> OTHER INFORMATION: Primer for nusB mutants

<400> SEQUENCE: 4
gacatcaatt tgagctagtg cctgcaaag                                         29
```

```
<210> SEQ ID NO 5
<211> LENGTH: 29
<212> TYPE: DNA
<213> ORGANISM: Artificial Sequence
<220> FEATURE:
<223> OTHER INFORMATION: Primer for nusB mutants

<400> SEQUENCE: 5
gaattggaag ctcgatgcga ttgccaatg                                29

<210> SEQ ID NO 6
<211> LENGTH: 29
<212> TYPE: DNA
<213> ORGANISM: Artificial Sequence
<220> FEATURE:
<223> OTHER INFORMATION: Primer for nusB mutants

<400> SEQUENCE: 6
cattggcaat cgcatcgagc ttccaattc                                29

<210> SEQ ID NO 7
<211> LENGTH: 29
<212> TYPE: DNA
<213> ORGANISM: Artificial Sequence
<220> FEATURE:
<223> OTHER INFORMATION: Primer for nusB mutants

<400> SEQUENCE: 7
gattgccaat gttgcccgtg cgattttgc                                29

<210> SEQ ID NO 8
<211> LENGTH: 29
<212> TYPE: DNA
<213> ORGANISM: Artificial Sequence
<220> FEATURE:
<223> OTHER INFORMATION: Primer for nusB mutants

<400> SEQUENCE: 8
gcaaaatcgc acgggcaaca ttggcaatc                                29

<210> SEQ ID NO 9
<211> LENGTH: 24
<212> TYPE: DNA
<213> ORGANISM: Artificial Sequence
<220> FEATURE:
<223> OTHER INFORMATION: Primer for B. subtilis nusE

<400> SEQUENCE: 9
aaggagggtc tagaatggca aaac                                     24

<210> SEQ ID NO 10
<211> LENGTH: 27
<212> TYPE: DNA
<213> ORGANISM: Artificial Sequence
<220> FEATURE:
<223> OTHER INFORMATION: Primer for B. subtilis nusE

<400> SEQUENCE: 10
ctatatttta ggtaccaagt ttaattt                                  27
```